US007612047B2

(12) United States Patent
Douglass, III et al.

(10) Patent No.: US 7,612,047 B2
(45) Date of Patent: Nov. 3, 2009

(54) DEGRADATION-RESISTANT MONONUCLEOSIDE PHOSPHATE COMPOUNDS

(75) Inventors: James G. Douglass, III, Apex, NC (US); Benjamin R. Yerxa, Raleigh, NC (US); Sammy R. Shaver, Chapel Hill, NC (US); Ward M. Peterson, Morrisville, NC (US); Edward G. Brown, Cary, NC (US); Christopher S. Crean, Pittsboro, NC (US); José L. Boyer, Chapel Hill, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 12/208,265

(22) Filed: Sep. 10, 2008

(65) Prior Publication Data

US 2009/0076256 A1 Mar. 19, 2009

Related U.S. Application Data

(63) Continuation of application No. 11/285,221, filed on Nov. 21, 2005, now Pat. No. 7,435,724, which is a continuation-in-part of application No. 10/082,998, filed on Feb. 27, 2002, now Pat. No. 7,115,585.

(51) Int. Cl.
*A01N 43/04* (2006.01)
*A61K 31/70* (2006.01)

(52) U.S. Cl. ............... 514/45; 514/46; 514/47; 514/48; 514/49; 514/50; 514/51; 536/26.2; 536/26.23; 536/26.26

(58) Field of Classification Search ............ None
See application file for complete search history.

(56) References Cited

U.S. PATENT DOCUMENTS

| 3,321,463 | A | 5/1967 | Moffatt |
| 5,292,498 | A | 3/1994 | Boucher, Jr. |
| 5,628,984 | A | 5/1997 | Boucher, Jr. |
| 5,635,160 | A | 6/1997 | Stutts, III et al. |
| 5,654,285 | A | 8/1997 | Ingall et al. |
| 5,721,219 | A | 2/1998 | Ingall et al. |
| 5,747,496 | A | 5/1998 | Cox et al. |
| 5,837,861 | A | 11/1998 | Pendergast et al. |
| 5,900,407 | A | 5/1999 | Yerxa et al. |
| 5,955,447 | A | 9/1999 | Ingall et al. |
| 6,166,022 | A | 12/2000 | Brown et al. |
| 6,319,908 | B1 | 11/2001 | Yerxa et al. |
| 6,323,187 | B1 | 11/2001 | Yerxa et al. |
| 7,018,985 | B1 | 3/2006 | Boyer et al. |
| 7,115,585 | B2 | 10/2006 | Yerxa et al. |
| 7,132,408 | B2 | 11/2006 | Boyer et al. |
| 7,435,724 | B2 | 10/2008 | Douglass et al. |

FOREIGN PATENT DOCUMENTS

| WO | WO 92/17488 | 10/1992 |
| WO | WO 94/18216 | 8/1994 |
| WO | WO 97/03084 | 1/1997 |
| WO | WO 98/28300 | 7/1998 |
| WO | WO 00/33080 | 6/2000 |
| WO | WO 00/34283 | 6/2000 |
| WO | WO 01/19826 | 3/2001 |
| WO | WO 01/36421 | 5/2001 |
| WO | WO 01/39781 | 6/2001 |
| WO | WO 03/072067 | 9/2003 |

OTHER PUBLICATIONS

Abbracchio and Burnstock, "Purinergic Signalling: Pathophysiological Roles," *Jpn J. Pharmacol*, 78:113-120 (1998).

Brown, et al., "Evidence that UTP and ATP Regulate Phospholipase C through a Common Extracellular 5'-Nucleotide Receptor in Human Airway Epithelial Cells," *Mol. Pharmocol*. 40:648-55 (1991).

Drutz, et al., "Uridine 5' Triphosphate (UTP) Regulates Mucociliary Clearance via Purinergic Receptor Activation," *Drug Dev. Res.* 37(3):185 (1996).

Gobran, "P2u purinoceptor stimulation of surfactant secretion coupled to phosphatidylcholine hydrolysis in type II cells," *Am. J. Physiol*. 267:L625-L633 (1994).

Letham, M., et al., "Nucleotide Regulation of Goblet Cells in Human Airway Epithelial Explants: Normal Exocytosis in Cystic Fibrosis," *Am. J. Respir. Cell Mol. Biol*. 9:315-22 (1993).

Mason, S., et al. "Regulation of transepithelial ion transport and intracellular calcium by extracellular ATP in human normal and cystic fibrosis airway epithelium," *Br. J. Pharmacol*. 103:1649-56 (1991).

Moffatt et al., "Nucleoside polyphosphates . . . ", Journal of the American Chemical Society 80, 3756-61, 1958.

Schwartz, "Current Concepts in Ophthamology," *N.Engl. J. Med.*, 290:182-186 (1978).

Yerxa, et al., *Drugs of the Future*, 24:759-769 (1999).

*Primary Examiner*—Patrick T Lewis
(74) *Attorney, Agent, or Firm*—Howrey LLP; Viola T. Kung

(57) ABSTRACT

The present invention relates to mononucleoside phosphate compounds that have the benefits of a dinucleotide pharmaceutical. These mononucleoside phosphates can be made from a mononucleotide that has been modified by attaching a degradation-resistant substituent on the terminal phosphate of a polyphosphate mononucleotide. By attaching this degradation-resistant substituent, the stability from degradation matches or exceeds those of certain dinucleotides. The mononucleoside phosphate compounds of the present invention are useful in preventing and treating epithelial tissue diseases or diseases or disorders associated with platelet aggregation.

6 Claims, No Drawings

DEGRADATION-RESISTANT MONONUCLEOSIDE PHOSPHATE COMPOUNDS

This application is a continuation of U.S. application Ser. No. 11/285,221, filed Nov. 21, 2005 now U.S. Pat. No 7,435,724; which is continuation-in-part of U.S. application Ser. No. 10/082,998, filed Feb. 27, 2002 now U.S. Pat. No. 7,115,585. The contents of the above applications are incorporated herein by reference in their entirety.

TECHNICAL FIELD

The present invention relates to novel mononucleoside phosphate compounds that have been modified by attaching a degradation-resistant substituent on the terminal phosphate. The present invention also relates to methods of using such compounds in the prevention or treatment of epithelial tissue diseases or conditions, or in the prevention or treatment of diseases or disorders associated with platelet aggregation.

BACKGROUND OF THE INVENTION

Epithelial tissues comprise a layer or layers of cells that cover free and enclosed surfaces throughout the body, including cutaneous, mucous, lumenal, serous, and glandular spaces. All epithelial layers contain two specialized domains: an apical domain that faces the mucosal (or lumenal) space and a basolateral membrane that faces the serosal (or ablumenal) space. Thus an important function of all epithelia is to provide an appropriate barrier function to separate and to control many physiological processes between these two spaces. In the lung, for example, the airways epithelia serve many functions, including providing a barrier between the lung mucosa and blood supply, to coordinate the hydration of the airways, to regulate blood-borne immune responses in the airway mucosa, and to clear the airways of toxins and pathogens. Epithelial cells are ubiquitous throughout the body, and are found in the entire respiratory and digestive tract, reproductive system and sensory organs (eye, ear, nose and skin). Epithelial cells have evolved to serve many homeostatic functions that are specific to their location throughout the body. One such specific function is found in the mucociliary clearance (MCC) system. Mucous secretions are normally removed via the MCC. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus. It is now known that nucleoside phosphates such as uridine 5'-triphosphate (UTP) modulate all of the components of the MCC system. First, UTP has been shown to increase both the rate and total amount of mucin secretion by goblet cells in vitro (M. Lethem, et al., *Am J. Respir. Cell Mol. Biol.* 9, 315-22 (1993)). Second, UTP has been shown to increase cilia beat frequency in human airway epithelial cells in vitro (D. Drutz, et al., *Drug Dev. Res.* 37(3), 185 (1996)). And third, UTP has been shown to increase Cl$^-$ secretion, and hence, water secretion from airway epithelial cells in vitro (S. Mason, et al., *Br. J. Pharmacol.* 103, 1649-56 (1991)). In addition, it is thought that the release of surfactant from Type II alveolar cells in response to UTP (Gobran, *Am. J. Physiol.* 267, L625-L633 (1994)) contributes to optimal functioning of the lungs and may assist in maximizing MCC. UTP has been shown to increase intracellular Ca$^{++}$ due to stimulation of phospholipase C by the P2Y$_2$ receptor (H. Brown, et al., *Mol. Pharmacol.* 40, 648-55 (1991)).

The retinal pigment epithelium (RPE) lies in the back of the vertebrate eye and forms a barrier that separates the retina from the choroidal blood supply. Although anatomically an epithelial tissue, the RPE also functions in a glial-like capacity in maintaining homeostatic retinal function. For example, a critical function of the RPE is to maintain and regulate the hydration of the subretinal space, the extracellular volume that exists between the retina and the RPE. (Marmor, pp. 3-12, in *The Retinal Pigment Epithelium*, Eds. M. F. Marmor and T. J. Wolfensberger, Oxford University Press, New York, (1998)) This function is achieved by the regulated transport of fluid, ions, and metabolites between the subretinal space and the choroidal blood supply. (Marmor, pp. 420-438, in *The Retinal Pigment Epithelium*, Eds. M. F. Marmor and T. J. Wolfensberger, Oxford University Press, New York, (1998); Pederson, pp. 1955-1968, in *Retina*, Ed. S. J. Ryan, Mosby, St. Louis, (1994)). Like all epithelia, the RPE contains two functionally and anatomically distinct membranes: an apical membrane that faces the retina, and a basolateral membrane that faces the choroidal blood supply. In the normal retina, fluid is absorbed across the RPE in the direction of the subretinal space to the choroid. This active absorption of fluid by the RPE, often referred to as the "RPE pump," plays a critical role in maintaining proper attachment of photoreceptors to the apical membrane of the RPE by pumping fluid out of the retinal spaces. (Marmor, pp. 1931-1954, in *Retina*, Ed. S. J. Ryan, Mosby, St. Louis, (1994); Hughes, et al., pp. xvii, 745, in *The Retinal Pigment Epithelium*, Eds. M. F. Marmor and T. J. Wolfensberger, Oxford University Press, New York, (1998)).

Glaucoma is a disease complex characterized primarily by an increase in intraocular pressure. Sufficiently high and persistent intraocular pressure may result in damage to the optic disc at the juncture of the optic nerve and retina, resulting in irreversible blindness. There are three types of glaucoma: primary, secondary, and congenital. Primary glaucoma is subdivided into narrow angle (acute congestive) and wide-angle (chronic simple) types, depending on the configuration of the angle of the anterior chamber where re-absorption of the aqueous humor occurs. Effects on the volumes of the various intraocular vascular beds, such as those of the iris and ciliary body and on the rate of secretion of the aqueous humor into the posterior chamber may contribute secondarily to the lowering of the pressure or, conversely, may produce a rise in pressure preceding the fall. In narrow angle glaucoma, the aqueous outflow is enhanced by freeing of the entrance to the trabecular space at the canal of Schlemm from blockade by the iris, as a result of the drug-induced contraction of the sphincter muscle of the iris. (Taylor, pp. 123-125, in *The Pharmacological Basis of Therapeutics*, 7$^{th}$ Ed, Eds., A. G. Gilman, L. S. Goodman, T. W. Rall, and F. Murad, MacMillan Publishing Company, New York, (1985))

In wide-angle, or chronic simple, glaucoma, the entry to the trabeculae is not physically obstructed; the trabeculae, a meshwork of pores of small diameter, lose their patency. Contraction of the sphincter muscle of the iris and the ciliary muscle enhances tone and alignment of the trabecular network to improve re-absorption and outflow of aqueous humor through the network to the canal of Schlemm (Watson, *Br. J. Opthalmol.* 56: 145-318 (1972); Schwartz, *N. Engl. J. Med.*, 290: 182-186 (1978); Kaufman, et al., Handbook of Experimental *Pharmacology* 69: 149-192 (1984)).

Human joints are lubricated by fluid secreted from synovial membranes, which line internal, non-articular joint surfaces. The lubricating properties of synovial fluid have been attributed to a surfactant consisting of surface active phospholipid (SAPL), the mucinous glycoprotein lubricin, hyaluronic acid (hyaluronan), and water. Hyaluronan is a critical constituent component of normal synovial fluid and an important contributor to joint homeostasis. Hyaluronan imparts anti-inflammatory and antinociceptive properties to normal synovial fluid and contributes to joint lubrication, buffering load transmission across articular surfaces and providing a continually replenished source of hyaluronan to articular tissues. Joint lubrication is compromised in osteoarthritis (OA).

Studies suggest that activation of P2Y receptors by extracellular nucleotides elicit responses from inflammatory cells (such as mast cells, eosinophil, leukocytes, neutrophils) consistent with a pro-inflammatory effect. Extracellular nucleotide-induced stimulation of leukocytes and subsequent adhesion to endothelium has been shown to play an important role in inflammatory diseases. Extracellular nucleotides stimulate P2Y receptor on human polymorphonuclear neutrophils (PMN) with the pharmacological profile of the $P2Y_2$ receptor.

Allergy is a state of hypersensitivity caused by exposure to a specific antigen (allergen) resulting in harmful immunologic reactions or subsequent exposures. The first encounter with an allergen sensitizes the body via the lymphocytes, resulting in IgE coating of mast cells and basophils. Subsequent exposure results in the development of the "early phase" of the allergic reaction and occurs within seconds or minutes of exposure to an allergen. The early phase is also known as the immediate hypersensitivity reaction. In the allergic reaction, hypersensitivity is a condition in a previously exposed person, in which tissue inflammation is caused by an immune reaction upon re-exposure to an allergen sensitizer. In half of occurrences, the allergic reaction develops into a "late phase," which occurs about 4 to 6 hours after the exposure. In the late phase reaction, tissues become red and swollen due to the collection of eosinophils, neutrophils, lymphocytes, and other cells.

Previous work has demonstrated the presence of P2Y receptors in glial and neuronal cells of the mature nervous system (Abbracchio and Burnstock, Jpn J. Pharmacol, 78:113-45, 1998). P2Y receptors belong to a class of G-protein coupled receptors (GPCR) that activate a variety of intracellular signaling pathways. Although features of P2Y receptor signaling in some cell types are known, the physiological roles of P2Y receptors in the nervous system are not well-characterized. In central, peripheral and sensory nervous systems, P2Y receptor activation profoundly affect glia, a cell type that plays important roles in nervous system development, function, and survival. Previous work has suggested a role for P2Y receptors in neurotransmission, neuronal-to-glial cell-cell signaling, alterations of gene expression, neuritogenesis, and interactions with growth factors in an additive or synergistic manner (Abbracchio and Burnstock, Jpn J Pharmacol, 78:113-45, 1998).

Hemostasis is the spontaneous process of stopping bleeding from damaged blood vessels. Precapillary vessels contract immediately when cut; within seconds, thrombocytes, or blood platelets, are bound to the exposed matrix of the injured vessel by a process called platelet adhesion. Platelets also stick to each other in a phenomenon known as platelet aggregation to form a platelet plug to stop bleeding quickly.

An intravascular thrombus results from a pathological disturbance of hemostasis. Platelet adhesion and aggregation are critical events in intravascular thrombosis. Activated under conditions of turbulent blood flow in diseased vessels or by the release of mediators from other circulating cells and damaged endothelial cells lining the vessel, platelets accumulate at a site of vessel injury and recruit further platelets into the developing thrombus. The thrombus can grow to sufficient size to block off arterial blood vessels. Thrombi can also form in areas of stasis or slow blood flow in veins. Venous thrombi can easily detach portions of themselves called emboli that travel through the circulatory system and can result in blockade of other vessels, such as pulmonary arteries. Thus, arterial thrombi cause serious disease by local blockade, whereas venous thrombi do so primarily by distant blockade, or embolization. These conditions include venous thrombosis, thrombophlebitis, arterial embolism, coronary and cerebral arterial thrombosis, unstable angina, myocardial infarction, stroke, cerebral embolism, kidney embolisms and pulmonary embolisms.

There is an unmet medical need for new therapeutic nucleotides that have good storage stability and/or in vivo stability that can be used for treating epithelial diseases, or for treating diseases or disorders associated with platelet aggregation with minimal side effects. Nucleotides, defined here as a nucleoside base with one or more phosphate groups attached at the furanosyl primary hydroxyl group, can act via receptors (e.g. P2Y), and ion channels (e.g. P2X). The therapeutic utility of nucleotides arises from their actions as either agonists or antagonists of receptor (P2) function. Two classes of therapeutic nucleotides have emerged recently-mononucleotides (e.g. nucleoside mono-, di-, and tri-phosphates) and dinucleotides (dinucleoside polyphosphates). Mononucleotides, such as uridine triphosphate and adenosine triphosphate (UTP and ATP) are potent ligands of P2 receptors (see U.S. Pat. Nos. 5,292,498 and 5,628,984). However these mononucleotides have poor chemical and metabolic stability making them less attractive as drug candidates due to required refrigeration and short in vivo half-life. Dinucleotides, such as diuridine tetraphosphate and diadenosine tretraphosphate ($Up_4U$ and $Ap_4A$), show an improvement in chemical and metabolic stability (Yerxa, et al. (Drugs of the Future, 24:759-769 (1999)), while retaining activity at various P2 receptors (see U.S. Pat. Nos. 5,635,160; 5,837,861; 5,900,407; 6,319,908; and 6,323,187).

Despite the therapeutic improvements made by the use of dinucleotides and their in vivo and storage stability, the difficulty and expense of their synthesis requires further investigation of new class of compounds.

SUMMARY OF THE INVENTION

The present invention is directed to compounds of mononucleoside phosphates of the general Formula I, or pharmaceutically acceptable salts thereof:

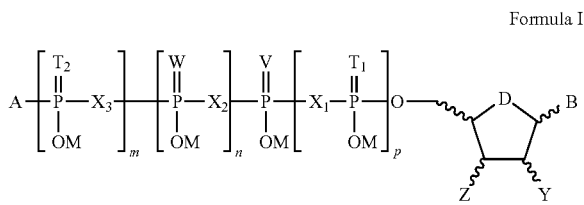

Formula I wherein;

A has a molecular weight of no more than about 1000 and is $OR_1$, $SR_1$, $NR_1R_2$, or $CR_1R_2R_3$ such that $R_1$, $R_2$, and $R_3$ are each independently hydrogen, alkyl, cycloalkyl, aryl, arylalkyl, phosphonate, or acylthioalkyl, with or without substituents or heteroatoms; or taken together to form a cycloalkyl or aryl ring, with or without substituents or heteroatoms, with the exception of $OR_1$ and $SR_1$ not being OH or SH; or a natural or non-natural amino acid, peptide, polypeptide, or other oligomer; or natural or non-natural steroid:

$X_1$, $X_2$, and $X_3$ are independently oxygen, methylene, monochloromethylene, dichloromethylene, monofluoromethylene, difluoromethylene, or imido;

$T_1$, $T_2$, W, and V are independently oxygen or sulfur;

m=0, 1 or 2;

n=0 or 1;

p=0, 1, or 2;

where the sum of m+n+p is from 0 to 5;

M=H or a pharmaceutically-acceptable inorganic or organic counter ion;

D=O or $CH_2$;

B is a purine or a pyrimidine residue according to general Formulae IV and V which is linked to the 1' position of the furanose or carbocycle via the 9- or 1-position of the base, respectively;

Y=H, OH, or $OR_4$;

Z=H, OH, or $OR_5$; with the proviso that Y and Z are not both H;

$R_4$ and $R_5$ are residues which are linked directly to the 2' and/or 3' oxygens of the furanose or carbocycle via a carbon atom according to Formula II, or linked directly to the two 2' and 3' oxygens of the furanose or carbocycle via a common carbon atom according to Formula III.

The present invention is also directed to a method of preventing, or treating epithelial diseases or conditions; such diseases include respiratory diseases, eye diseases, vaginal and cervical dryness, gastrointestinal tract diseases, inflammatory and allergic diseases, such as chronic bronchitis, cystic fibrosis, sinusitis, lung cancer, otitis media, retinal detachment, retinal edema, dry mouth, gastroesophageal reflux disease (GERD), constipation, glaucoma associated with elevated intraocular pressure, retinal degenerative diseases; corneal edema, allergic conjunctivitis, ocular surface inflammation, allergic rhinitis. A further aspect of the present invention is directed to a method of preventing or treating diseases of the joint; such diseases include osteoarthritis and rheumatoid arthritis. Yet a further aspect of the present invention is directed to a method of preventing or treating diseases associated with platelet aggregation and thrombosis in humans and other mammals.

The method comprises administering to a subject a pharmaceutical composition comprising a therapeutically effective amount of a nucleotide of Formula I, wherein said amount is effective to prevent or treat a specified disease.

The present invention is directed to a method of treating epithelial diseases or conditions associated therewith, the method comprises:

(a) identifying a mammal suffering from epithelial tissue diseases or conditions; and (b) applying a composition comprising a compound of Formula I in an amount effective to treat epithelial tissue diseases or conditions.

The present invention is also directed to a method of preventing epithelial tissue diseases or conditions associated therewith, the method comprises:

(a) applying to a mammal at risk for epithelial tissue diseases a composition comprising a compound of Formula I in an amount effective to prevent the incidence of epithelial tissue diseases, and (b) determining whether such disease or condition developed.

The invention also provides novel pharmaceutical compositions comprising compounds of Formula I in a pharmaceutically acceptable carrier.

DETAILED DESCRIPTION OF THE INVENTION

Definitions

When present, unless otherwise specified, the following terms are generally defined as, but are not limited to, the following:

Alkyl groups are from 1 to 12 carbons inclusively, either straight chained or branched, with or without heteroatoms, are more preferably from 1 to 8 carbons inclusively, and most preferably 1 to 6 carbons inclusively.

Alkenyl groups are from 1 to 12 carbons inclusively, either straight or branched containing at least one double bond but may contain more than one double bond, with or without heteroatoms.

Alkynyl groups are from 1 to 12 carbons inclusively, either straight or branched containing at least one triple bond but may contain more than one triple bond, and additionally may contain one or more double bonded moieties, with or without heteroatoms.

Cycloalkyl groups are from 3 to 12 carbons inclusively, more preferably from 3 to 10 carbons inclusively, and most preferably 3 to 6 carbons inclusively, with or without heteroatoms.

Cycloalkenyl groups are from 4 to 12 carbons inclusively containing at least one double bond, and with or without heteroatoms.

Aralkyl groups are from 1 to 8 carbons inclusively in the alkyl portion, are more preferably from 1 to 6 carbons inclusively in the alkyl portion, and most preferably are 1 to 4 carbons inclusively in the alkyl portion; in addition to the alkyl definition above, the alkyl portion of an aralkyl group can include one or more positions of unsaturation such as a double bond or a triple bond in the chain when the chain includes two or more carbon atoms; the alkyl portion of an aralkyl group can also include one or more heteroatoms and/or substituents; the aryl portion of an aralkyl group can be a monocyclic or polycyclic moiety from 3 to 8 carbons inclusively per ring in the aryl portion, more preferably from 4 to 6 carbons inclusively per ring, and most preferably 5 to 6 carbons inclusively per ring; the aryl portion of an aralkyl group can also bear one or more substituents and/or heteroatoms.

Aryl groups are either monocyclic or polycyclic, are from 3 to 8 carbons inclusively per ring, are more preferably from 4 to 6 carbons inclusively per ring, and are most preferably 5 to 6 carbons inclusively per ring; aryl groups can also bear substituents and/or heteroatoms.

Heteroaralkyl groups are from 1 to 8 carbons inclusively in the alkyl portion, are more preferably from 1 to 6 carbons inclusively in the alkyl portion, and most preferably are 1 to 4 carbons inclusively in the alkyl portion; in addition to the alkyl definition above, the alkyl portion of a heteroaralkyl group can include one or more positions of unsaturation such as a double bond or a triple bond in the chain when the chain includes two or more carbon atoms; the alkyl portion of a heteroaralkyl group can also include one or more heteroatoms and/or substituents; the heteroaryl portion of a heteroaralkyl group can be a monocyclic or polycyclic moiety from 3 to 8 carbons inclusively per ring in the heteroaryl portion and containing from 1 to 4 heteroatoms inclusively per ring, more preferably from 4 to 6 carbons inclusively per ring, and most preferably 5 to 6 carbons inclusively per ring; the heteroaryl portion of an heteroaralkyl group can also bear one or more substituents and/or heteroatoms.

Heteroaryl groups are either monocyclic or polycyclic, contain from 1 to 4 heteroatoms inclusively per ring, are from 3 to 8 atoms inclusively per ring, are more preferably from 4 to 6 atoms inclusively per ring, and are most preferably 5 to 6 atoms inclusively per ring; heteroaryl groups can also bear substituents and/or heteroatoms.

Substituents on the foregoing groups can be, but are not limited to, hydroxy, nitro, methoxy, fluoro, chloro, bromo, iodo, methyl, ethyl, propyl, butyl, thioalkyl, alkoxy, carboxyl, carboxamido, alkylsulfonyl, alkylsulfonylamino, sulfonamido, cyano, amino, substituted amino, trifluoromethyl, trifluoromethoxy, phenyl, pyridyl, imidazolyl, cyclopropyl, cyclopentyl, and cyclohexyl; and preferred heteroatoms are oxygen, nitrogen, and sulfur.

A desired substituent on a chain or ring (in place of a hydrogen at a position) is one selected from the given alkyl, aryl, halogen, aralkyl, carboxy, alkoxycarbonyl, hydroxyl, acyloxy, alkoxy, aryloxy or aralkoxy classes or from other classes, which provides a compound with good-to-excellent $P2Y_{12}$ receptor-binding properties, but which does not yield a compound with undesirable properties like chemical instability in a formulation, or one with levels of toxicity that are not well-tolerated by a treated mammal, or especially, not well-tolerated by a human.

Diastereomers are stereoisomers (isomers of identical constitution but differing three-dimensional architecture), which do not bear a mirror-image relation to each other.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. When a molecule of the present invention contains a basic moiety such as amino, an acid addition salt can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, mesylic, adipic, lactic, tartaric, salicylic, methanesulfonic, 2-hydroxyethanesulfonic, toluenesulfonic, benzenesulfonic, camphorsulfonic, and ethanesulfonic acids. For salts of the phosphate chain (or other acidic moieties, such as a carboxylic acid), the pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$). Preferred counterions are monovalent ions such as $NH_4^+$, sodium, lithium, potassium, chloride, bromide, bisulfate, and mesylate, with sodium, potassium, chloride and mesylate being most preferred due to ease of manufacture, stability, and physiological tolerance.

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toluene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion, which possess the stated activity.

The applicants have unexpectedly discovered that the chemical and biological stability of a dinucleotide can be achieved by a mononucleotide that has been modified by attaching a degradation-resistant substituent A on the terminal phosphate of a nucleoside polyphosphate. By attaching a degradation-resistant substituent, the stability from degradation matches or exceeds that of certain dinucleotides. The pharmacological activity of the mononucleotide is unexpectedly maintained, and in some instances enhanced, when this degradation-resistant substituent is present. In the worst case, this new mononucleotide molecule will only have half of the efficacy of the comparable dinucleotide, but in many instances that lower efficacy is completely acceptable, particularly when viewing the benefits of the new molecule.

In many instances the degradation-resistant substituent can have its own pharmacological activity, different from those of nucleotides. Further, these new molecules, due to the degradation-resistant substituent A, in many instances have the benefits of 1) ease in manufacture, e.g. superior physical chemical characteristics which lend to simplified purification schemes; 2) reduced costs, as nearly all of the substituents described as A are less costly than nucleosides; 3) fewer stereochemistry concerns as few substituents are as stereochemically complex as nucleosides; 4) enhanced pharmacokinetic properties as non-nucleoside substituents can possess a myriad of differing characteristics; and/or 5) enhanced chemical stability as nucleosides are inherently less stable than most organic molecules.

Important criteria for these new molecules are stability and that the degradation-resistant substituent does not interfere with the activity of the nucleotide. This means that the degradation-resistant substituent is no larger than 1000 Daltons, preferably less than 500, and that the substituent does not adversely affect pharmacological activity or toxicity or alternatively is beneficial. Further, this degradation-resistant substituent on the nucleotide must not react with other nucleotide molecules or with other components of the pharmaceutical formulation in ways that would detrimentally modify the nucleotide's pharmacological activity. This means that this degradation-resistant substituent must be reasonably stable within a pharmaceutical formulation.

The present invention provides compounds of Formula I, and/or tautomers thereof, and/or pharmaceutically-acceptable salts, and/or solvates, and/or hydrates thereof.

The present invention also provides methods of preventing or treating epithelial diseases or conditions. The present invention further provides methods of treating disorders associated with platelet aggregation. The method comprises administering to a subject a pharmaceutical composition comprising a therapeutically effective amount of the compound of general Formula I and pharmaceutically acceptable salts, hydrates, or solvates thereof.

Formula I

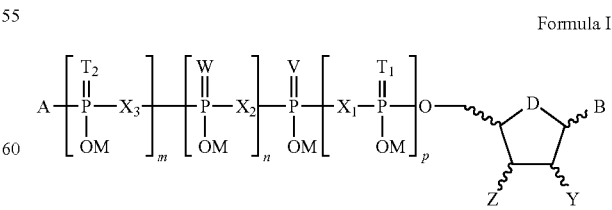

wherein:
A is a covalently bound degradation-resistant substituent that has a molecular weight of no more than about 1000 and is $OR_1$, $SR_1$, $NR_1R_2$, or $CR_1R_2R_3$ such that $R_1$, $R_2$, and $R_3$ are independently hydrogen, alkyl, cycloalkyl, aryl, arylalkyl, phosphonate, or acylthioalkyl, with or without substituents or heteroatoms, or taken together to form a cycloalkyl or aryl ring, with or without substituents or heteroatoms, with the exception of $OR_1$, and $SR_1$ not being OH or SH; or a natural or non-natural amino acid, peptide, polypeptide, or other oligomer; or natural or non-natural steroid. In other words, A is a covalently bound substituent having a maximum molecular weight of 1000 and selected from the group consisting of a natural or non-natural amino acid, a peptide, a polypeptide, an oligonucleotide, a polynucleotide, a natural or non-natural steroid. A is preferably a hydroxylated alkyl group (e.g. glycerol, cholesterol); is an amino acid (e.g. phenylalanine, serine, tyrosine) having 3 to 50 carbon atoms; is amino or mono- or disubstituted amino, where the substituents are alkyl, cycloalkyl, aralkyl, aryl, substituted aralkyl, or substituted aryl having 3 to 50 carbon atoms and which may also contain heteroatoms (e.g. S, N, O).

$X_1$, $X_2$, and $X_3$ are independently oxygen, methylene, monochloromethylene, dichloromethylene, monofluoromethylene, difluoromethylene, or imido;

$T_1$, $T_2$, W, and V are independently oxygen or sulfur;

m=0, 1 or 2;

n=0 or 1;

p=0, 1, or 2;

where the sum of m+n+p is from 0 to 5 (preferably 2 or 3);

M=H or a pharmaceutically-acceptable inorganic or organic counter ion;

D=O or $CH_2$;

B is a purine or a pyrimidine residue according to general Formulae IV and V which is linked to the 1' position of the furanose or carbocycle via the 9- or 1-position of the base, respectively;

Y=H, OH, or $OR_4$;

Z=H, OH, or $OR_5$; with the proviso that Y and Z are not both H;

$R_4$ and $R_5$ are residues which are linked directly to the 2' and/or 3' oxygens of the furanose or carbocycle via a carbon atom according to Formula II, or linked directly to the two 2' and 3' oxygens of the furanose or carbocycle via a common carbon atom according to Formula III.

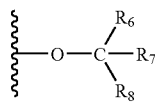

Formula II wherein:

O is the corresponding 2' and/or 3' oxygen of the furanose or carbocycle;

$R_6$, $R_7$, and $R_8$ are H, an alkyl, cycloalkyl, aralkyl, aryl, substituted aralkyl, or substituted aryl, such that the moiety defined according to Formula II is an ether; or $R_6$ and $R_7$ are H, an alkyl, cycloalkyl, aralkyl, aryl, substituted aralkyl, or substituted aryl, and $R_8$ is alkoxy, cycloalkoxy, aralkyloxy, aryloxy, substituted aralkyloxy, or substituted aryloxy such that the moiety defined according to formula II is an acyclic acetal or ketal; or $R_6$ and $R_7$ are taken together as oxygen or sulfur doubly bonded to C, and $R_8$ is alkyl, cycloalkyl, aralkyl, aryl, substituted aralkyl, or substituted aryl, such that the moiety defined according to Formula II is an ester or thioester; or $R_6$ and $R_7$ are taken together as oxygen or sulfur doubly bonded to C, and $R_8$ is amino or mono- or disubstituted amino, where the substituents are alkyl, cycloalkyl, aralkyl, aryl, substituted aralkyl, or substituted aryl, such that the moiety according to Formula II is a carbamate or thiocarbamate; or $R_6$ and $R_7$ are taken together as oxygen or sulfur doubly bonded to C, and $R_8$ is alkoxy, cycloalkoxy, aralkyloxy, aryloxy, substituted aralkyloxy, or substituted aryloxy, such that the moiety according to Formula II is a carbonate or thiocarbonate; or $R_8$ is not present and $R_6$ and $R_7$ are taken together as oxygen or sulfur doubly bonded to C and both the 2' and 3' oxygens of the furanose are directly bound to C to form a cyclical carbonate or thiocarbonate;

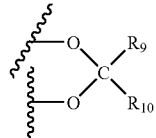

Formula III wherein:

O is the 2' and 3' oxygens of the furanose or carbocycle; and the 2' and 3' oxygens of the furanose or carbocycle are linked by a common carbon atom (C) to form a cyclical acetal, cyclical ketal, or cyclical orthoester;

for cyclical acetals and ketals, $R_9$ and $R_{10}$ are independently hydrogen, alkyl, cycloalkyl, aralkyl, aryl, substituted aralkyl, substituted aryl or can be joined together to form a homocyclic or heterocyclic ring composed of 3 to 8 atoms, preferably 3 to 6 atoms; for cyclical orthoesters, $R_9$ is hydrogen, alkyl, cycloalkyl, aralkyl, aryl, substituted aralkyl, or substituted aryl, $R_{10}$ is alkyloxy, cycloalkyloxy, aralkyloxy, aryloxy, substituted aralkyloxy, or substituted aryloxy;

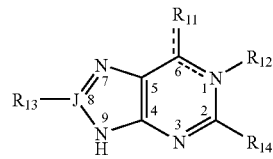

Formula IV

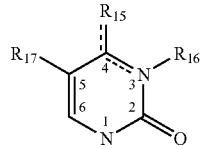

Formula V wherein:

$R_{11}$ and $R_{15}$ are hydroxy, oxo, amino, mercapto, alkylthio, arylthio, alkyloxy, aryloxy, alkylamino, cycloalkylamino, aralkylamino, arylamino, diaralkylamino, diarylamino, or dialkylamino, where the alkyl groups are optionally linked to form a heterocycle; or $R_{11}$ and $R_{15}$ are acylamino, provided that they incorporate an amino residue from the C-6 position of the purine or the C-4 position of the pyrimidine; or when $R_{11}$ in a purine or $R_{15}$ in a pyrimidine has as its first atom nitrogen, $R_{11}$ and $R_{12}$ or $R_{15}$ and $R_{16}$ are taken together to form a 5-membered fused imidazole ring (etheno compounds), optionally substituted on the etheno ring with alkyl, cycloalkyl, aralkyl, or aryl moieties, as described for $R_6$-$R_{10}$ above; or when $R_{15}$ in a pyrimidine has as its first atom oxygen, $R_{15}$ and $R_{17}$ are taken together to form a 5-membered dihydrofuran ring, optionally substituted on the dihydrofuran ring with alkyl, cycloalkyl, aralkyl, or aryl moieties, as described for $R_6$-$R_{10}$ above;

J is carbon or nitrogen, with the provision that when nitrogen, $R_{13}$ is not present;

$R_{12}$ is hydrogen, O (adenine 1-oxide derivatives) or is absent (adenine derivatives);

$R_{16}$ is hydrogen, or acyl (e.g. acetyl, benzoyl, phenylacyl, with or without substituents);

$R_{13}$ is hydrogen, alkyl, bromo, azido, alkylamino, arylamino or aralkylamino, alkoxy, aryloxy or aralkyloxy, alkylthio, arythio or aralkylthio, or $\omega$-E($C_{1-6}$ alkyl)G-, wherein E and G are independently amino, mercapto, hydroxy or carboxyl;

$R_{14}$ is hydrogen, halo, amino, monosubstituted amino, disubstituted amino, alkylthio, arylthio, or aralkylthio, where the substituent on sulfur contains up to a maximum of 20 carbon atoms, with or without unsaturation;

$R_{17}$ is hydrogen, methyl, alkyl, halo, alkyl, alkenyl, substituted alkenyl, alkynyl, or substituted alkynyl.

Compounds according to Formulae IV and V where $R_{11}$ or $R_{15}$ is acylamino for the most part fall within the scope of Formula VI:

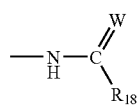

Formula VI wherein:

NH is the amino residue at the C-6 position in a purine or the amino residue at the C-4 position in a pyrimidine;

W is oxygen or sulfur;

$R_{18}$ is amino or mono- or disubstituted amino such that the moiety according to Formula VI is a urea or thiourea; or $R_{18}$ is alkoxy, aralkyloxy, aryloxy, substituted aralkyloxy, or substituted aryloxy, such that the moiety according to Formula VI is a carbamate or thiocarbamate; or $R_{18}$ is alkyl, cycloalkyl, aralkyl, or aryl, with or without substituents or heteroatoms, such that the moiety according to Formula VI is an amide; with definitions of alkyl, cycloalkyl, aralkyl, or aryl groups as previously defined for comparable groups in $R_6$ to $R_{10}$.

One general synthetic scheme for the synthesis of compounds of the invention employs activation of a nucleoside mono-, di-, or triphosphate with an activating agent such as carbonyldiimidazole, phosphorous oxychloride, etc. and subsequent reaction with a nucleophile, Nu (e.g. $R_1OH$, $R_1SH$, $NHR_1R_2$, etc.), to the activated terminal phosphate moiety. B is any purine or pyrimidine, natural or synthetic. The product is shown as a ribofuranosyl sugar in the β-D configuration for illustration purposes only, and is not intended to be limiting in scope.

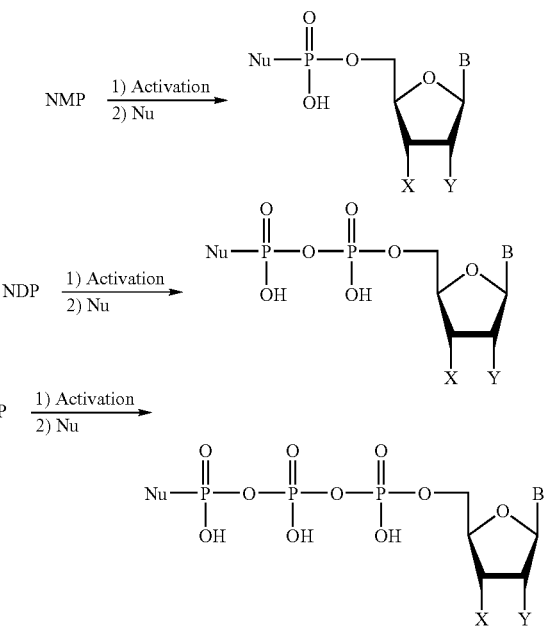

Alternatively, compounds of the invention can be made according to the scheme below in which a nucleoside mono-, di-, or triphosphate is added to an electrophile, El (e.g. activated sugar, activated carboxylic acid, activated carbon, activated amino acid, etc.). B is any purine or pyrimidine, natural or synthetic. The product is shown as a ribofuranosyl sugar in the β-D configuration for illustration purposes only, and is not intended to be limiting in scope.

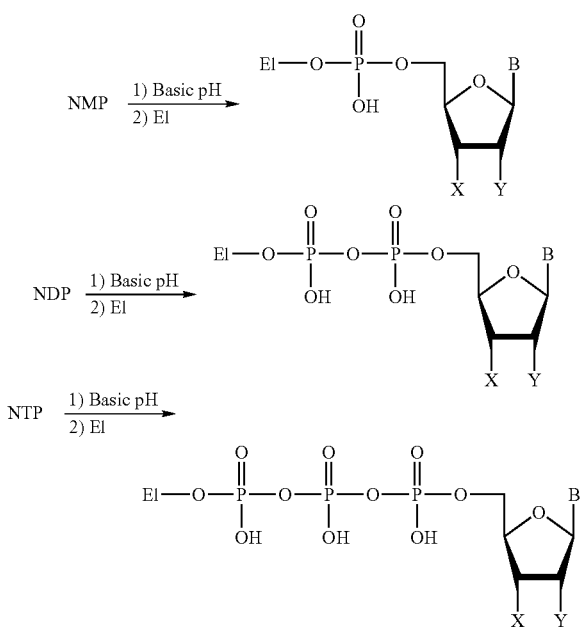

Another general synthetic scheme is to couple a phosphonic acid $(HO)_2P(O)CR_1R_2R_3$ with a nucleoside or nucleotide, employing an agent such as dicyclohexylcarbodiimide, carbonyldiimidazole etc. to effect the condensation.

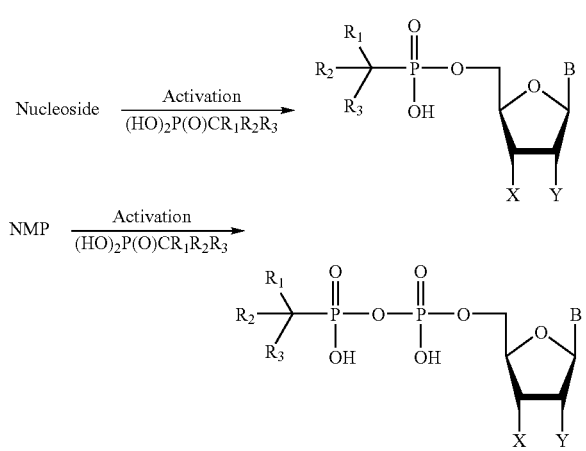

5'-nucleoside mono-, di-, tri-, and tetraphosphates can be obtained from commercial sources or can be synthesized from the nucleoside using a variety of phosphorylation reactions, which can be found in the chemical literature. Nucleoside mono- and diphosphates so obtained can be reacted with carbonyldiimidazole, dicyclohexylcarbodiimide or other suitable activating reagents, and coupled with a variety of nucleophiles to install unique substituents on the terminal phosphate. Activation of nucleoside triphosphates with dicyclohexylcarbodiimide gives a cyclical trimetaphosphate as the activated species, which can be advantageously ring opened with nucleophiles, to give substituents on the terminal (γ) phosphate of the triphosphate. If the cyclical trimetaphosphate is opened with reagents containing phosphate as the nucleophile, nucleoside 5'-tetraphosphates are produced with novel moieties on the terminal (δ) phosphate. Alternately, these same phosphate nucleophiles can be reacted with the previously described activated nucleoside mono- and diphosphates, giving di- and triphosphates (respectively) that fall within the scope of the present invention.

As mentioned above, the role of the phosphate chain can be reversed such that the terminal phosphate of the chain can serve as a nucleophile towards electrophilic reagents. Examples of electrophilic reagents include alkyl and aralkyl halides and sulfonates, activated acyl compounds, activated phosphorous compounds, and the like.

For the compounds of the present invention which are modified on the nucleic acid base or furanose in addition to the phosphate chain, the modifications can be made at the level of the nucleoside, followed by phosphorylation and condensation with nucleophiles as previously described, or the reactions can be carried out directly on the preassembled nucleotide. In general Formula I, the substituents at Y and Z can be ethers, esters, acyclic acetals and ketals, carbamates, or carbonates, which are generally described by Formula II. Ethers can be prepared by reacting a hydroxyl group in a nucleoside or nucleotide with an activated form of an appropriate alkyl or aralkyl, such as an alkyl/aralkyl halide, alkyl/aralkyl sulfonate and the like, usually in the presence of an organic or inorganic base. Esters can be readily prepared by reacting a hydroxyl group in a nucleoside or nucleotide with an activated form of an appropriate organic acid, such as an acid halide or acid anhydride in the presence of an organic or inorganic base. Alternately, use of a suitable coupling reagent such as dicyclohexylcarbodiimide, 1,1'-carbonyldiimidazole and the like to activate the organic acid can be used to achieve the same result. Acyclic acetals and ketals can be prepared by the reaction between a single hydroxyl in a nucleoside or nucleotide with aldehydes or ketones (respectively) or their chemical equivalents, under acidic conditions.

Carbamates or thiocarbamates can be most conveniently prepared by reaction of a hydroxyl group in a nucleoside or nucleotide with any of a number of commercially available isocyanates or isothiocyanates, respectively, in an inert solvent. Carbonates or thiocarbonates can be synthesized by reacting the hydroxyl groups in a nucleoside or nucleotide with an appropriate haloformate in the presence of an organic or inorganic base.

In the general Formula I, the substituents at Y and Z, when taken together, can be taken to mean acetals, ketals or orthoesters, as described by Formula III. Acetals and ketals can be readily prepared by reaction of the neighboring 2' and 3' hydroxyl groups in an appropriate nucleoside or nucleotide with an aldehyde or ketone, respectively, or their chemical equivalents, in the presence of an acid catalyst. Typical acids include trichloroacetic, p-toluenesulfonic, and methanesulfonic employed in catalytic amounts, in conjunction with inert solvents. Alternately, weaker organic acids such as formic can be used as both the catalyst and solvent for the reaction.

Cyclical orthoesters can be prepared by reaction of the neighboring 2' and 3' hydroxyl groups in a nucleoside or nucleotide with an acylic orthoester, in the presence of an acid.

When the nucleoside or nucleotide to be derivatized is a purine that contains a 6-amino functionality or is a pyrimidine that contains a 4-amino functionality, it can be converted to the respective urea or thiourea, as described by general formula VI. This can be accomplished by treatment with isocyanates or isothiocyanates, respectively, as was previously described for carbamates or thiocarbamates of the 2' or 3' hydroxyls. Reactions of these amino groups with isocyanates or isothiocyanates can be carried out in the presence of the unprotected hydroxyl groups, by appropriate manipulation of the stoichiometry of the reaction.

Those skilled in the art will recognize various synthetic methodologies, which can be employed to prepare non-toxic pharmaceutically acceptable salts and acylated prodrugs of the compounds of the present invention. Methods of preparing these from the compound of Formula I include passing an aqueous solution through a column of ion exchange resin in the desired cation form, thus converting the compound to the desired salt form. If the desired end product is a sodium salt, such as A on uridine tetraphosphate tetrasodium salt, the starting material (an ammonium or other salt) is passed through a DOW 50H+ column to protonate the compound and generate the free acid. This protonated compound is collected in an aqueous solution of sodium hydroxide which forms the sodium salt.

As is typical for nucleotide chemistry, the reactions which give rise to compounds of the present invention usually end with several products being formed, owing to multiple reactive sites in these molecules. When multiple products are obtained, these can be separated by the use of preparative reverse phase high performance liquid chromatography (HPLC). Particularly advantageous is the use of C18 or phenyl reverse phase columns, in conjunction with gradients that start with ammonium acetate buffer and end with methanol. Following chromatography, the products are isolated by evaporation of the solvent, followed by lyophilization.

While separation of multiple products can be done by HPLC, another strategy is to use nucleosides or nucleotides which contain only a single functionality which is reactive under the conditions being employed. This can be accomplished by the use of protecting groups to block side reactions at other positions in the molecule. This can be done at the level of the nucleoside prior to phosphorylation and coupling of the phosphate chain with a nucleophile, or at the level of the nucleotide.

The second aspect of the present invention provides methods of preventing or treating epithelial diseases or conditions. The method comprises administering to a subject a pharmaceutical composition comprising a therapeutically effective amount of the compound of general Formula I and pharmaceutically acceptable salts thereof.

In one embodiment, the present invention is directed to a method of preventing or treating diseases or conditions associated with enhancing clearance of secretions in the respiratory tract by increasing the hydration of retained mucus secretions, stimulating the production of mucins, and increasing ciliary beat frequency. Prevention or treatment of diseases that could benefit from enhancing clearance of secretions by increasing the hydration of retained mucus secretions, stimulating the production of mucins, and increasing ciliary beat frequency are chronic obstructive pulmonary diseases such as chronic bronchitis, acute bronchitis, acute exacerbations of chronic bronchitis, PCD, cystic fibrosis, as well as prevention of pneumonia due to immobility. Furthermore, because of their general ability to clear retained mucus secretions and stimulate ciliary beat frequency, the compounds of the present invention are also useful in the treatment of acute and chronic sinusitis and otitis media in mammals, including humans. By enhancing secretion clearance, the compounds are useful as protection before or after exposure to inhaled biological warfare agents. They can also be used to enhance lung imaging by clearing secretions from the lungs prior to obtaining the image, for detection of lung disease through an increase in sputum production. The method comprises administering to a subject a pharmaceutical composition comprising a therapeutic effective amount of a compound of general Formula I or pharmaceutically acceptable salts, hydrates, or solvates thereof, wherein said amount is effective to hydrate the mucosal membranes of the respiratory tract.

In another embodiment, the present invention is directed to a method of stimulating cervical and vaginal secretions in a subject in need of such treatment. The method of the present invention can be used to increase cervical and vaginal secretions for any reason, including, but not limited to, treatment of vaginal dryness and/or treatment of vulvar pain. Vaginal dryness is associated with but not limited to menopause, childbirth, breastfeeding, chemotherapy or radiotherapy, diabetes mellitus, Sjögren's syndrome, Ehlers-Danlos syndrome, systemic sclerosis and other systemic autoimmune diseases, hysterectomy, urogenital surgery, psychosomatic disorders, anxiety, psychosexual problems, and pharmacological drug-related side effects. The method comprises administering to a subject a pharmaceutical composition comprising a therapeutic effective amount of a compound of general Formula I or pharmaceutically acceptable salts, hydrates, or solvates thereof, wherein said amount is effective to hydrate the mucosal membranes in the vaginal and cervical tracts.

In another embodiment, the present invention is directed to a method of regulating mucus secretions and fluid transport in the gastrointestinal system of a mammal, including humans. There are many situations where it is therapeutically desirable to increase the amount of mucin secretion, bicarbonate secretions, and/or degree of hydration in gastrointestinal systems. When the mucosal barrier is impaired in the digestive tract, it results in diseases such as dry mouth, gastro-esophageal reflux disease, peptic ulcer, inflammatory bowel disease, etc. Abnormal fluid and electrolytic transport in the lower gastrointestinal tract results in disorders such as constipation and diarrhea. Proper regulation of fluid and electrolytic absorption and secretion at appropriate regions along the gastrointestinal system is required for normal digestive function. The invention provides a method of regulating mucus/mucin secretions, and fluid transport in the gastrointestinal tract. The invention provides a method for treating gastrointestinal disease in which the mucosal barrier of the gastrointestinal system is impaired. Gastrointestinal diseases suitable for treatment by this invention include diseases or disorders affecting the buccal cavity (primary salivary), esophagus, stomach, small intestine, large intestine, rectum and ancillary organs such as pancreas, liver and gall bladder. The invention additionally provides a method for correcting disorders of fluid secretion or absorption in the gastrointestinal. For example, dry mouth, mouth ulcer, gum disease, esophageal reflux disease, peptic ulcer, inflammatory bowel disease (ulcerative colitis and Crohn's disease), diarrhea and constipation can be treated by the present method. In addition, gastrointestinal problems associated with cystic fibrosis diseases such as dry mucin and decreased absorption of nutrient by epithelial cells in the gastrointestinal tract can also be treated by the present method. In addition, gastrointestinal problems caused by cancer and chemotherapy can also be treated by this method. The method comprises administering to a subject a pharmaceutical composition comprising a therapeutic effective amount of a compound of general Formula I or pharmaceutically acceptable salts, hydrates, or solvates thereof, wherein said amount is effective to hydrate the mucosal membranes of the gastrointestinal tract.

The present invention is also directed to a method of preventing or treating diseases or conditions associated with the ocular surface. Such conditions of the ocular surface include, but not limited to, dry eye disease and ocular surface inflammation. This method for treatment of the causes of dry eye disease is through stimulating tear secretions from conjunctival tissues. The present invention is also directed to a method of preventing or treating ocular surface inflammation as well as other eye related conditions such as keratoconjunctivitis sicca (KCS), age-related dry eye, Stevens-Johnson syndrome, Sjögren's syndrome; ocular cicatrical, pemphigoid; blepharitis; corneal injury; infection; Reilly-Day syndrome; congenital alacrima; nutritional disorders; pharmacologic side-effects; eye stress and glandular and tissue; smog exposure; smoke exposure; dry air caused by insufficient hydration of the ocular surface.

Still further indications where the compounds of the invention are useful are for the treatment of other diseases or conditions associated with the mammalian eye. Degenerative retinopathies generally affect two neuronal cell populations in the retina: the photoreceptors and ganglion cells. Glial cells in the mature nervous systems provide trophic support to neurons and are therefore a viable cellular target to effect neuronal preservation and survival in a variety of neurodegenerative conditions. This invention is also directed to a method for treating diseases or conditions associated with retinal degeneration, removal of fluid in retinal detachment and retinal edema as well as treatment of ocular hypertension. Retinal degeneration is often an endpoint of a variety of ocular and systemic diseases and environmental conditions, such as macular degeneration, glaucoma, retinitis pigmentosa, optic nerve degeneration, optic neuritis, chronic metabolic diseases (diabetic retinopathy) neurotoxins, ischemia and physical trauma.

The methods and compositions disclosed in the present invention can be used to stimulate removal of extraneous intra-retinal or subretinal fluid for any reason, including, but not limited to, primary and adjunctive treatments of rhegmatogenous retinal detachment, serous retinal detachment, all forms of cystoid macular edema (uveitis, post-surgical, central and branch vein occlusion, and inherited retinal diseases such as retinitis pigmentosa), and all forms of retinal and macular edema (proliferative and non-proliferative, exudative age-related macular degeneration, and retinopathy of prematurity). The method comprises administering to a subject a pharmaceutical composition comprising a therapeutic effective amount of a compound of Formula I or a pharmaceutically acceptable salt thereof, wherein said amount is effective in said treatment.

Still further indications where the compounds of the invention are useful in the management and/or treatment of primary glaucoma, which consists of two types: narrow angle or acute congestive and wide angle or chronic simple glaucoma. Yet another embodiment of the present invention is the management and/or treatment of secondary glaucoma.

The present invention provides a method of treating and/or managing glaucoma, by facilitating the outflow of fluid from the eye and thereby reduces the accumulation of said fluid contributing to increased intraocular pressure characteristic of glaucoma. The method comprises co-administration to a subject, an effective dose of a pharmaceutical composition comprising a purinergic receptor ligand, with or without therapeutic and adjuvant agents commonly used to treat or manage glaucoma.

The present invention is also directed to a method of stimulating the secretion of synovial fluid, mucins, hyaluronic acid, and/or surface-active phospholipids, and thereby enhancing joint lubrication, using a nucleotide in patients in need of such treatment. The present invention provides a method of enhancing joint lubrication comprising administering to a subject in need of such treatment a compound of general Formula I or pharmaceutically acceptable salts, hydrates, or solvates thereof, in an amount therapeutically effective to enhance joint lubrication. The present invention provides a method of treating osteoarthritis comprising administering to a subject in need of such treatment a compound of general Formula I or pharmaceutically acceptable salts, hydrates, or solvates thereof, in an amount therapeutically effective to treat osteoarthritis.

The present invention is also directed to a method preventing and/or reversing the symptoms and manifestations of inflammatory diseases, and hence a method of treating inflammation.

Still further indications where the compounds of the invention are useful are for a method of preventing and/or reversing the symptoms and manifestations of allergic reactions and thus a method of treating allergies.

This method comprises administering to a subject in need thereof a pharmacological composition comprising a compound of Formula I or a pharmaceutically acceptable salt, solvates, or hydrates thereof, in an amount effective to treat, prevent, and/or reverse the symptoms and manifestations of inflammatory diseases, together with a pharmaceutically acceptable carrier.

The present invention is also directed to a method of preventing or treating diseases or conditions associated with platelet aggregation. "Platelet aggregation", as used herein, means all processes that lead to the aggregation of the platelets such as adhesion, shape change, degranulation, activation of intracellular signaling pathways, expression of proteins in the membrane surface of the platelet such as receptors and other signaling proteins. The method comprises the steps of administering to a subject a compound of Formula (I), or a salt, solvate, or hydrate thereof, and a pharmaceutically acceptable carrier, in an amount effective to inhibit platelet aggregation.

The diseases or conditions associated with platelet aggregation are disorders or procedures characterized by thrombosis, primary arterial thrombotic complications of atherosclerotic disease, thrombotic complications of interventions of atherosclerotic disease, thrombotic complications of surgical or mechanical damage, mechanically-induced platelet activation, shunt occlusion, thrombosis secondary to vascular damage and inflammation, indications with a diffuse thrombotic/platelet consumption component, venous thrombosis, coronary arterial thrombosis, pathological effects of atherosclerosis and arteriosclerosis, platelet aggregation and clot formation in blood and blood products during storage, chronic or acute states of hyper-aggregability, reocclusion of an artery or vein following fibrinolytic therapy, platelet adhesion associated with extracorporeal circulation, thrombotic complications associated with thrombolytic therapy, thrombotic complications associated with coronary and other angioplasty, or thrombotic complications associated with coronary artery bypass procedures.

The disorders or procedures associated with thrombosis are unstable angina, coronary angioplasty, or myocardial infarction; said primary arterial thrombotic complications of atherosclerosis are thrombotic stroke, peripheral vascular disease, or myocardial infarction without thrombolysis; said thrombotic complications of interventions of atherosclerotic disease are angioplasty, endarterectomy, stent placement, coronary or other vascular graft surgery; said thrombotic complications of surgical or mechanical damage are associated with tissue salvage following surgical or accidental trauma, reconstructive surgery including skin flaps, or reductive surgery; said mechanically-induced platelet activation is caused by cardiopulmonary bypass resulting in microthromboembolism and storage of blood products; said shunt occlusion is renal dialysis and plasmapheresis; said thromboses secondary to vascular damage and inflammation are vasculitis, arteritis, glomerulonephritis or organ graft rejection; said indications with a diffuse thrombotic/platelet consumption component are disseminated intravascular coagulation, thrombotic thrombocytopenic purpura, hemolytic uremic syndrome, heparin-induced thrombocytopenia, or pre-eclampsia/eclampsia; said venous thrombosis are deep vein thrombosis, veno-occlusive disease, hematological conditions, or migraine; and said coronary arterial thrombosis is associated with unstable angina, coronary angioplasty or acute myocardial infarction.

The pathological effects of atherosclerosis and arteriosclerosis are arteriosclerosis, acute myocardial infarction, chronic stable angina, unstable angina, transient ischemic attacks, strokes, peripheral vascular disease, arterial thrombosis, preeclampsia, embolism, restenosis or abrupt closure following angioplasty, carotid endarterectomy, or anastomosis of vascular grafts; said chronic or acute states of hyper-aggregability is caused by DIC, septicemia, surgical or infectious shock, post-operative trauma, post-partum trauma, cardiopulmonary bypass surgery, incompatible blood transfusion, abruptio placenta, thrombotic thrombocytopenic purpura, snake venom or immune diseases.

The compounds of the present invention are useful in treating diseases or conditions associated with platelet activation and/or aggregation produced by the contact of blood with an artificial device. In one embodiment, the artificial device is a paracorporeal artificial lung and an extracorporeal membrane oxigenation device. In another embodiment, the artificial device is an internal implantable artificial heart. In another embodiment, the artificial device is an apheresis instrument used to remove or isolate a specific component of the blood, and returning the remaining blood components to the donor. In yet another embodiment, the artificial device is a hemodialysis instrument.

The compounds of the present invention are useful in vitro to inhibit the aggregation of platelets in blood and blood products, e.g. for storage, or for ex vivo manipulations such as in diagnostic or research use. In such applications, the compounds are administered to the blood or blood product.

In a preferred embodiment, the compounds are used in the treatment of unstable angina, coronary angioplasty and myocardial infarction.

In another preferred embodiment, the compounds are useful as adjunctive therapy in the prevention or treatment of thrombotic disorders, such as coronary arterial thrombosis during the management of unstable angina, coronary angioplasty and acute myocardial infarction, i.e. perithrombolysis. The compounds are administered in combination with other antiplatelet and/or anticoagulant drugs such as heparin, aspirin, GP IIb/IIIa antagonists, or thrombin inhibitors.

This invention further provides a method for inhibiting the reocclusion of an artery or vein following fibrinolytic therapy, which comprises administering to a subject a compound of Formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

Compounds of the present invention can be administered systemically to target sites in a subject in need such that a target dose in the range of $10^{-1}$ to $10^{-6}$ M is achieved and preferably in the range of $10^{-2}$ to $10^{-4}$ M.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile indictable preparation can be a sterile indictable solution or suspension in a non-toxic acceptable diligent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anhydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Intravitreal delivery can include single or multiple intravitreal injections, or via an implantable intravitreal device that releases the compound in a sustained capacity. Intravitreal delivery can also include delivery during surgical manipulations as either an adjunct to the intraocular irrigation solution or applied directly to the vitreous during the surgical procedure.

The present invention also provides novel formulation compositions of matter. The compositions are pharmaceutically acceptable formulation comprising compounds of Formula I of high purity, and/or in a pharmaceutically acceptable carrier. The pharmaceutically acceptable carrier can be selected by those skilled in the art using conventional criteria. The pharmaceutically acceptable carrier include, but are not limited to, saline and aqueous electrolyte solutions, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

Preferred compounds of the present invention comprise compounds of Formula I wherein A has a molecular weight of no more than about 1000 and is $OR_1$, $SR_1$, $NR_1R_2$, or $CR_1R_2R_3$ such that $R_1$, $R_2$, and $R_3$ are independently hydrogen, $C_{1-30}$ alkyl, $C_{3-8}$ cycloalkyl, aryl, arylalkyl, phosphonate, or acylthioalkyl, with or without substituents or heteroatoms; or taken together to form a cycloalkyl or aryl ring, with or without substituents or heteroatoms with the exception of $OR_1$, and $SR_1$ not being OH or SH; or a natural or non-natural amino acid, peptide, polypeptide, or other oligomer; or natural or non-natural steroid: More preferably A is a hydroxylated alkyl group (e.g. glycerol, cholesterol); is an amino acid (e.g. phenylalanine, serine, tyrosine) having 3 to 50 carbon atoms; is amino or mono- or disubstituted amino, where the substituents are alkyl, cycloalkyl, aralkyl, aryl, substituted aralkyl, or substituted aryl having 3 to 20 carbon atoms and which may also contain heteroatoms (e.g. S, N, O) with 3 to 15 atoms being most preferred.

In one embodiment, A is $CR_1R_2R_3$, wherein $R_1$, $R_2$, and $R_3$ are independently hydrogen, alkyl, cycloalkyl, aryl, arylalkyl, phosphonate, or acylthioalkyl with or without substituents or heteroatoms; or taken together to form a cycloalkyl or aryl ring, with or without substituents or heteroatoms.

Preferably, $CR_1R_2R_3$ is an alkyl chain of 1-4 carbon atoms, with or without substituents or heteroatoms; or $CR_1R_2R_3$ is a saturated or unsaturated ring of 5 or 6 atoms, with or without heteroatoms or substituents, and with or without a linker of from 1 to 3 atoms between said ring and the phosphorous atom. When substituents are present, they are preferably charged, either acidic (for example, a carboxylic acid) or basic (for example, an amino group).

In one embodiment, $X_1$, $X_2$, and $X_3$ are oxygen, dichloromethylene or difluoromethylene; with oxygen being most preferred. In preferred compounds of the compositions of the present invention, $T_1$, $T_2$, W, and V of Formula I are independently oxygen or sulfur. More preferably $T_1$ and $T_2$, are sulfur or oxygen, and W and V oxygen, respectively; with $T_1$, $T_2$, W, and V being oxygen being most preferred. In preferred compounds of the compositions of the present invention, the sum of m+n+p of Formula is from 1 to 4. More preferably, the sum of m+n+p of Formula is 2 or 3, with 3 being most preferred. In preferred compounds of the present invention, M is lithium, sodium or potassium; an alkaline earth metal salt such as magnesium or calcium; or an ammonium or tetraalkyl ammonium salt, i.e., $NX_4^+$ (wherein X is $C_{1-4}$). More preferably M is sodium, potassium, or tetraalkyl ammonium; with sodium being most preferred. In preferred compounds of the present invention, D is oxygen.

In one embodiment, both Y and Z are OH. In another embodiment, Y is $OR_4$ and Z is $OR_5$.

In one embodiment, $R_4$ and $R_5$ are linked directly to the 2' and/or 3' oxygens of the furanose or carbocycle via a carbon atom according to Formula II, $R_6$ and $R_7$ together is oxygen, and $R_8$ is mono- or di-substituted amino. In a preferred embodiment, $R_4$ and $R_5$ are linked directly to the two 2' and 3' oxygens of the furanose or carbocycle via a common carbon atom according to Formula III, $R_9$ is H or aralkyl, and $R_{10}$ is aralkyl.

When B is a purine, it is preferably adenosine or hypoxanthine. Alternatively, $R_{11}$ is alkylamino or acylamino, $R_{12}$ is H, $R_{13}$ is H or halogen, $R_{14}$ is H, halogen, thioalkyl, or thioaralkyl. More preferably $R_{13}$ is H, $R_{14}$ is H or thioalkyl, When B is a pyrimidine, it is preferably uridine or cytidine. Alternatively, $R_{15}$ is O, S, amino, or substituted amino, $R_{16}$ is H; or $R_{15}$ and $R_{16}$ are taken together to form a substituted 5-membered imidazole ring, $R_{17}$ is H, halogen, alkyl, or substituted alkynyl, and $R_{18}$ is aralkyloxy. More preferably, $R_{15}$ is O, S, or amino or $R_{15}$ and $R_{16}$ taken together to form a substituted 5-membered imidazole ring, and $R_{17}$ is H, halogen, alkyl, or substituted alkynyl; with $R_{15}$ is O and $R_{17}$ is H being most preferred.

A preferred formula for the compound of the present invention is Formula Ia:

Formula Ia $$A\!\left[\!\begin{array}{c}W\\\|\\P-X_2\\|\\OM\end{array}\!\right]_n\!\left[\!\begin{array}{c}V\\\|\\P-X_1\\|\\OM\end{array}\!\right]\!\left[\!\begin{array}{c}T_1\\\|\\P-O\\|\\OM\end{array}\!\right]_p\!\!\begin{array}{c}H\quad H\\\diagup\!\!-\!\!D\!\!-\!\!\diagdown\\Z\quad Y\end{array}\!\!B$$

wherein the variable groups have the definitions as above.

A is preferably O-alkyl, O-cycloalkyl, O-aryl, S-alkyl, S-aryl, N-alkyl, N-cycloalkyl, or C-alkyl;

$X_1$, $X_2$, and $X_3$ are preferably oxygen;

$T_1$, $T_2$, W, and V are preferably oxygen; preferably, the sum of m+n+p is from 1 to 4; more preferably 2 or 3;

M is preferably H or an alkali metal; more preferably every M is a sodium or a potassium counter ion;

D is preferably oxygen;

B is preferably selected from the group consisting of uracil, cytosine, thymine, imidazo[1,2-c]pyrimidin-5(6H)-one {ethenocytosine}, 2-phenyl-imidazo[1,2-c]pyrimidin-5(6H)-one {phenylethenocytosine}, 5-iodouracil, 5-iodocytosine, 4-thiouracil, and 5-phenylethynyluracil; and Y and Z are both preferably OH.

In preferred embodiments, the variable groups in Formula Ia have the following definitions:

A is O-alkyl, O-cycloalkyl, O-aryl, S-alkyl, S-aryl, N-alkyl, N-cycloalkyl, or C-alkyl;

$X_1$, $X_2$, and $X_3$ are oxygen;

$T_1$, $T_2$, W, and V are oxygen;

the sum of m+n+p is from 1 to 4; more preferably 2 or 3;

M is H or an alkali metal; more preferably every M is a sodium or a potassium counter ion;

D is oxygen;

B is selected from the group consisting of adenine, hypoxanthine, and cytosine; and Y and Z are respectively $OR_4$ and $OR_5$, where they fall under the definition of Formula III.

The following compounds, within the scope of the present invention, are deemed particularly useful:

Structures 1-36 exemplify pyrimidine diphosphates where $A=OR_1$:

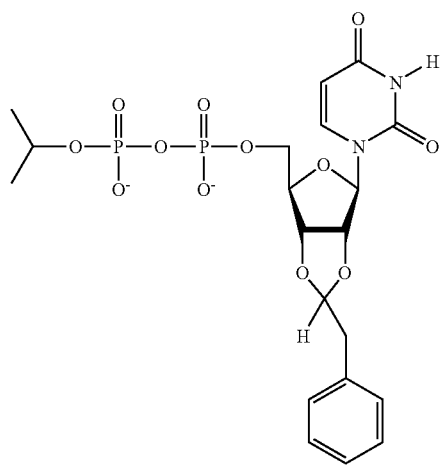

1

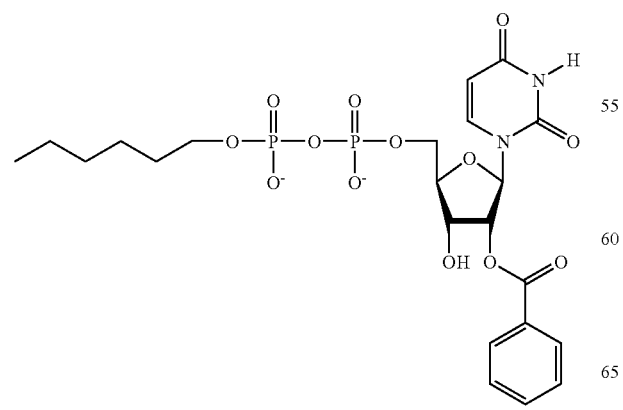

2

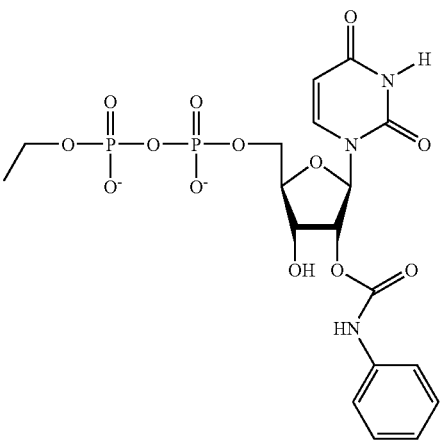

3

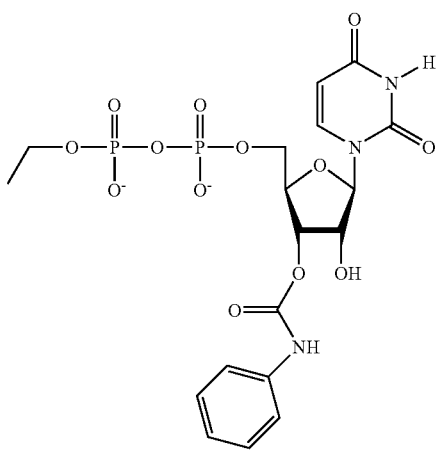

4

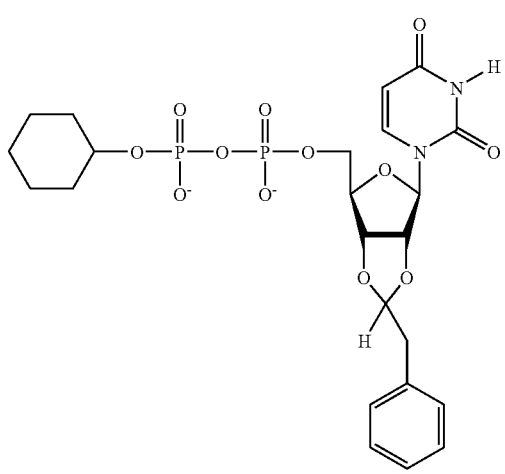

5

-continued
6
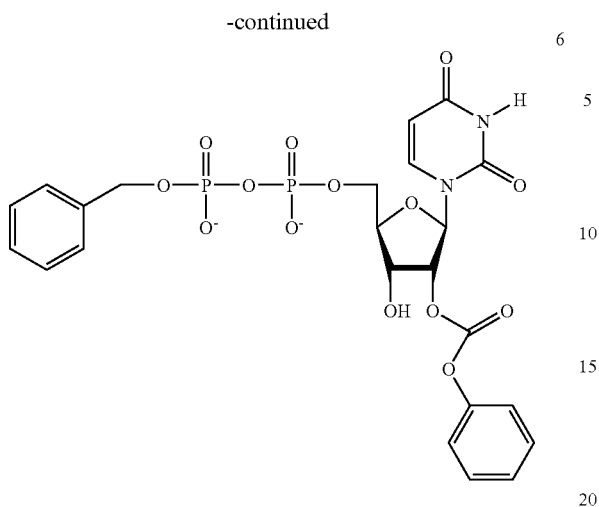
9
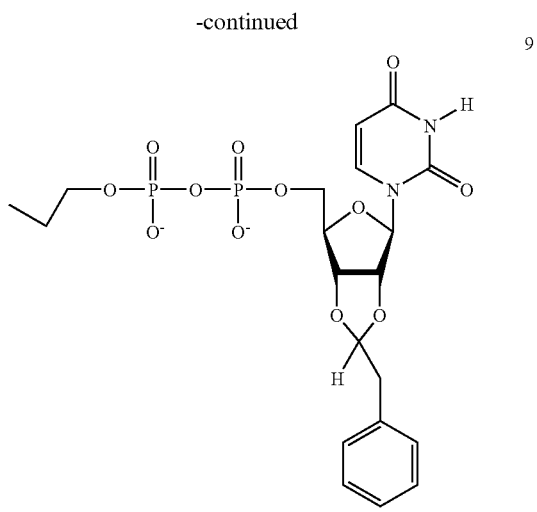
7
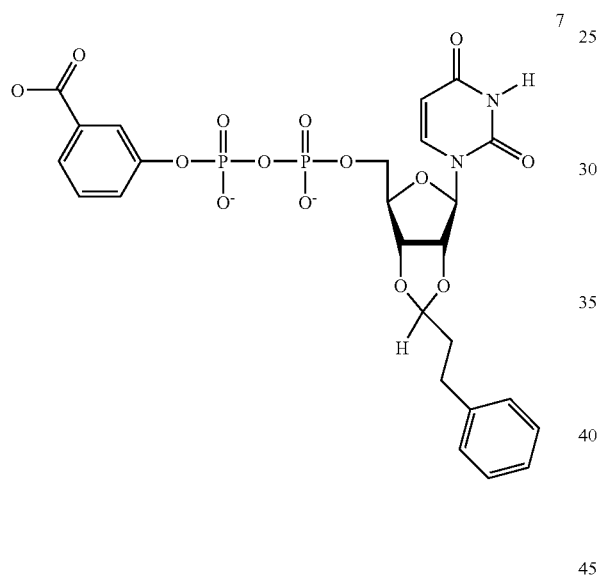
10
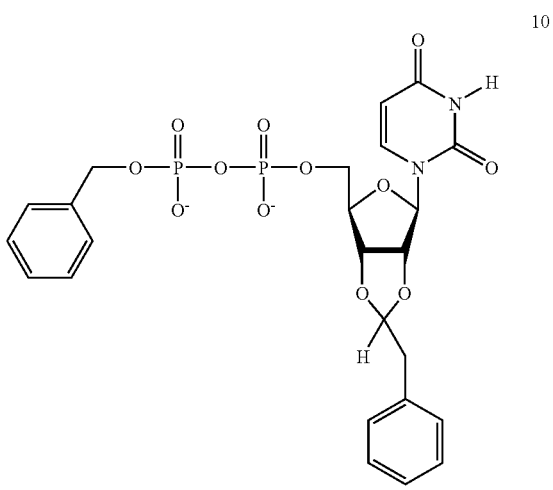
8
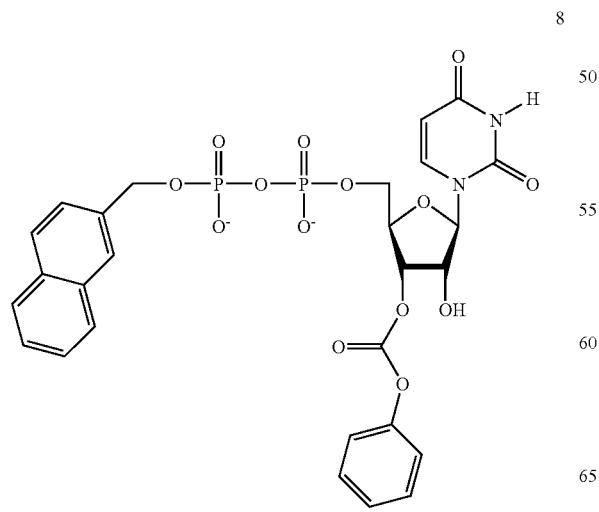
11
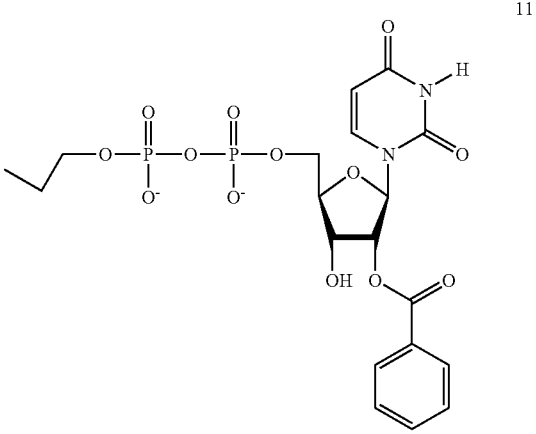

-continued
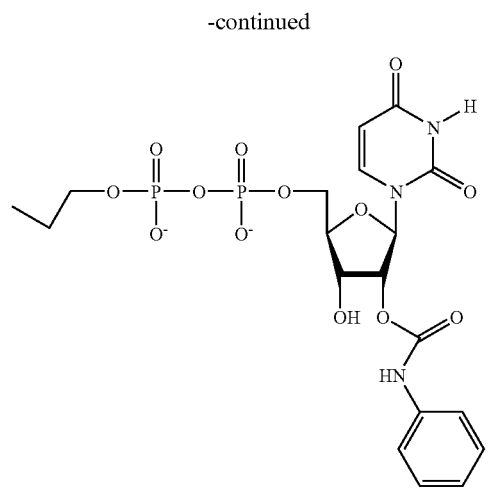
12
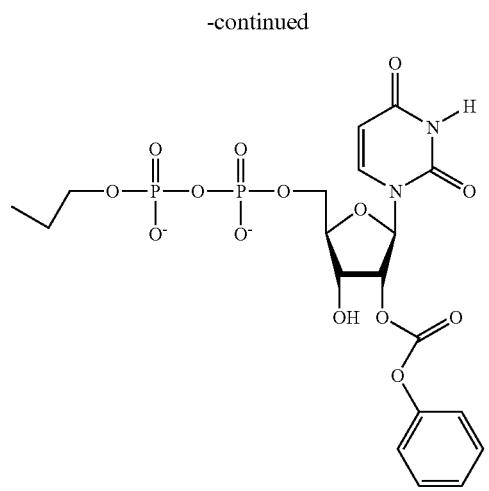
15
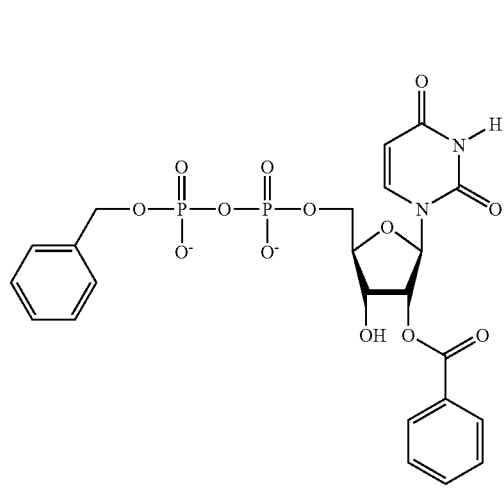
13
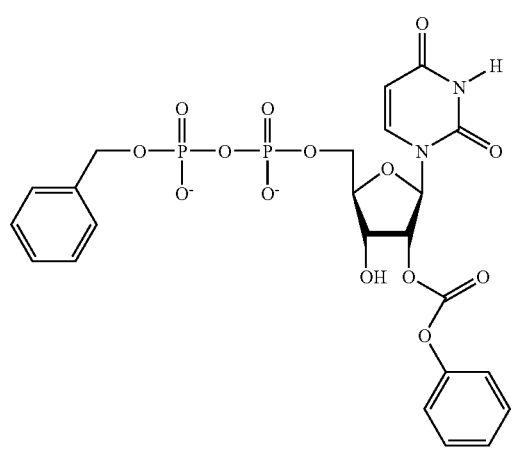
16
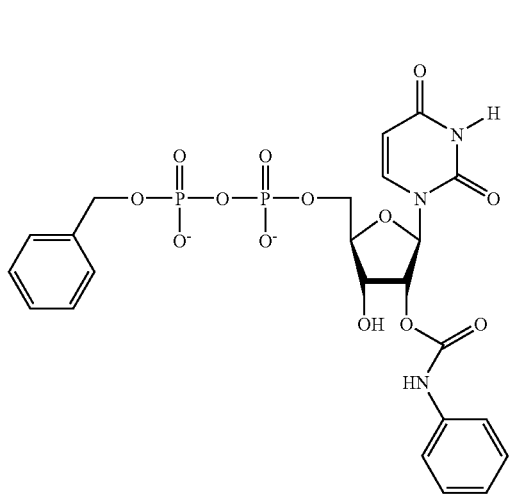
14
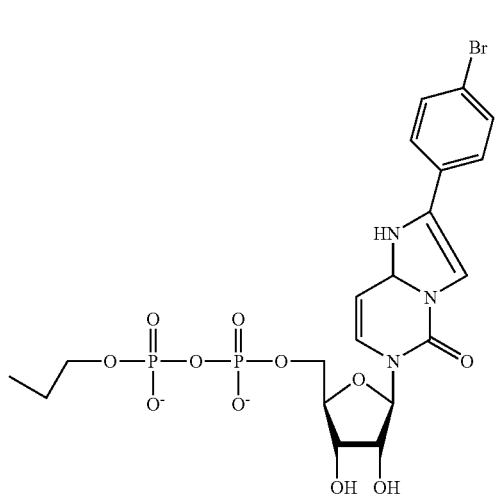
17

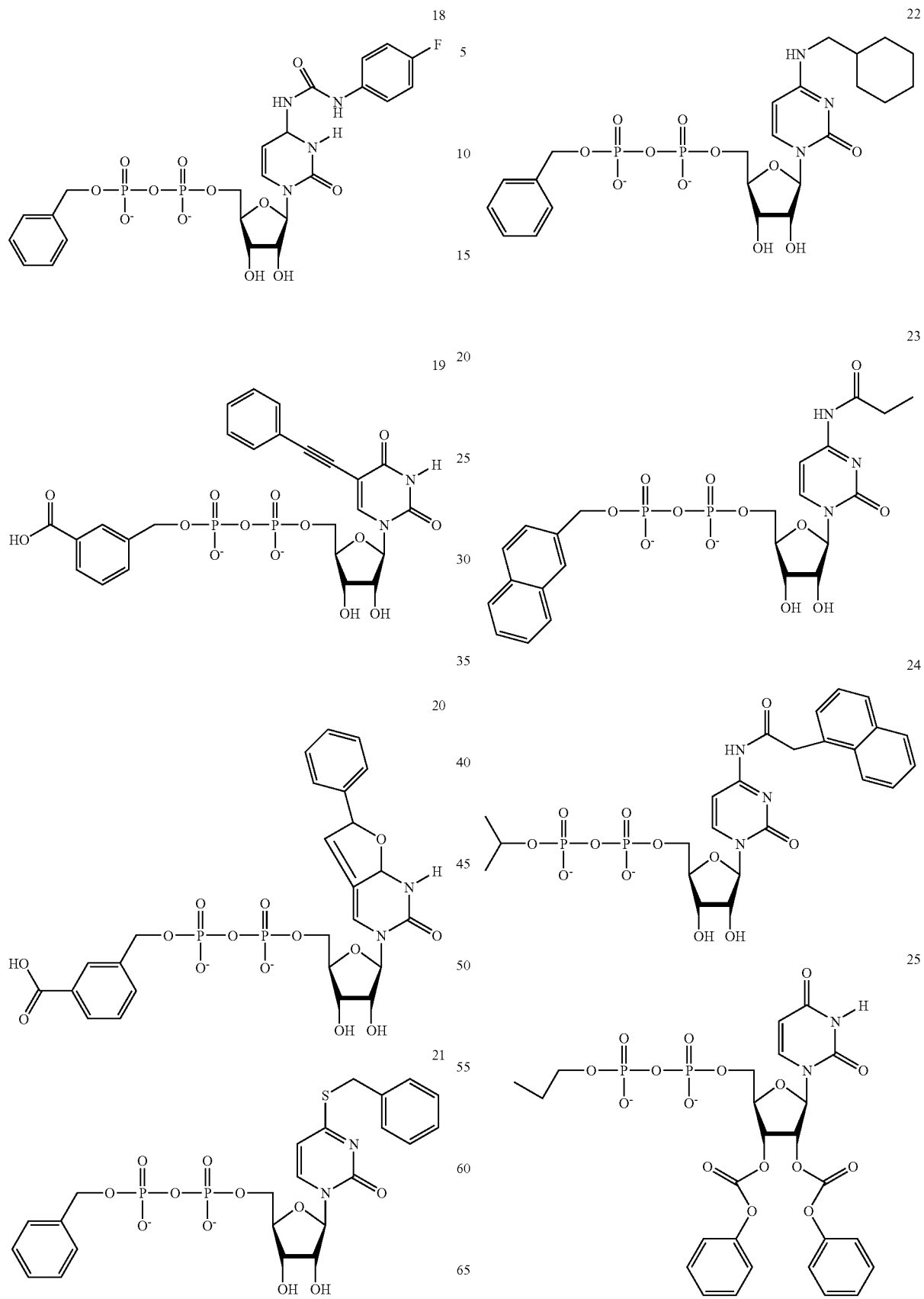

31
26
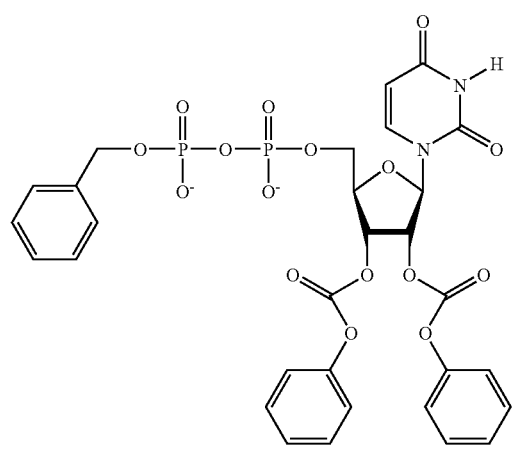
27
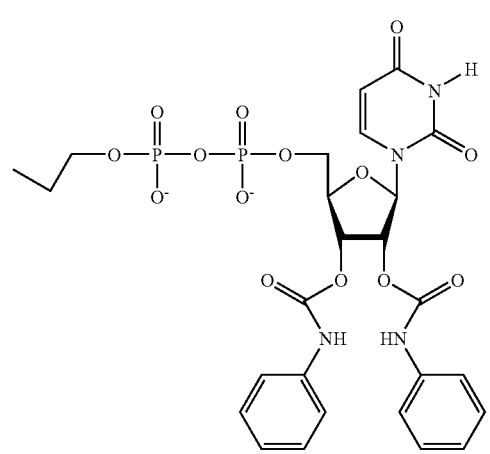
28
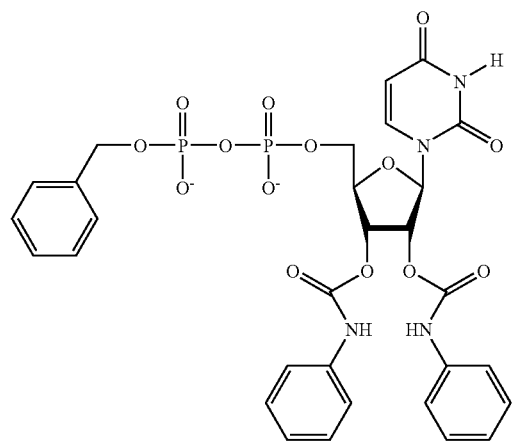
32
29
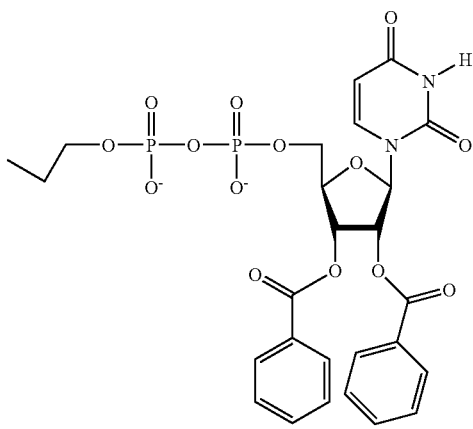
30
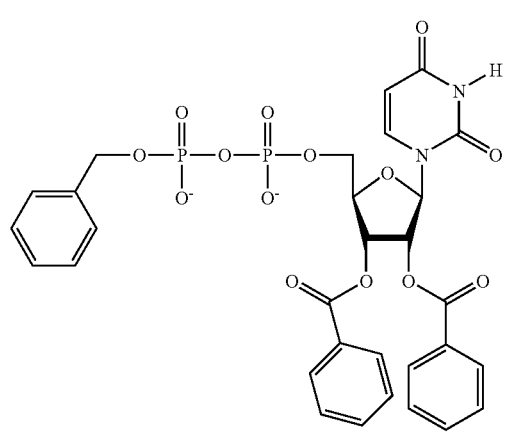
31
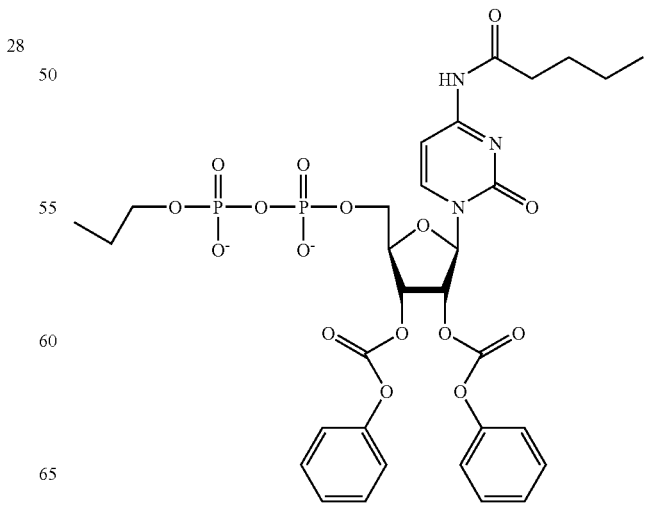

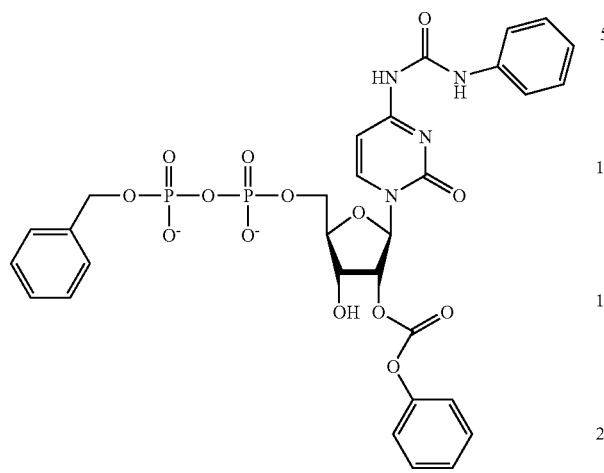
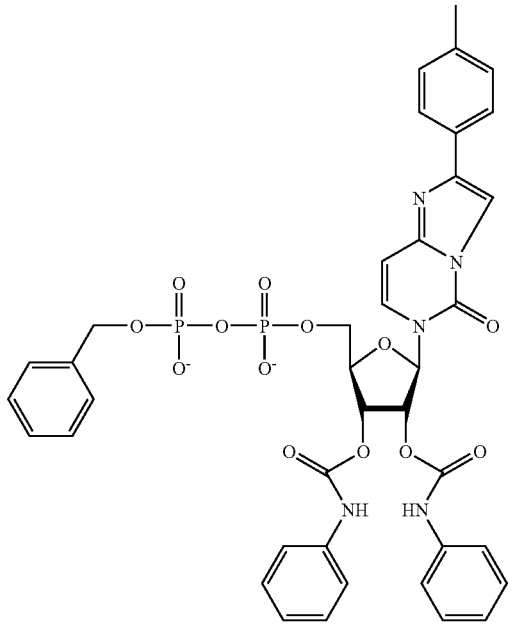
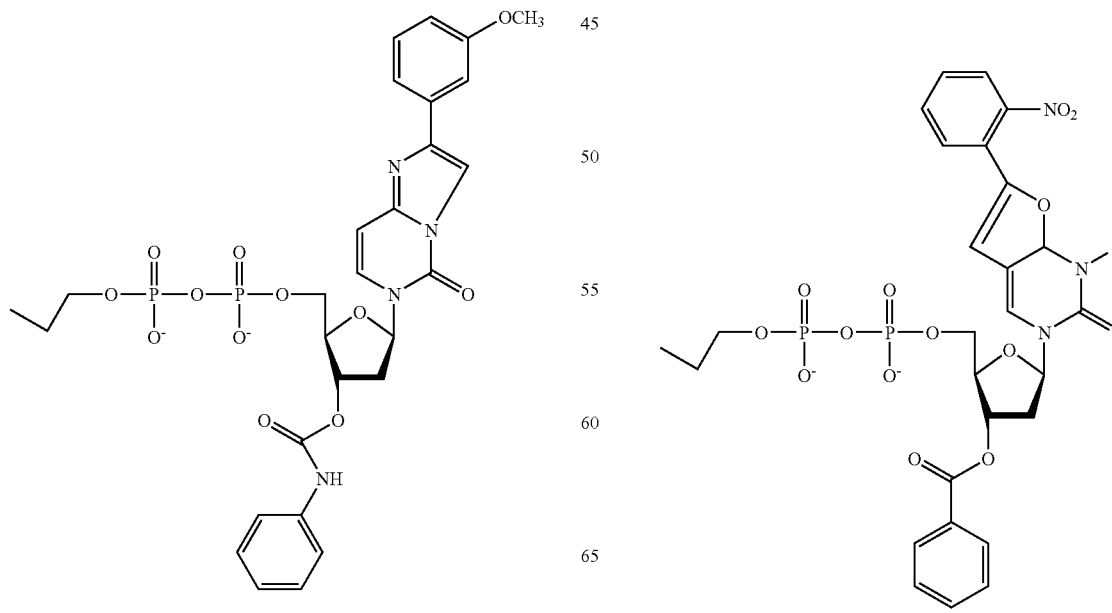

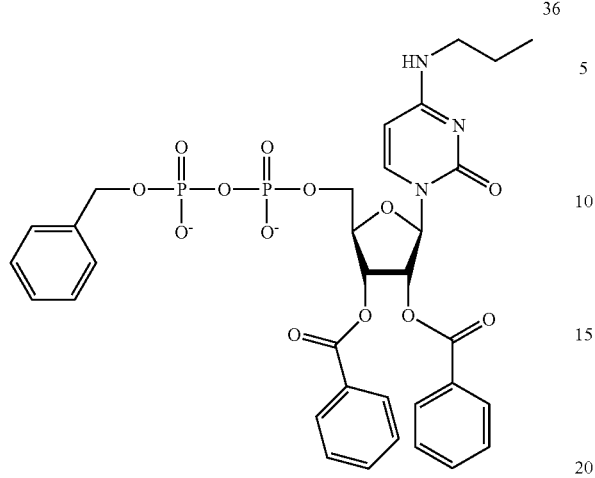
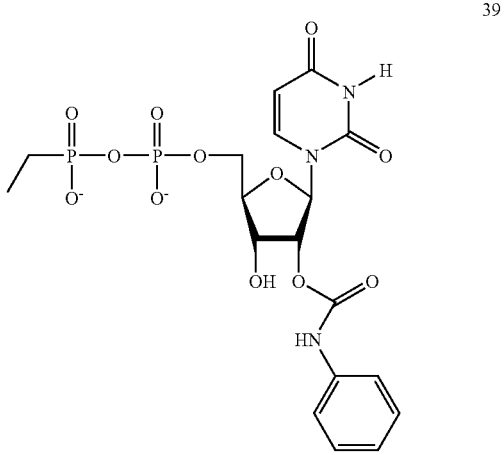
Structures 37-72 exemplify pyrimidine diphosphates where $A=CR_1R_2R_3$:
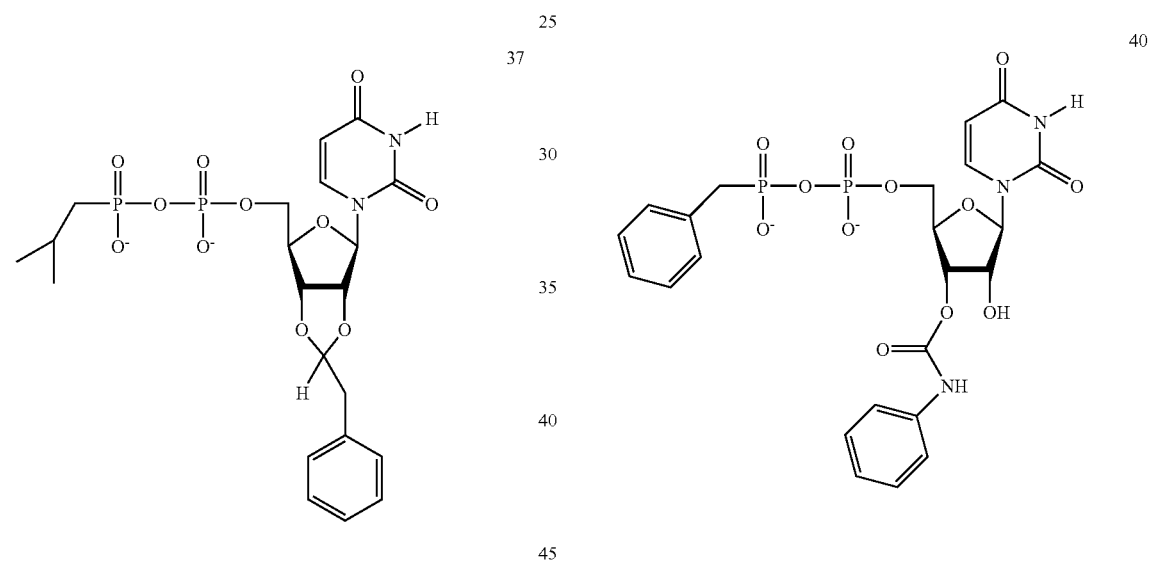
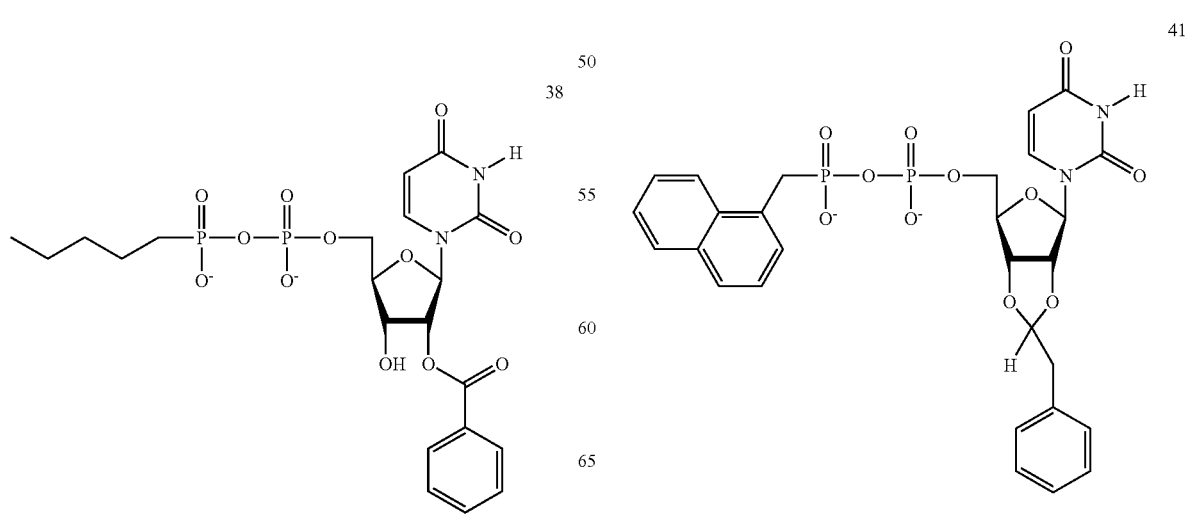

-continued
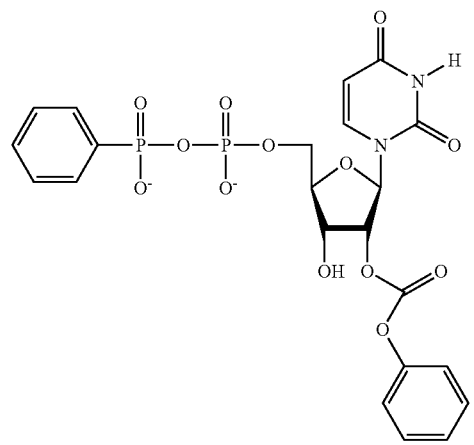
42
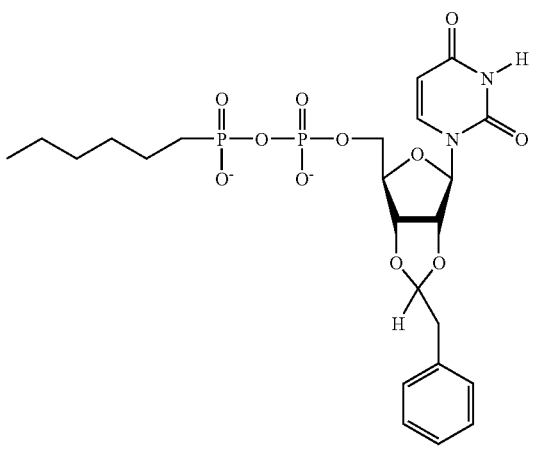
45
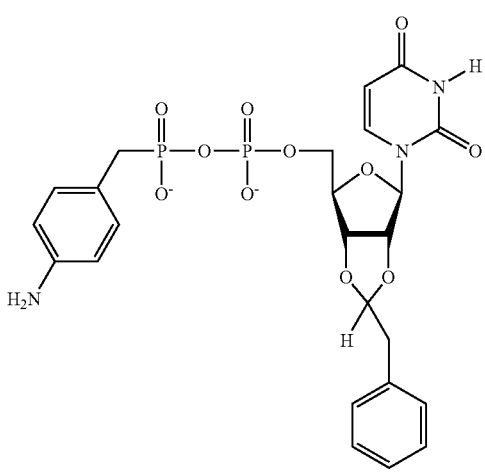
46
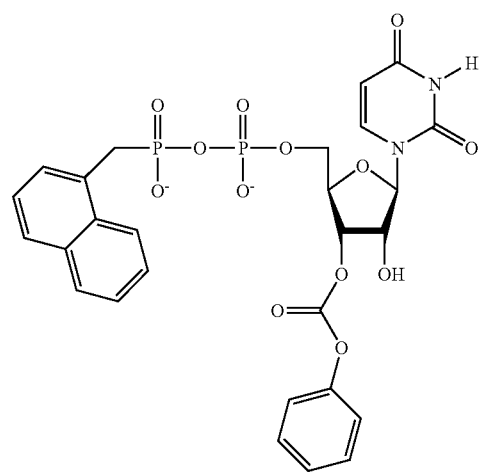
44
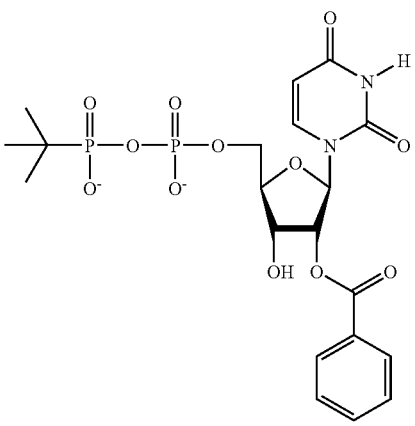
47

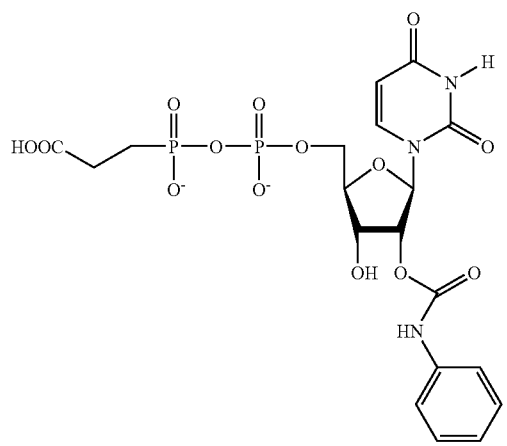
48
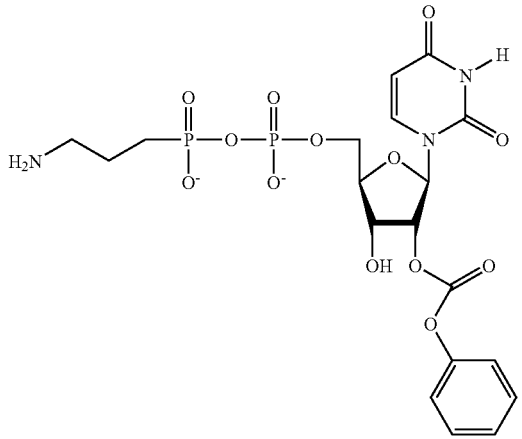
51
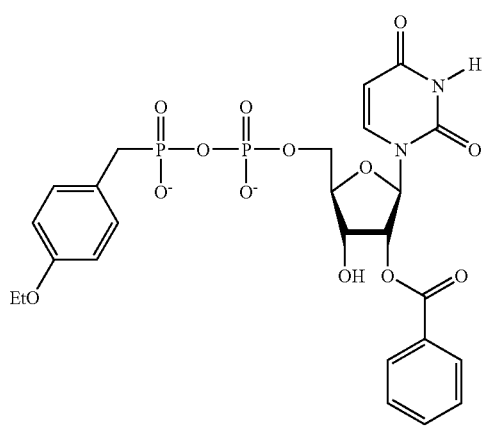
49
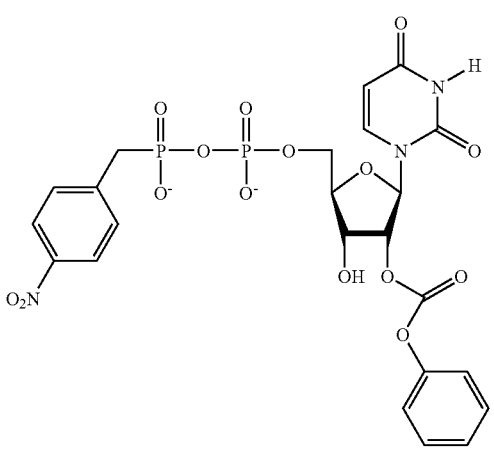
52
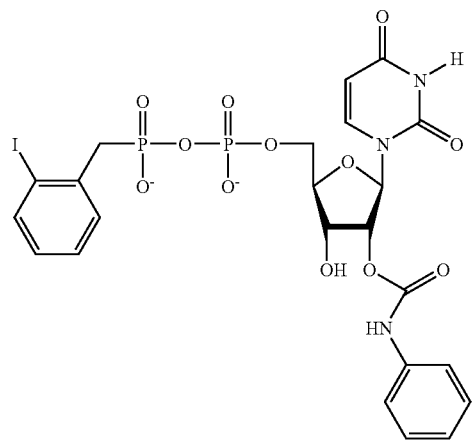
50
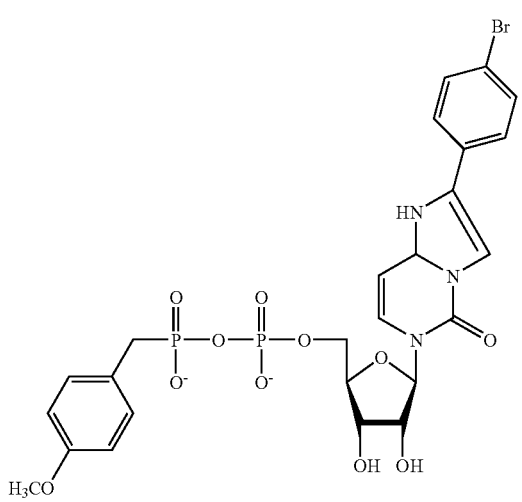
53

54
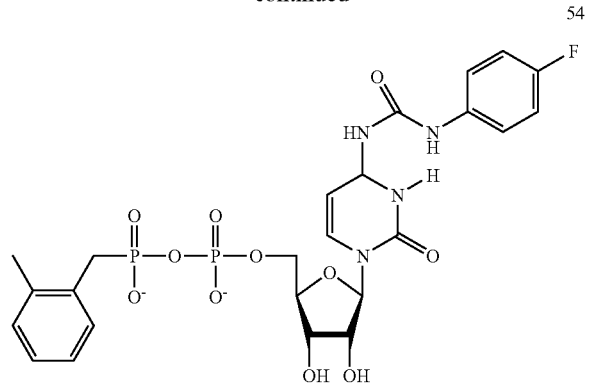
55
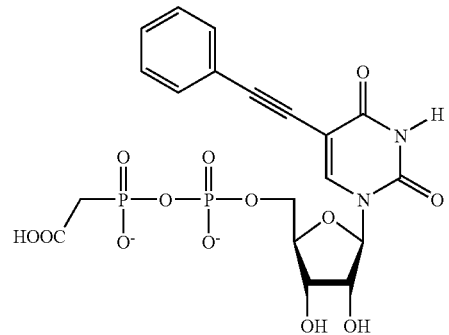
56
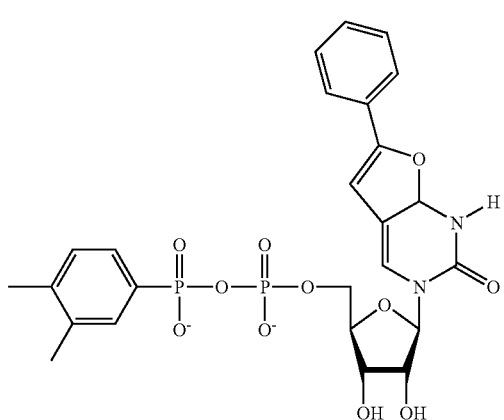
57
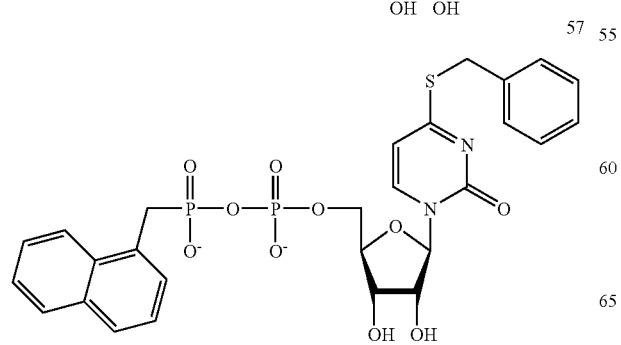
58
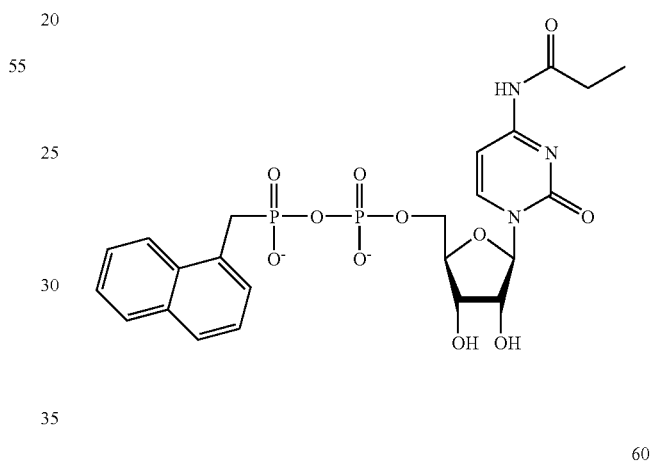
59
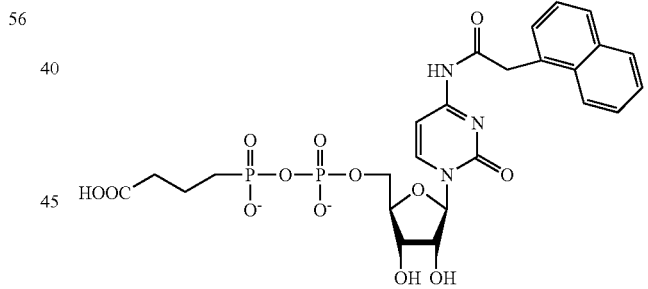
60
61
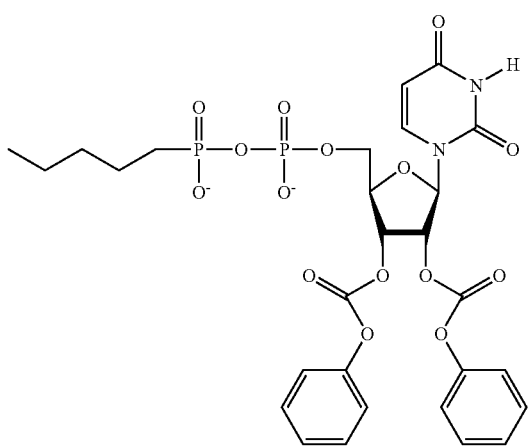

-continued
62
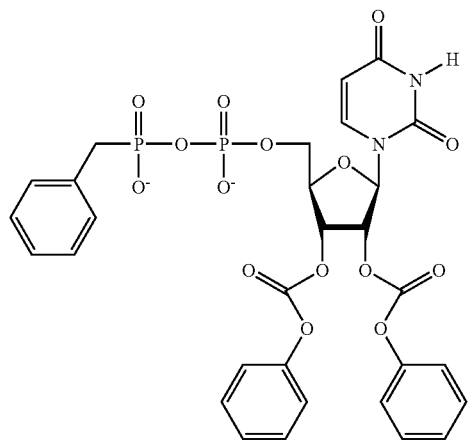
63
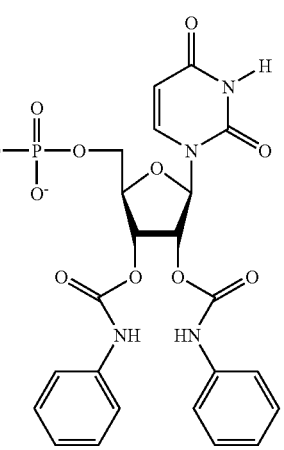
64
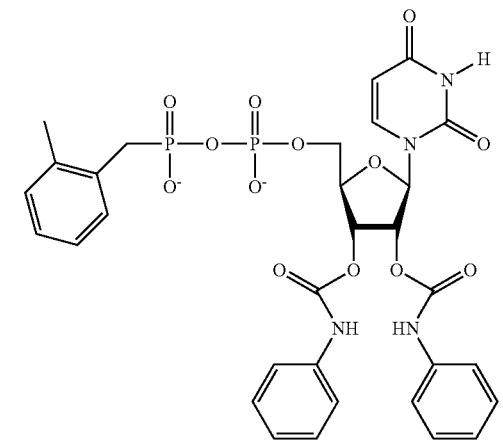
-continued
65
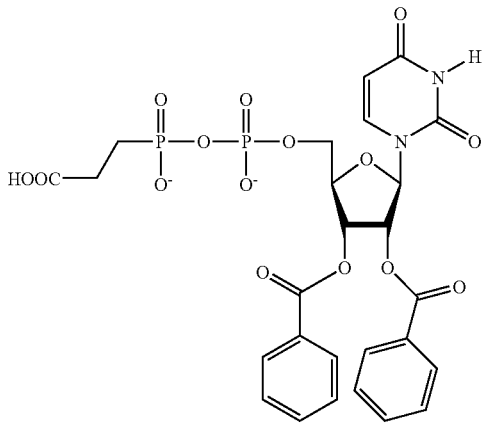
66
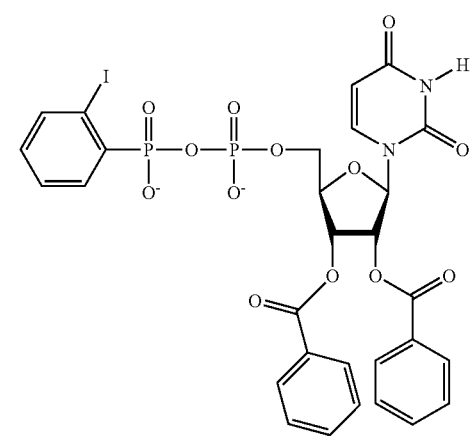
67
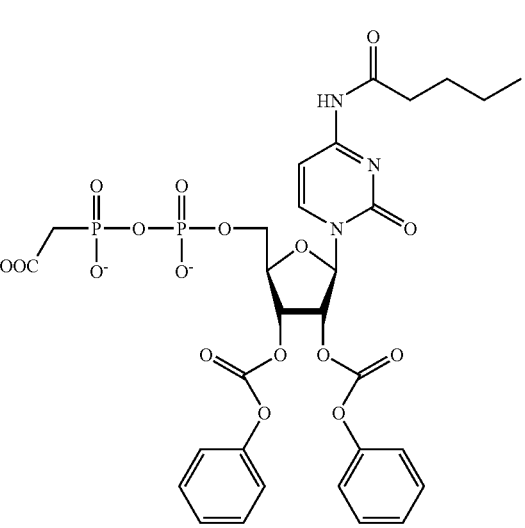

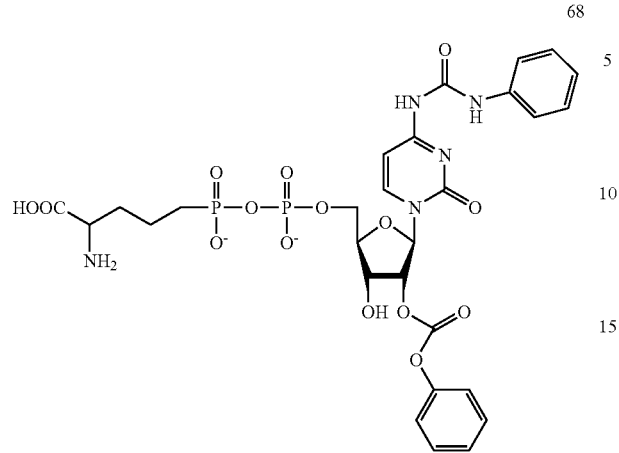
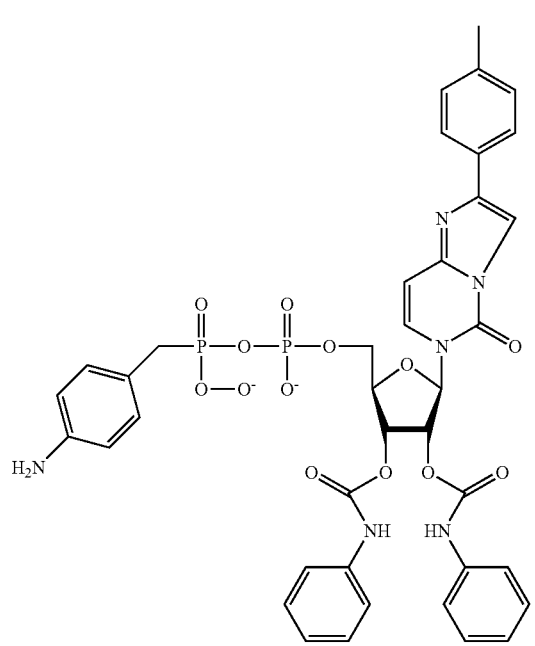
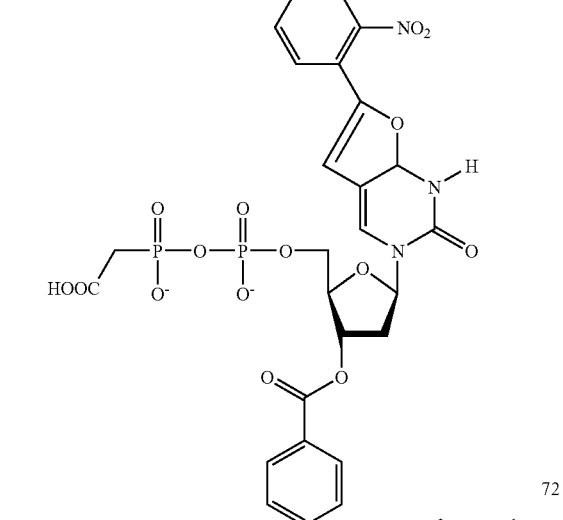
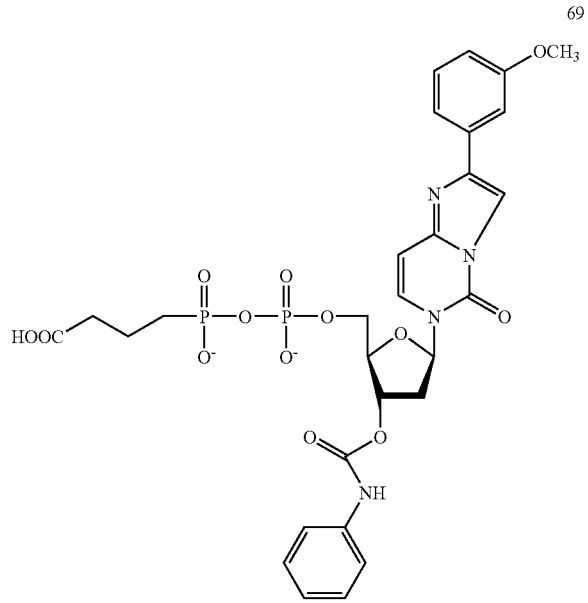
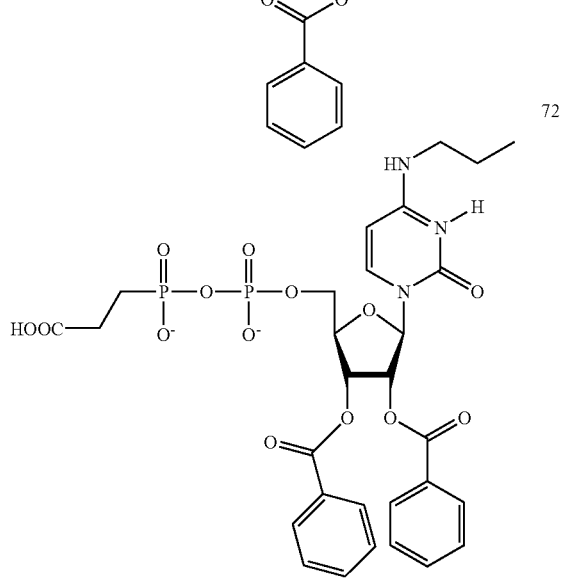
Structures 73-130 exemplify pyrimidine triphosphates and tetraphosphates where A=OR$_1$, SR$_1$, or NR$_1$R2:

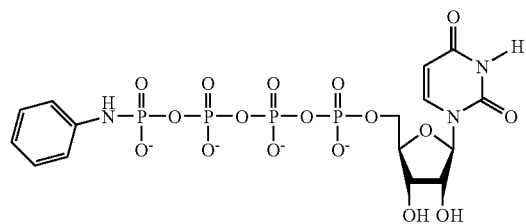
73
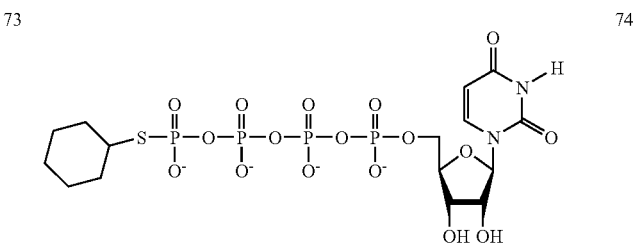
74
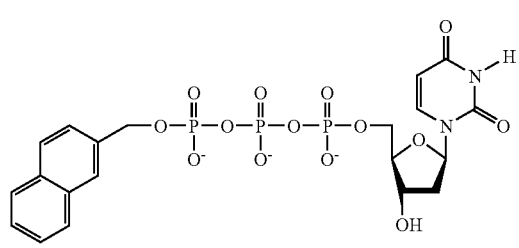
75
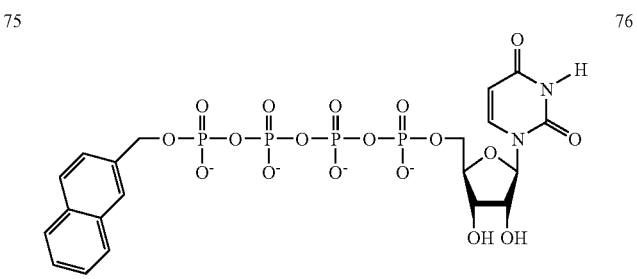
76
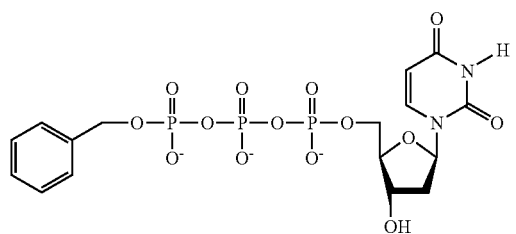
77
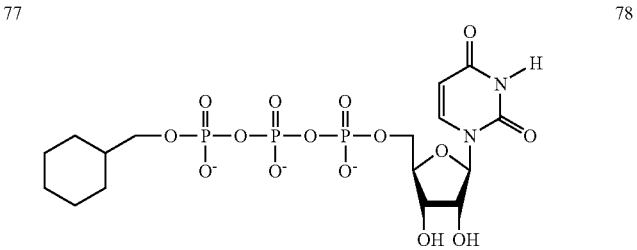
78
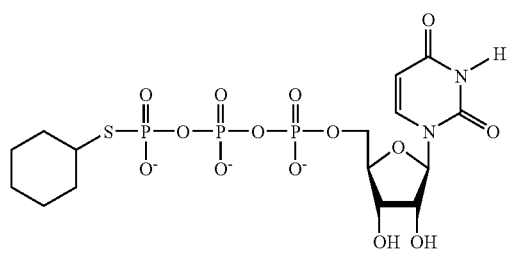
79
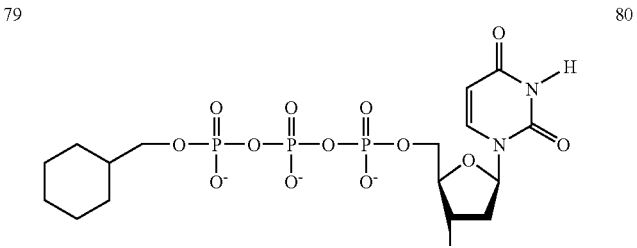
80
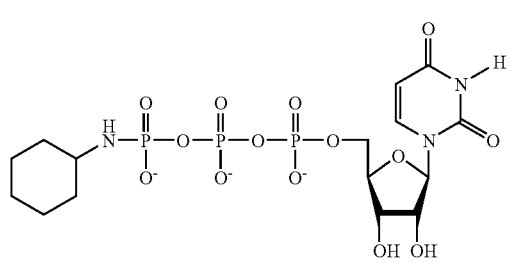
81
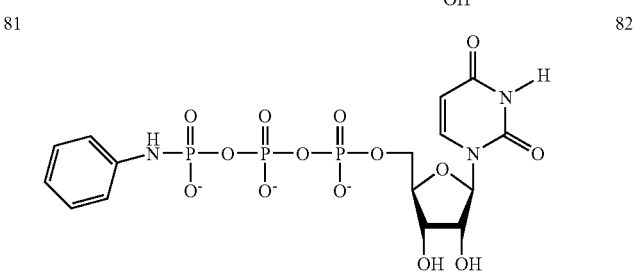
82
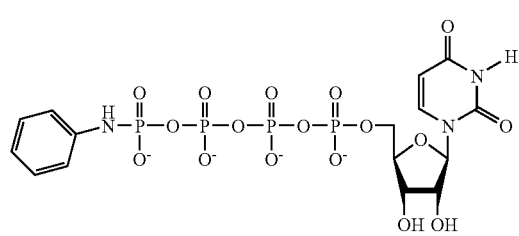
83
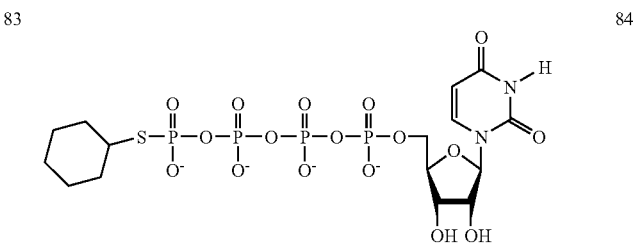
84

-continued
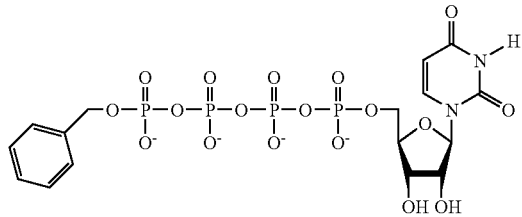
85
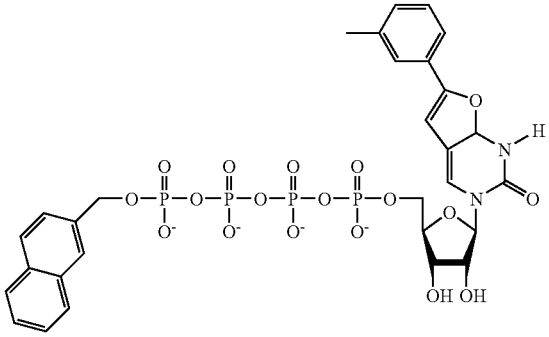
86
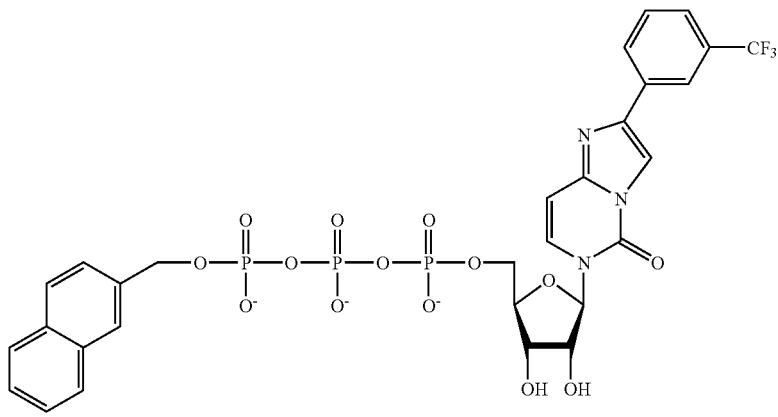
87
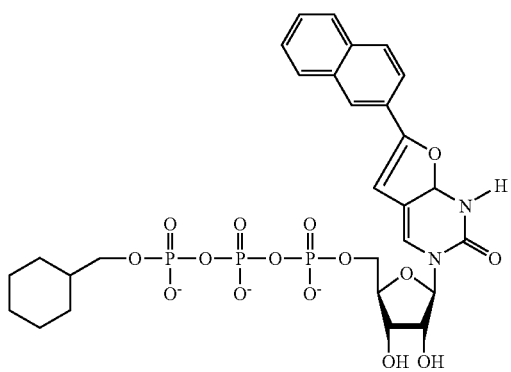
88
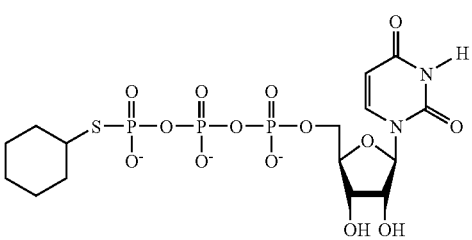
89
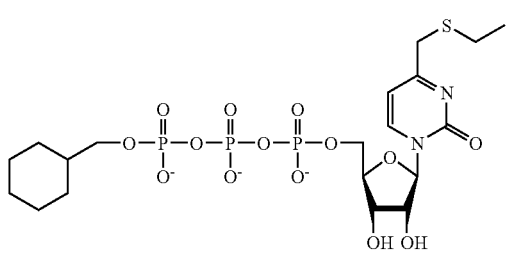
90
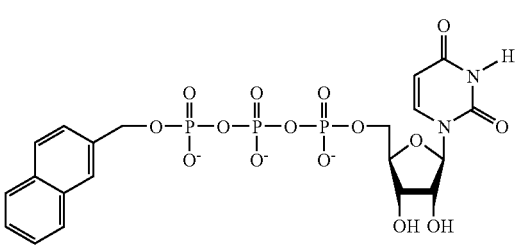
91

-continued
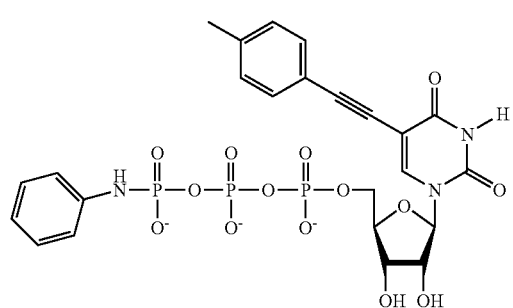
92
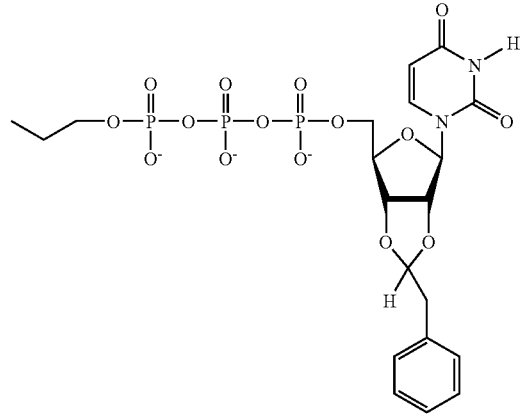
93
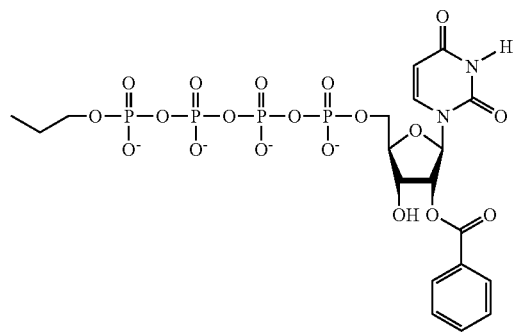
94
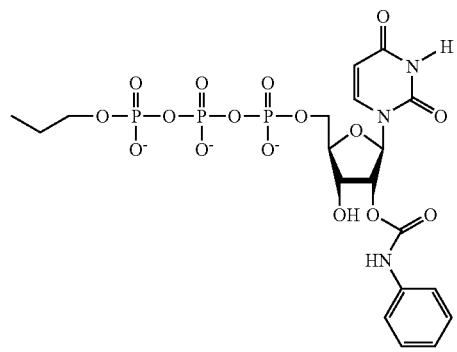
95
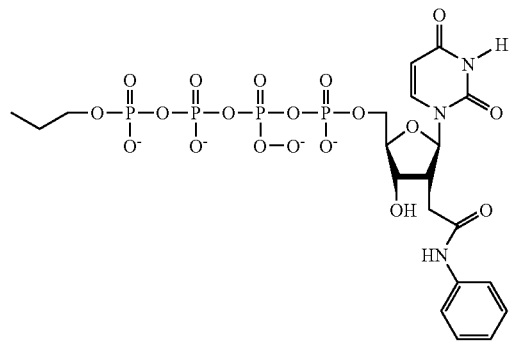
96
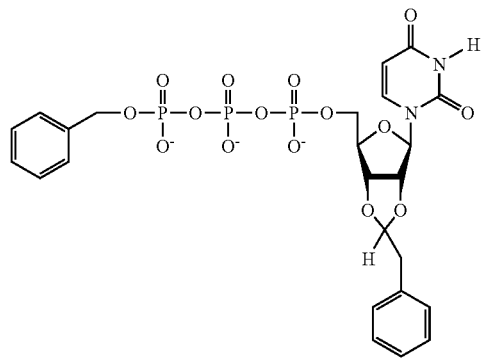
97
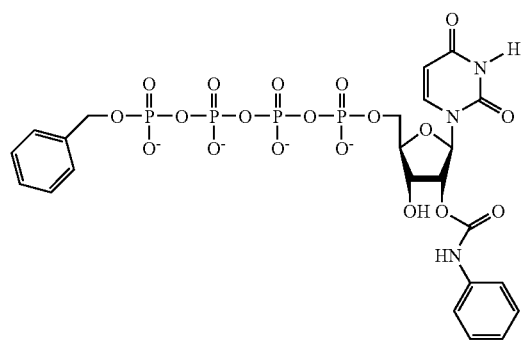
98
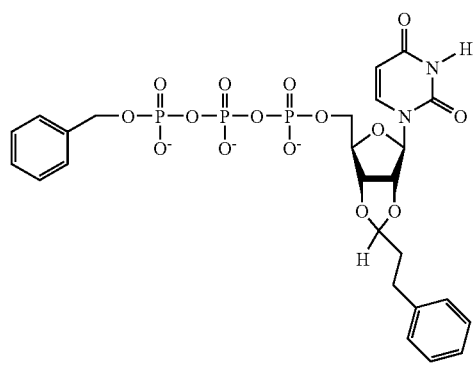
99

-continued
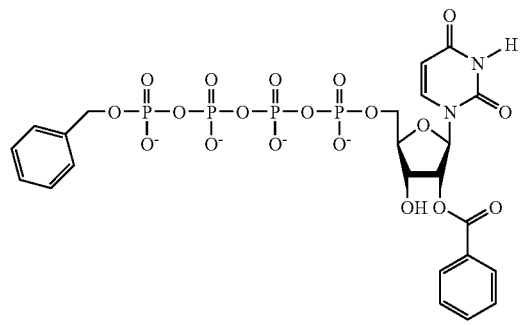
100
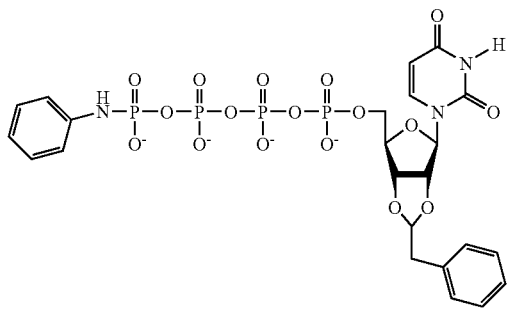
101
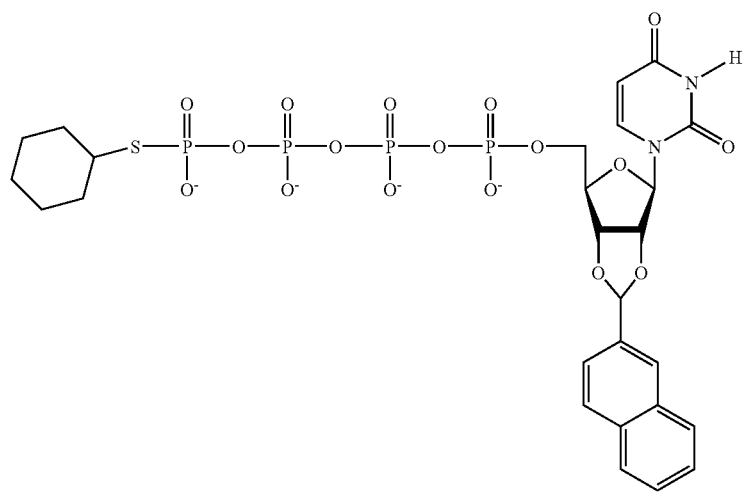
102
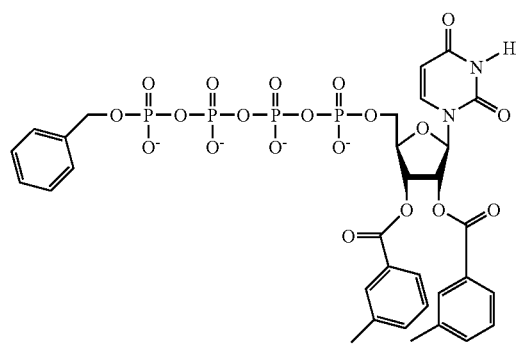
103
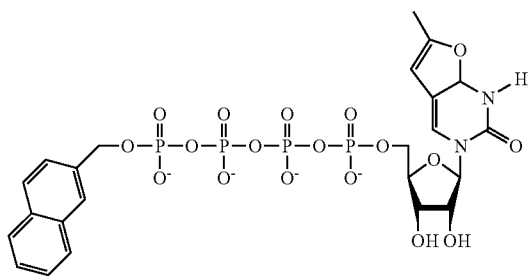
104

-continued
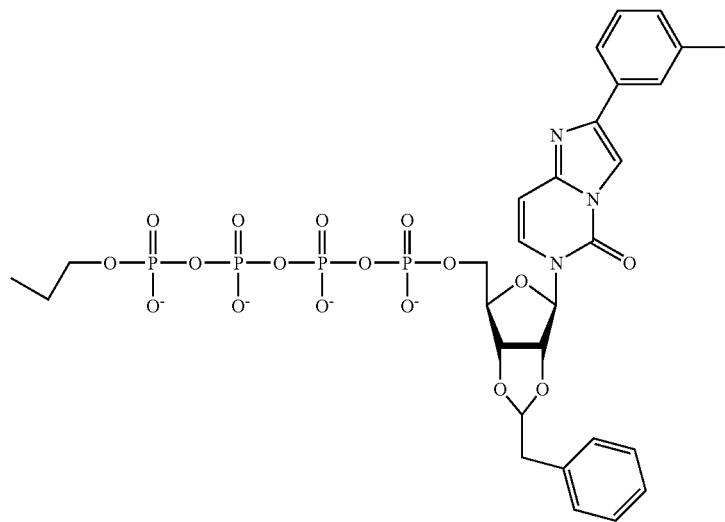
105
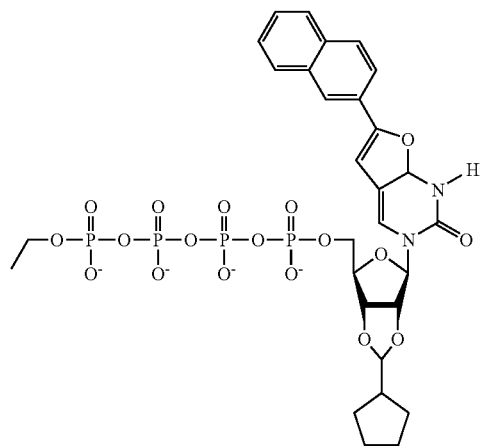
106
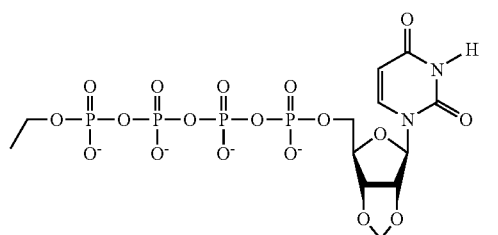
107
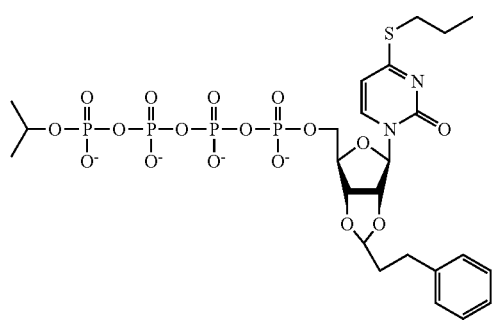
108
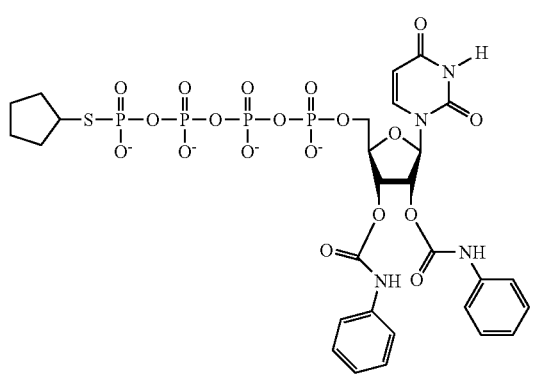
109

-continued
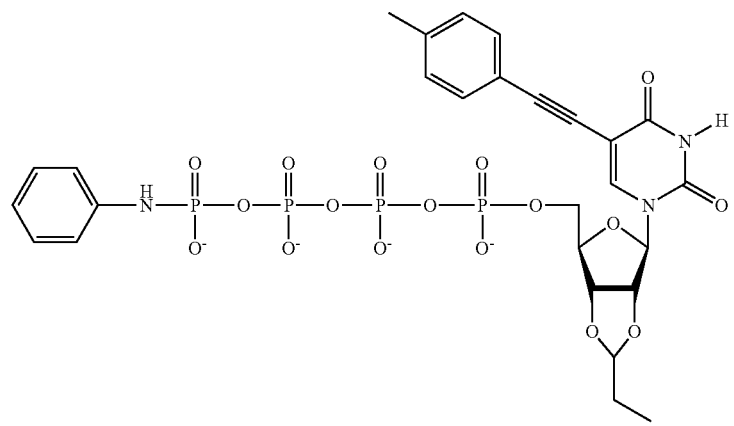
110
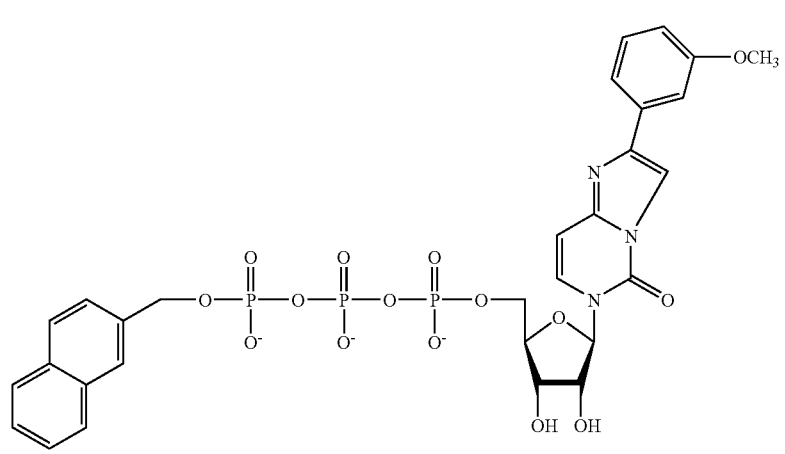
111
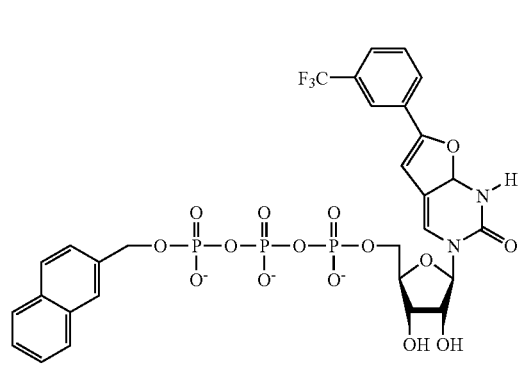
112
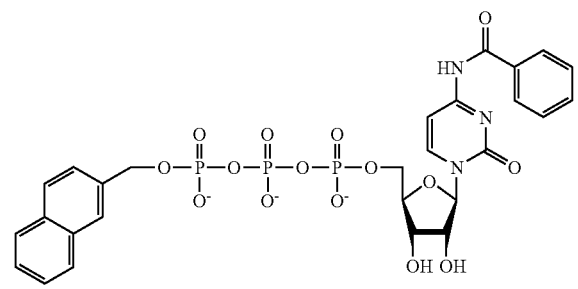
113
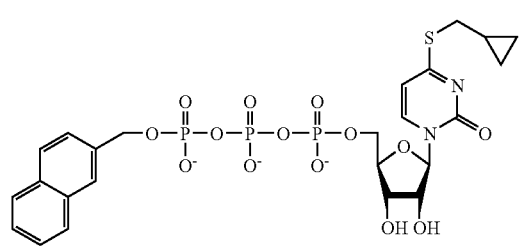
114
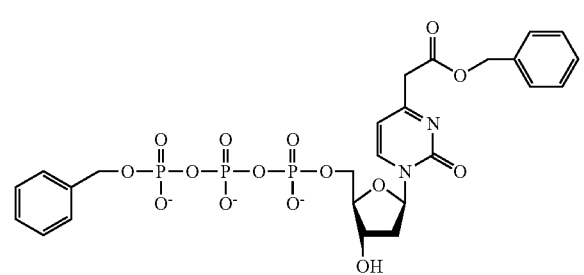
115

-continued
116
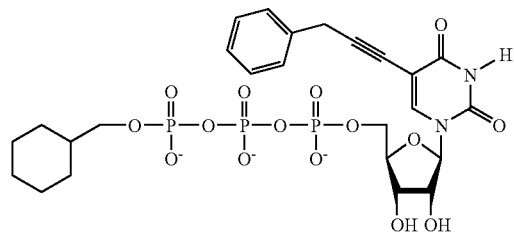
117
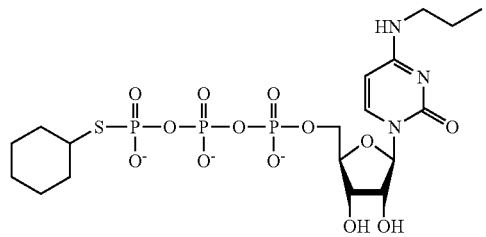
118
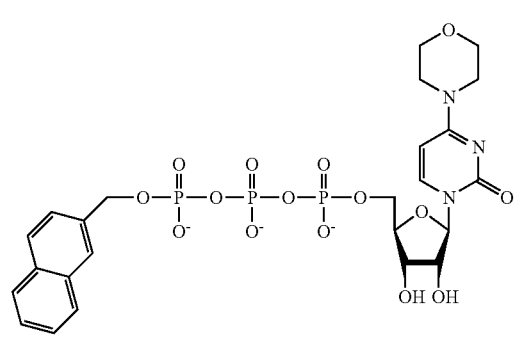
119
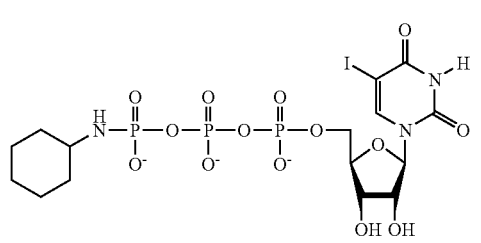
120
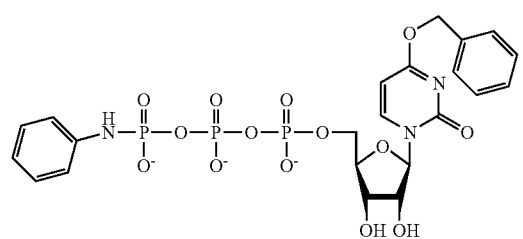
121
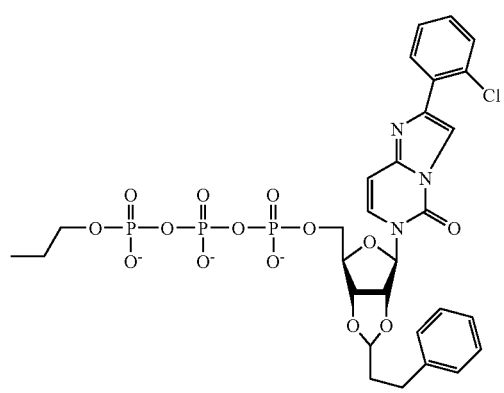
122
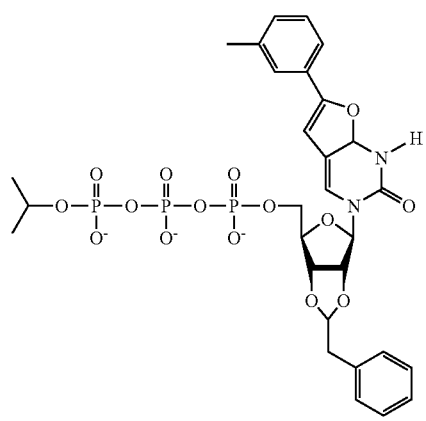
123
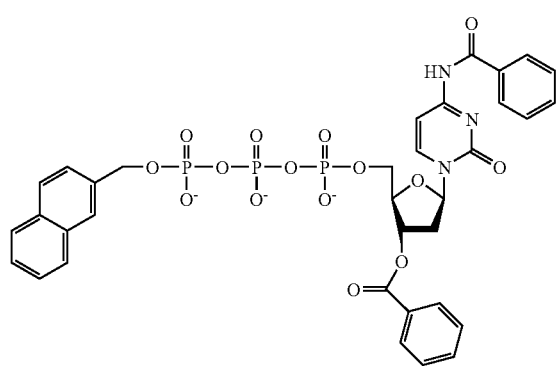

-continued
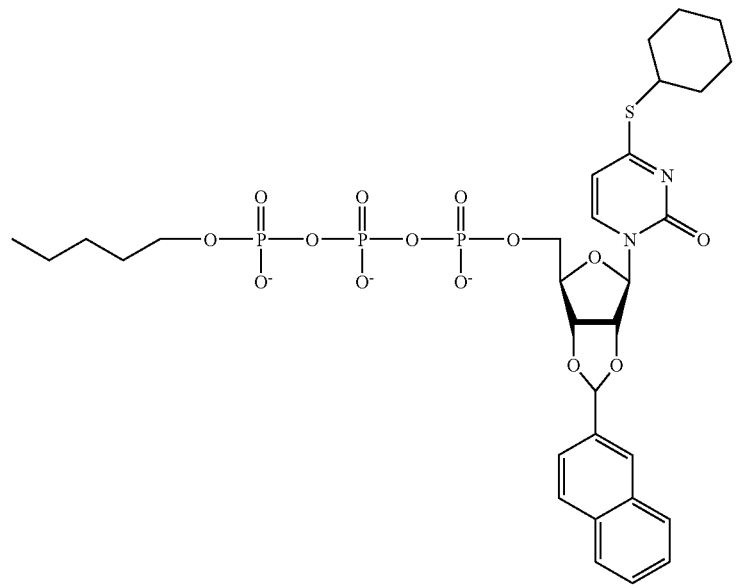
124
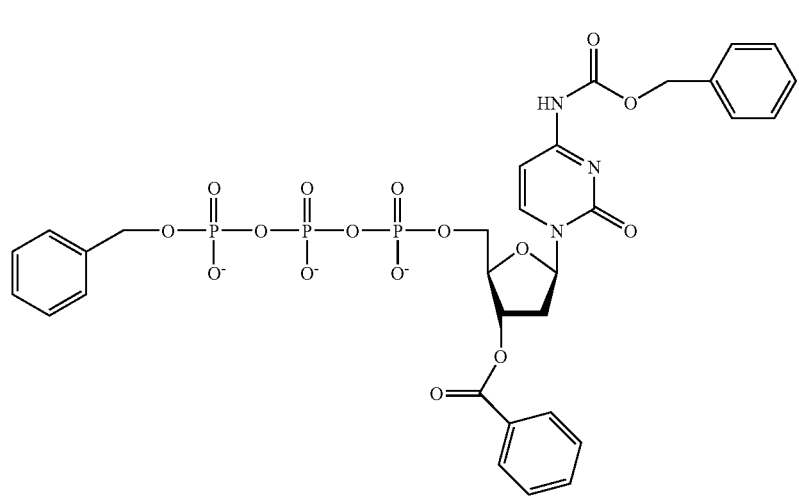
125
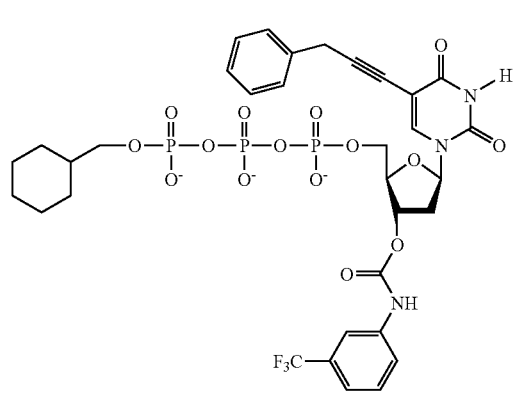
126
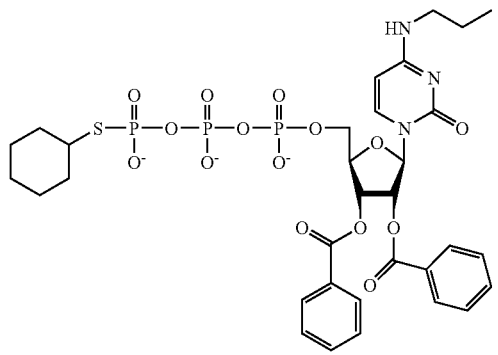
127

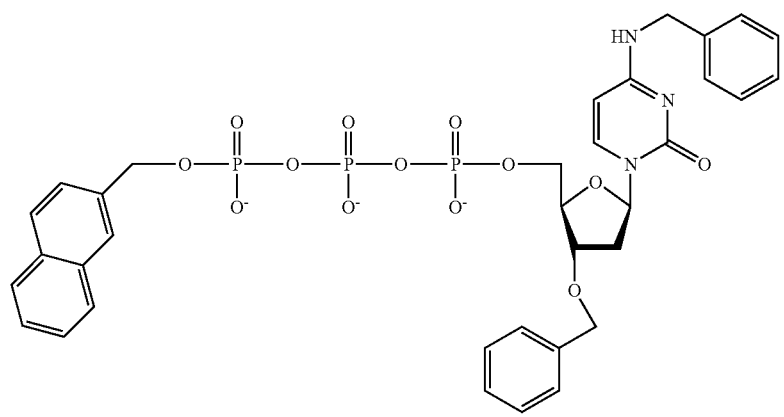
128
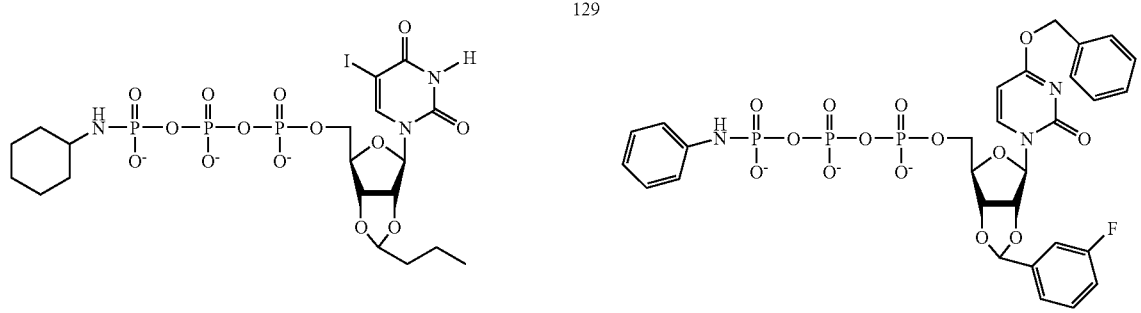
129          130
Structures 131-168 exemplify pyrimidine triphosphates and tetraphosphates where A=CR₁R₂R₃:
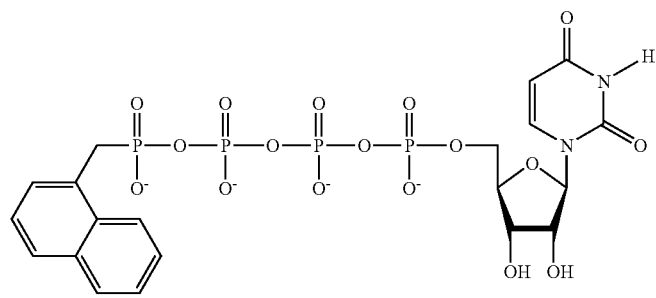
131
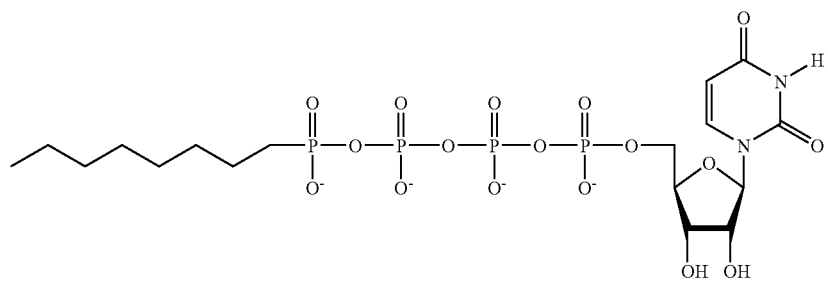
132

-continued
133 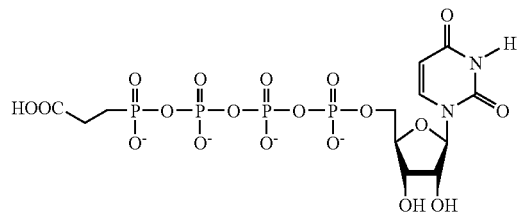
134 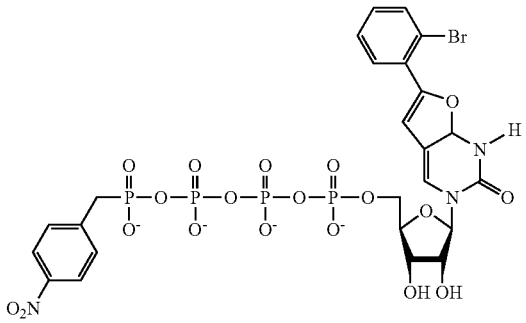
135 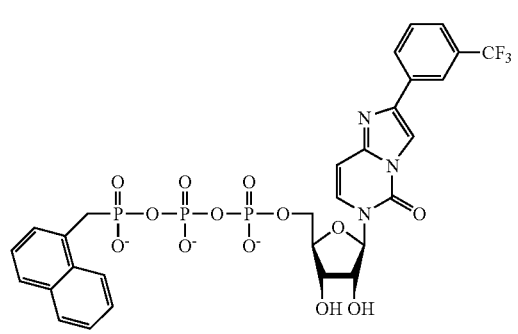
136 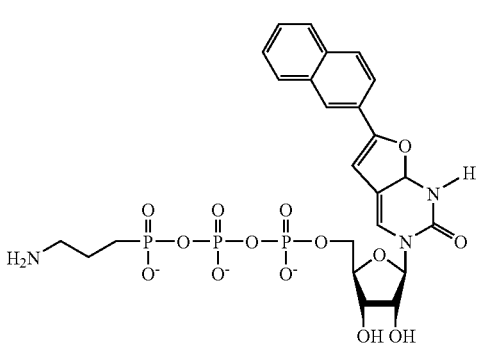
137 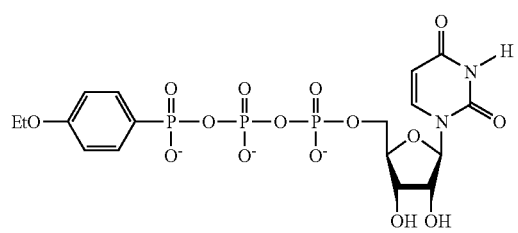
138 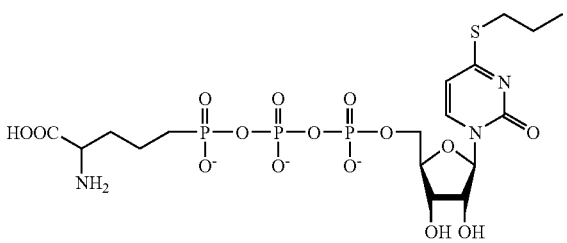
139 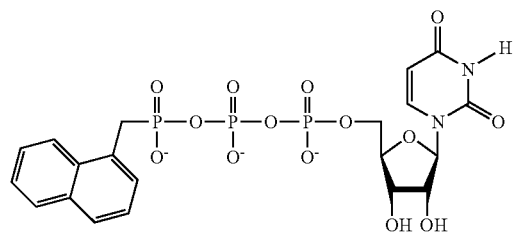
140 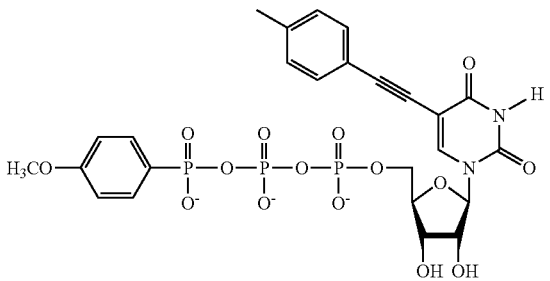
141 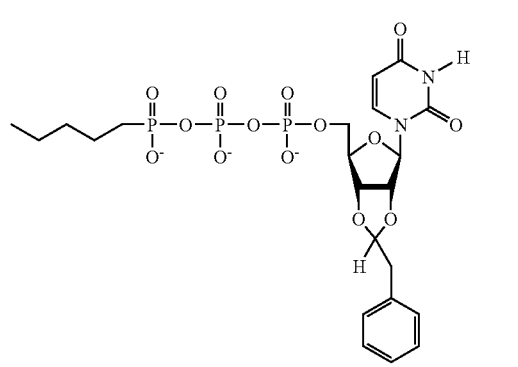
142 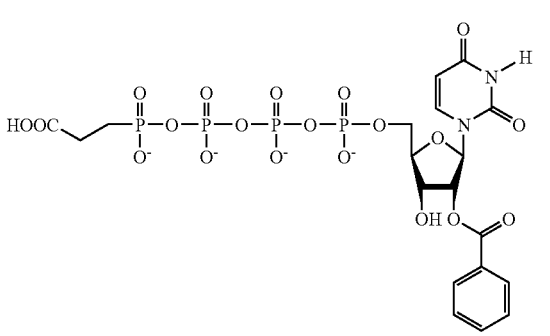

-continued
143
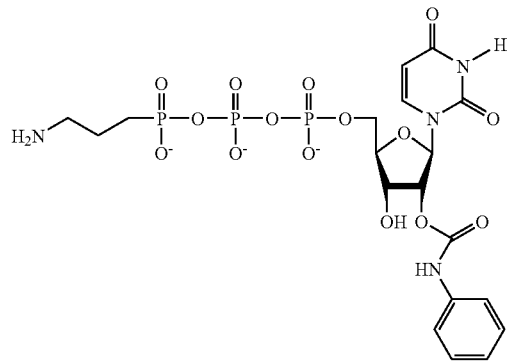
144
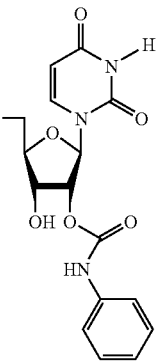
145
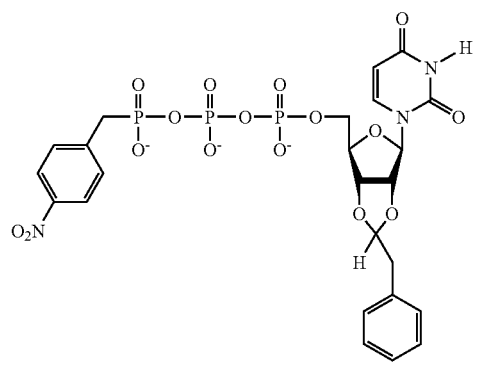
146
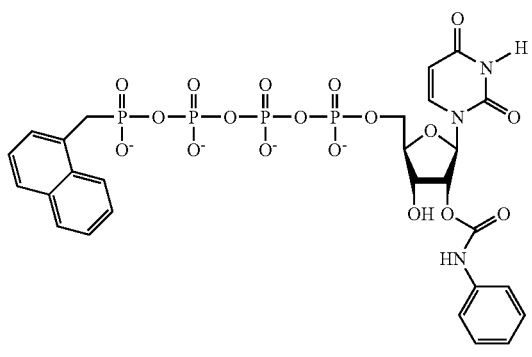
147
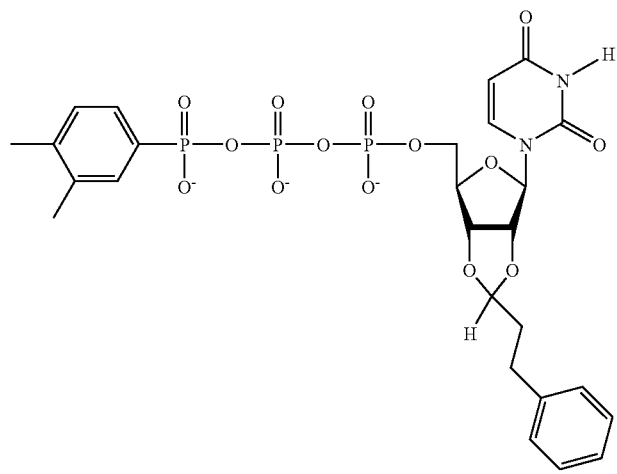
148
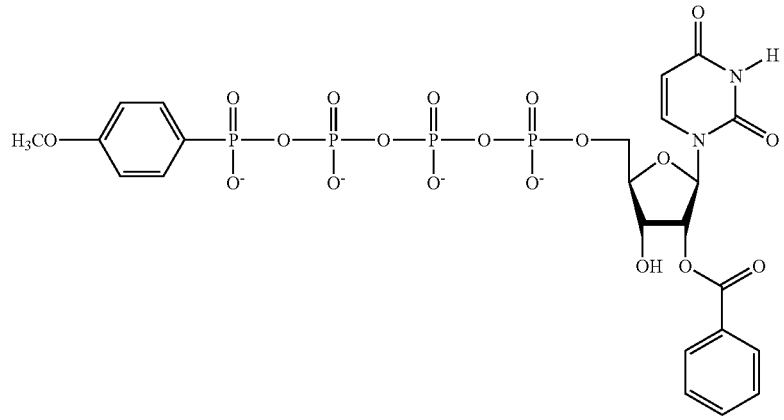

-continued
149
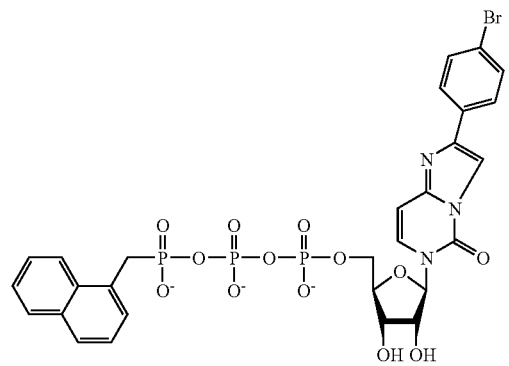
150
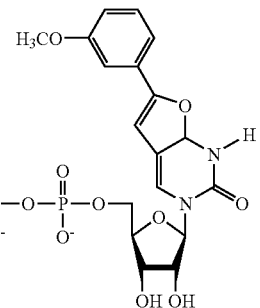
151
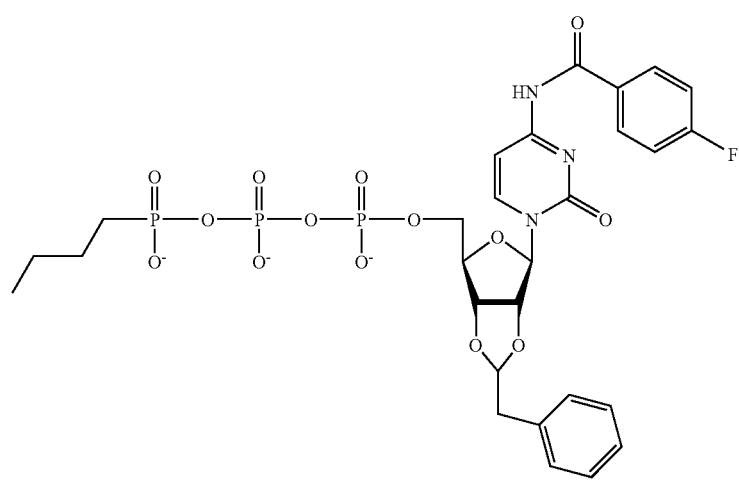
152
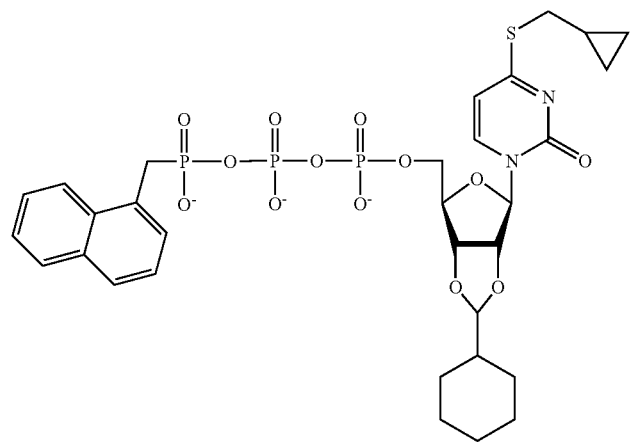
153
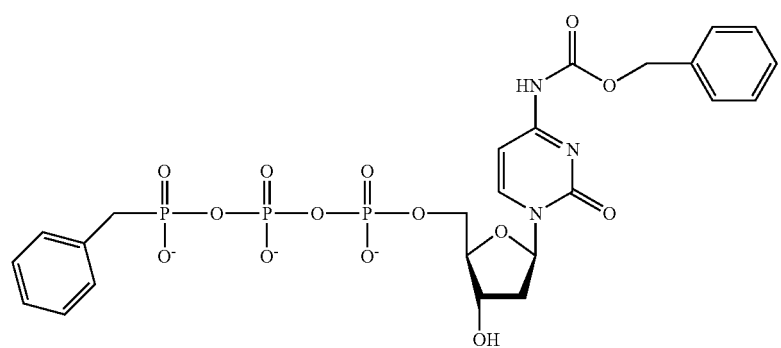

-continued
154
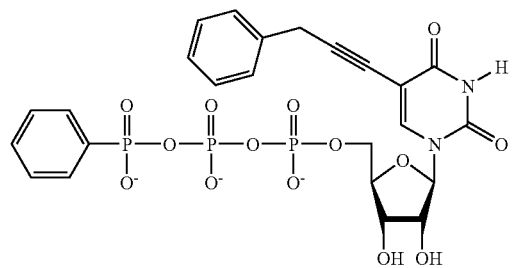
155
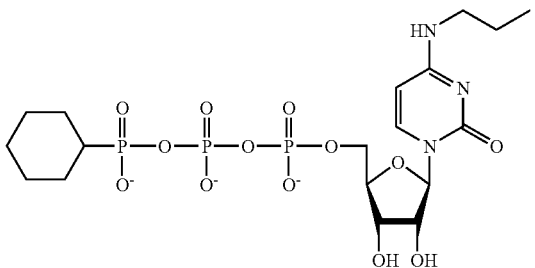
156
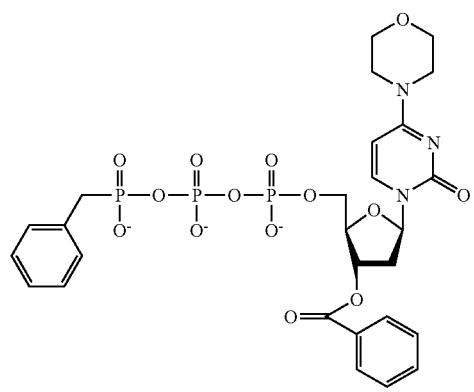
157
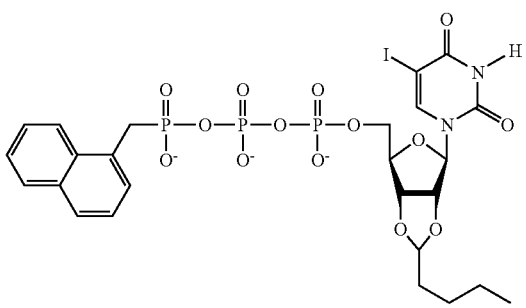
158
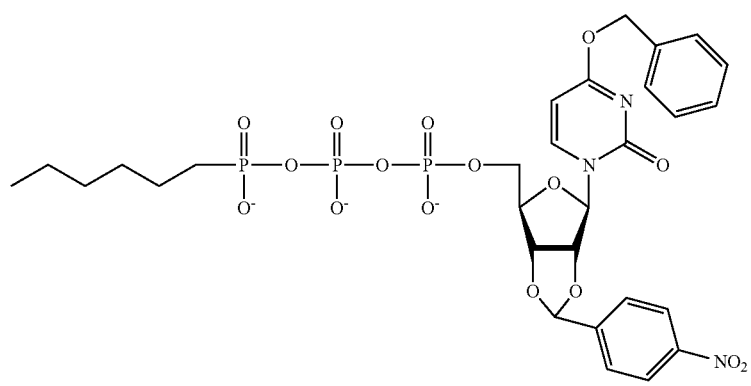
159
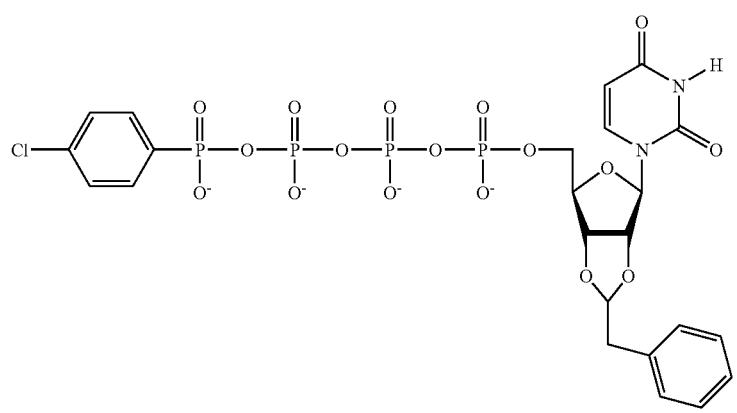

-continued
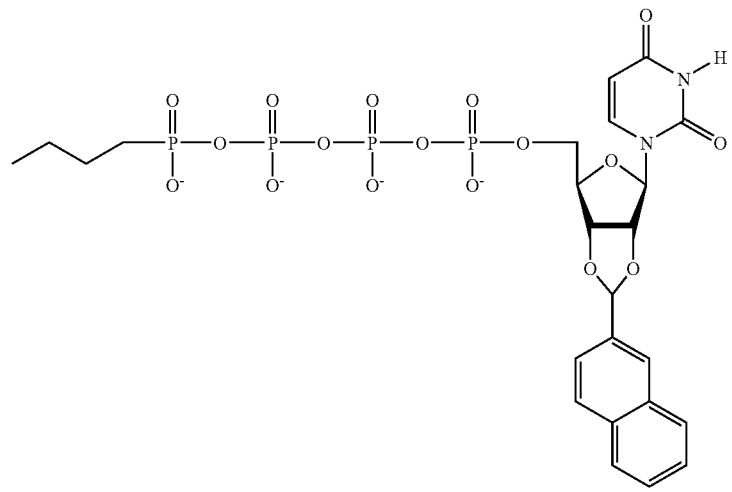
160
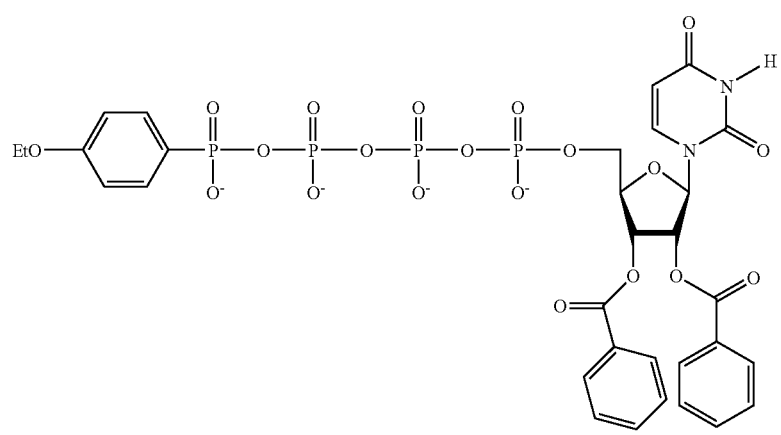
161
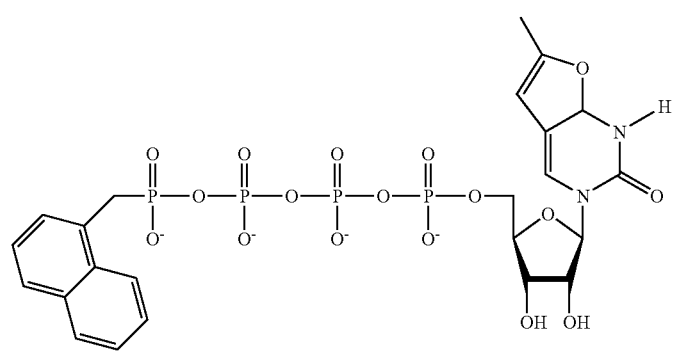
162

-continued
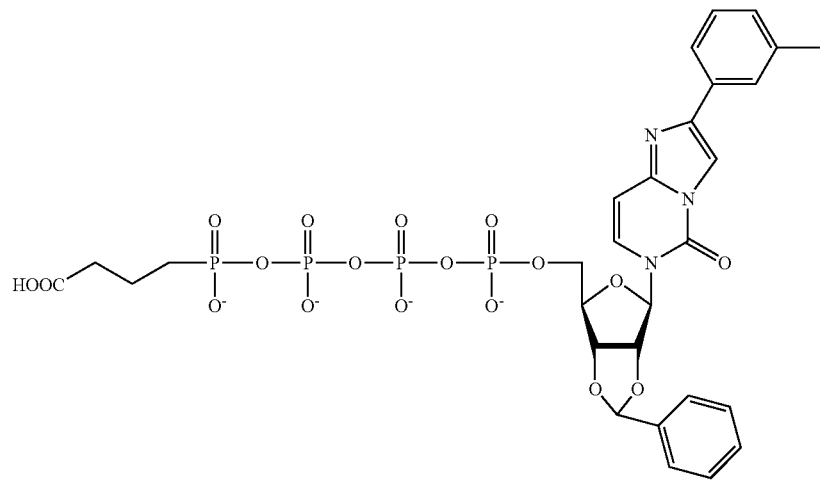
163
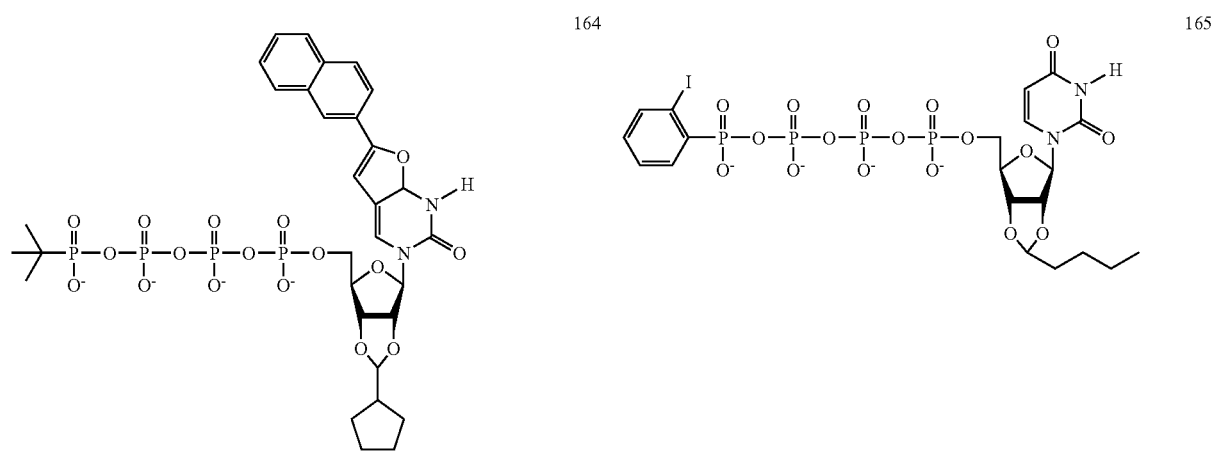
164
165
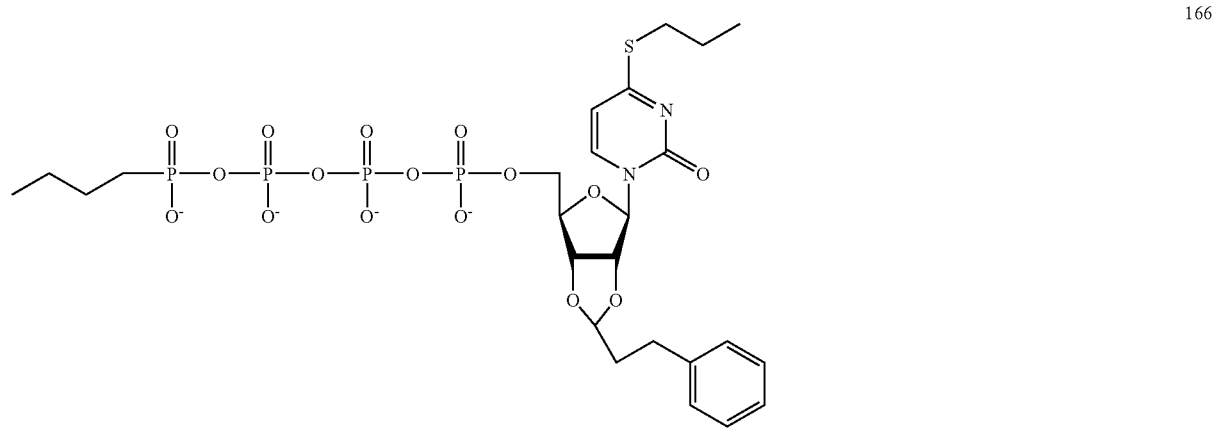
166

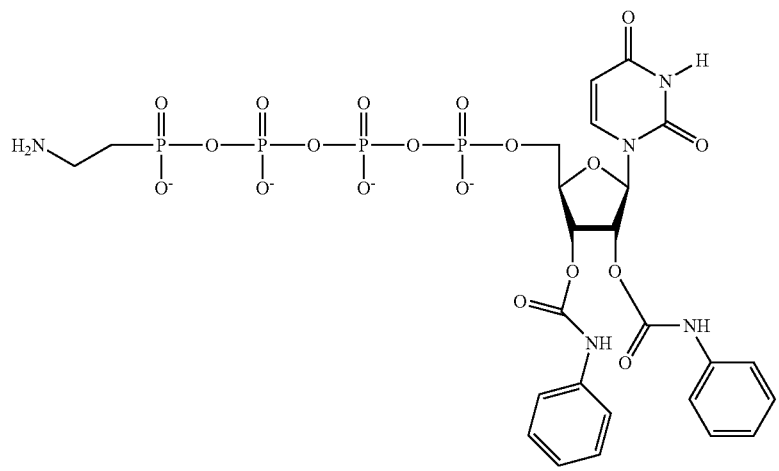
167
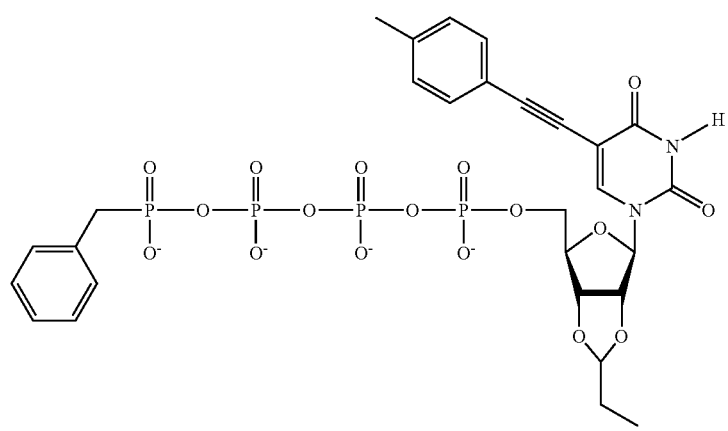
168
Structures 169-192 exemplify adenosine triphosphates and tetraphosphates where A=OR$_1$, SR$_1$, or NR$_1$R$_2$:
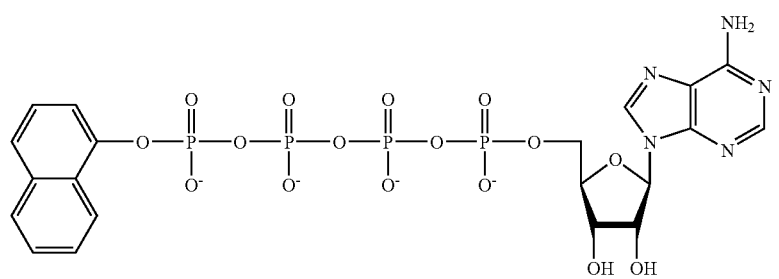
169
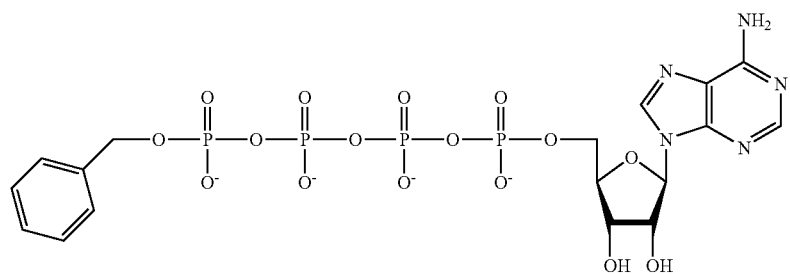
170

-continued
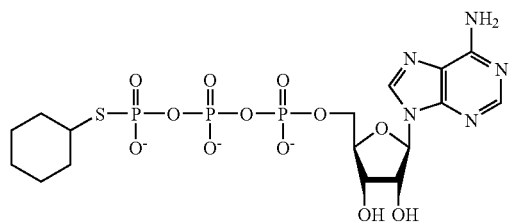
171
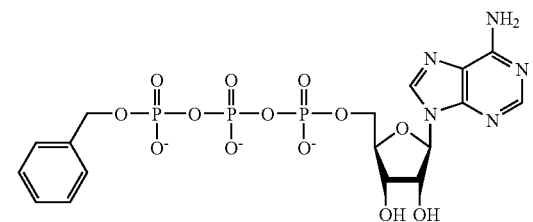
172
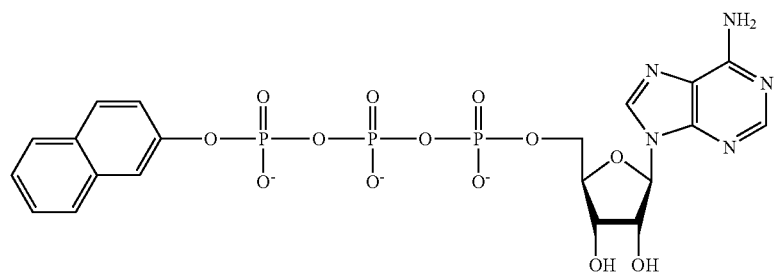
173
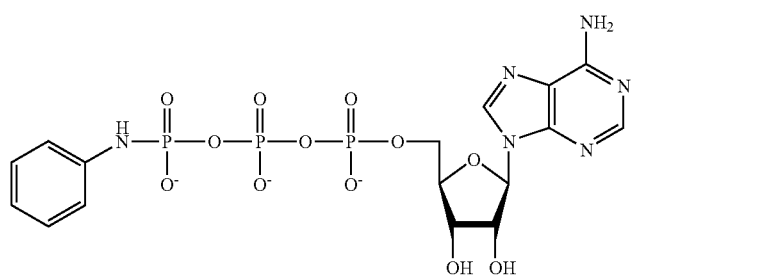
174
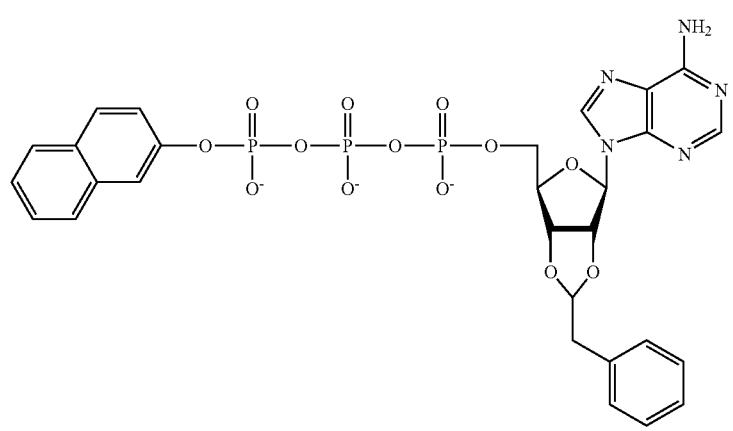
175
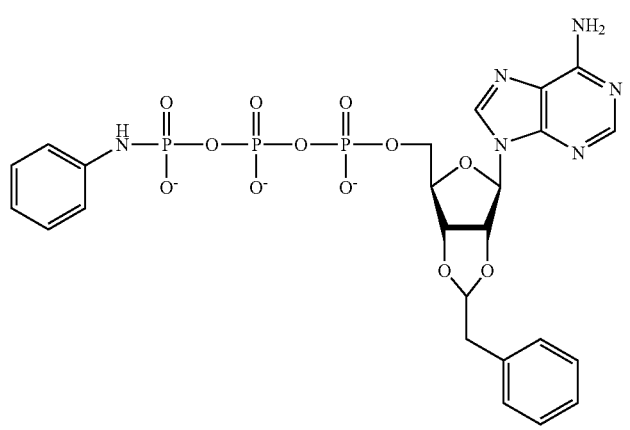
176

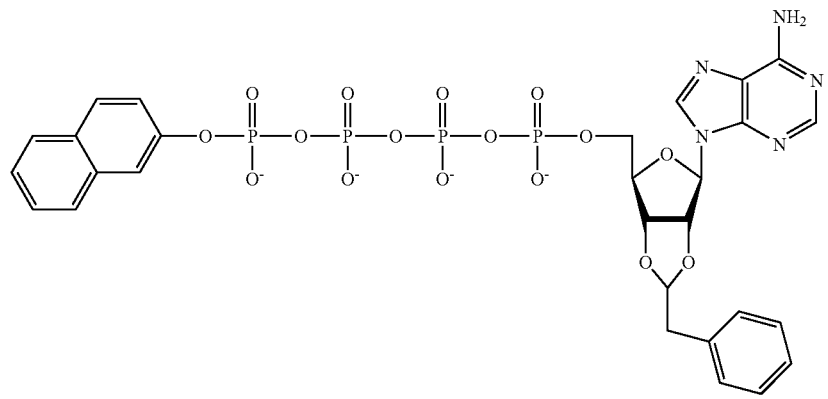
177
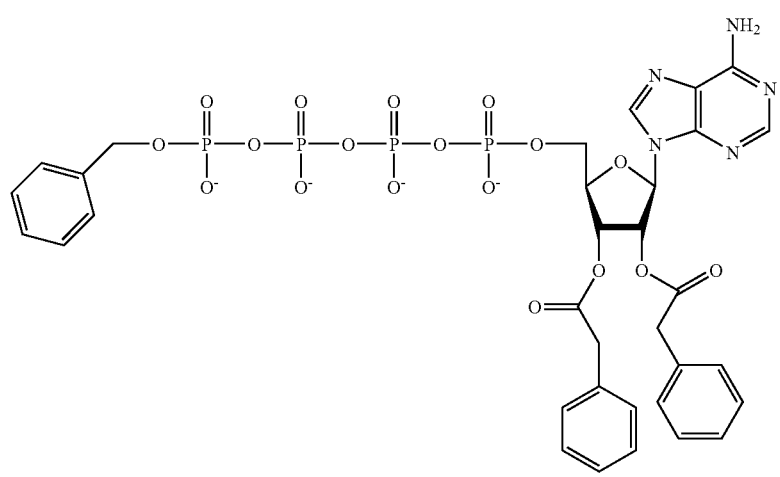
178
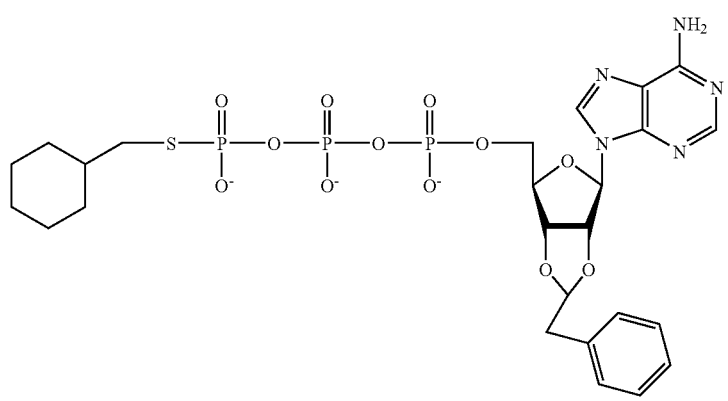
179

-continued
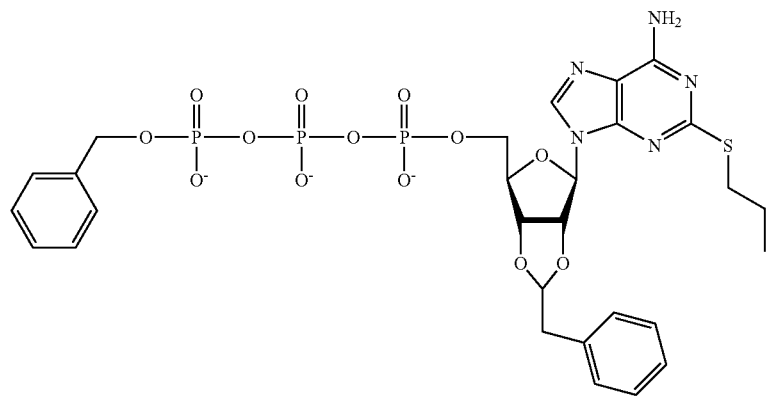
180
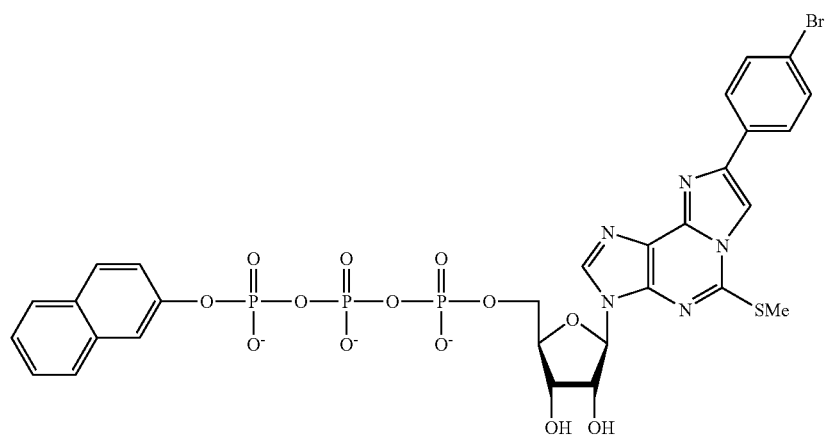
181
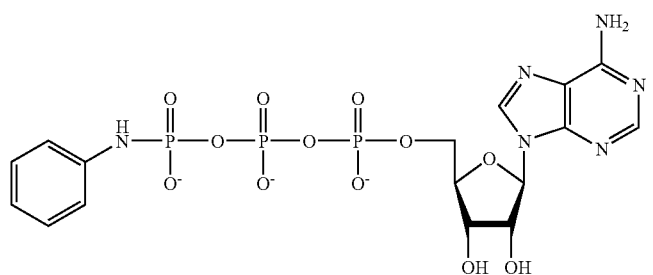
182
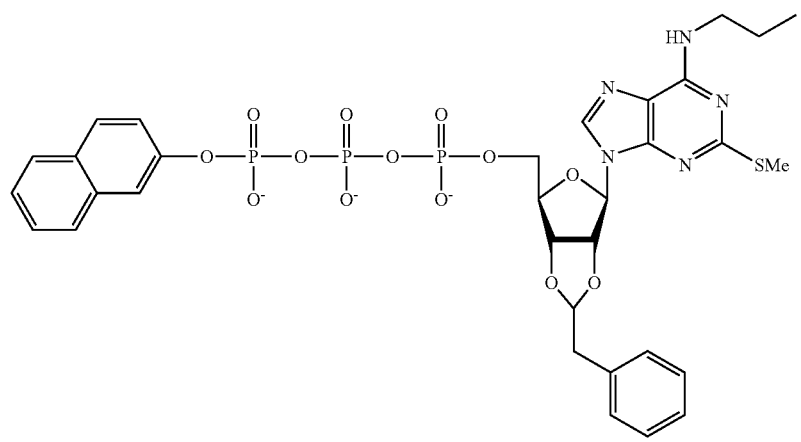
183

184
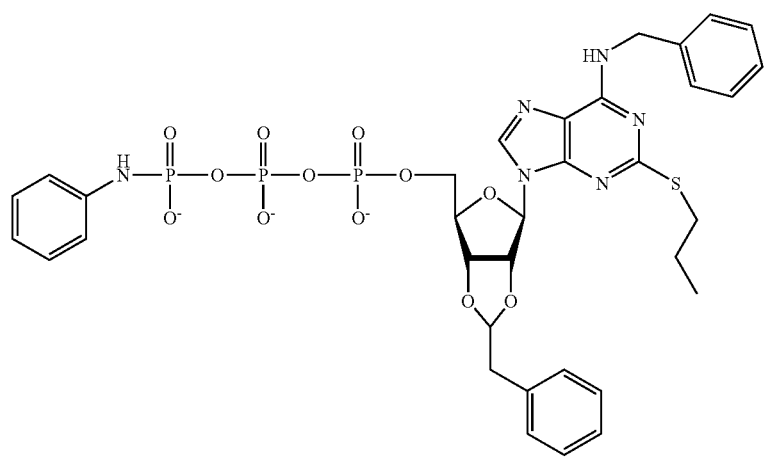
185
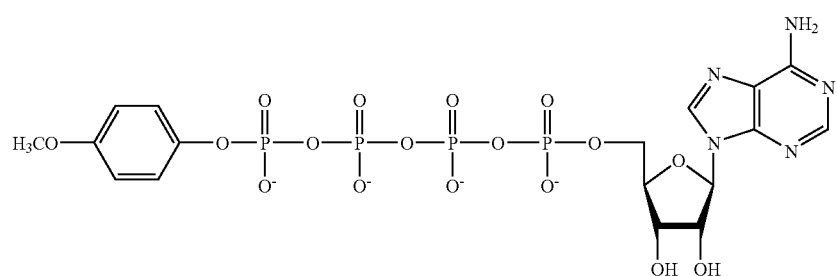
186
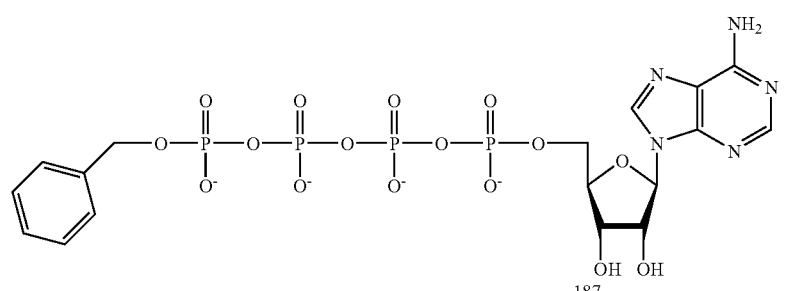
187                              188
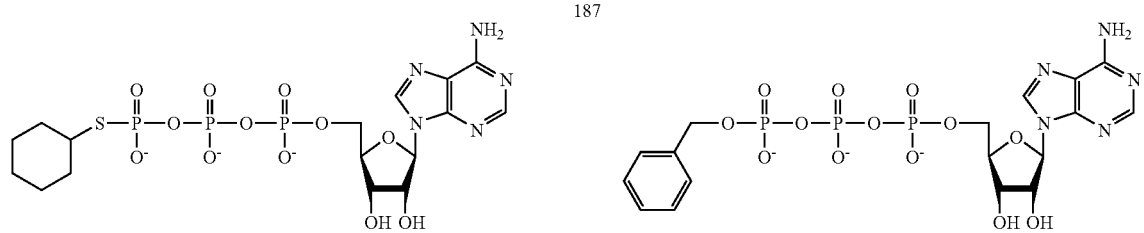
189
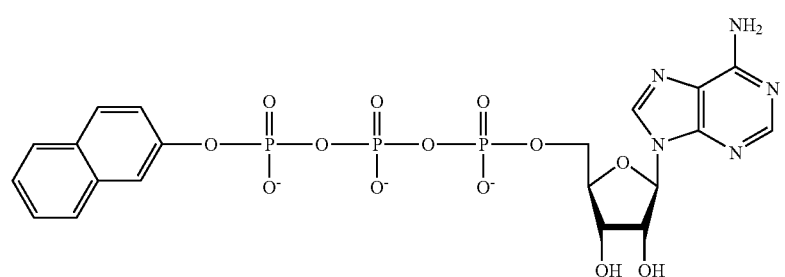

-continued
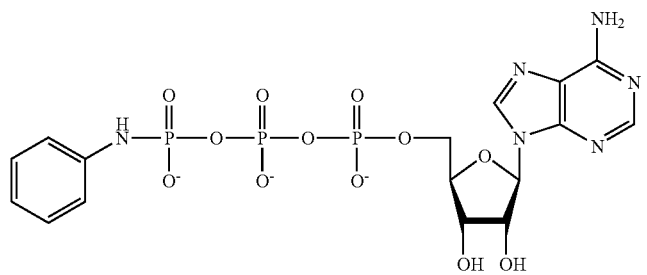
190
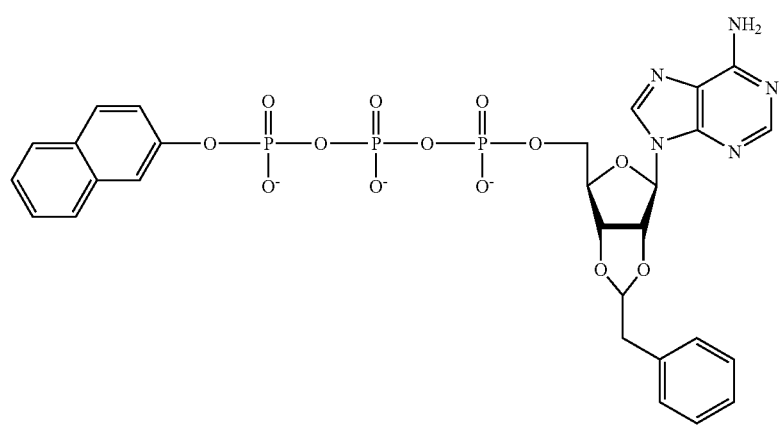
191
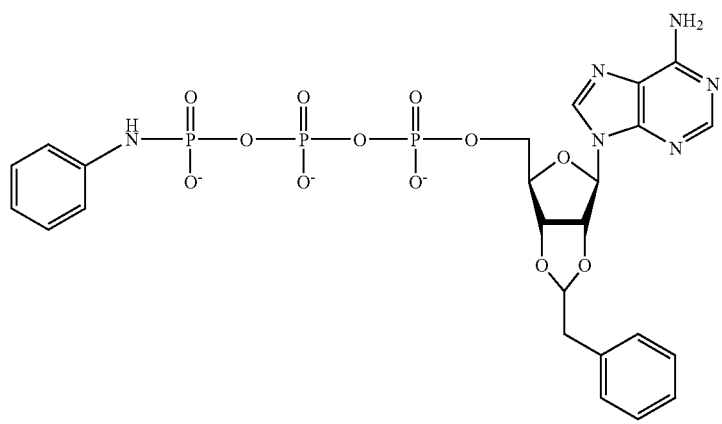
192
Structures 193-216 exemplify adenosine triphosphates and tetraphosphates where A=CR$_1$R$_2$R$_3$:
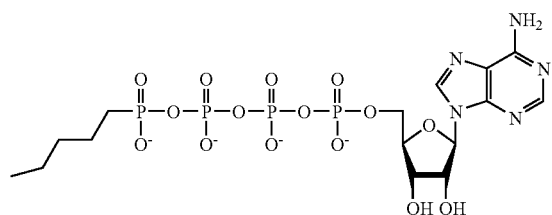
193
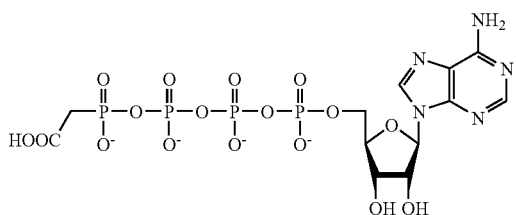
194

-continued
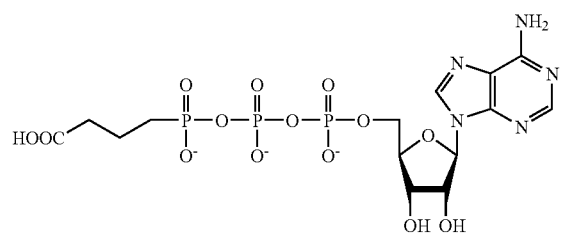
195
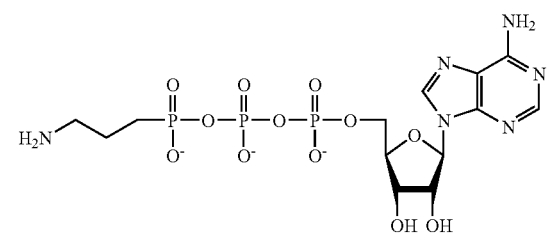
196
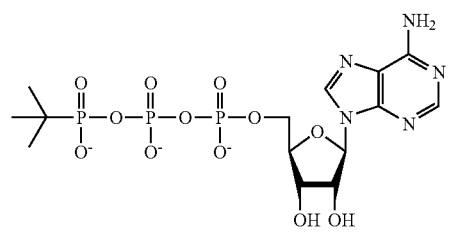
197
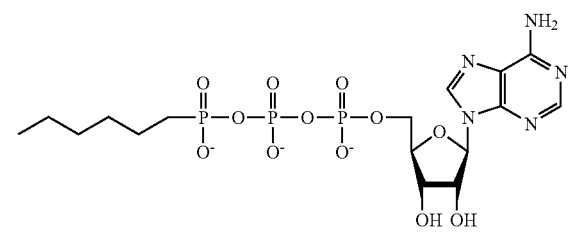
198
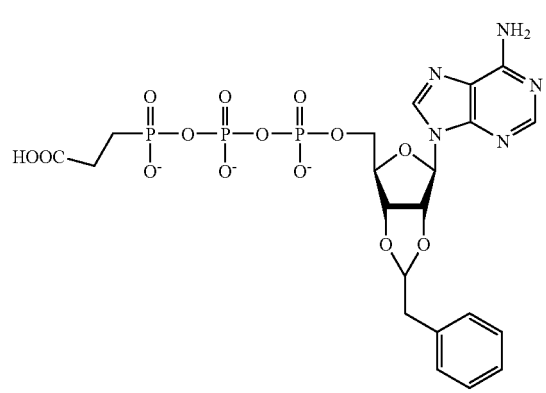
199
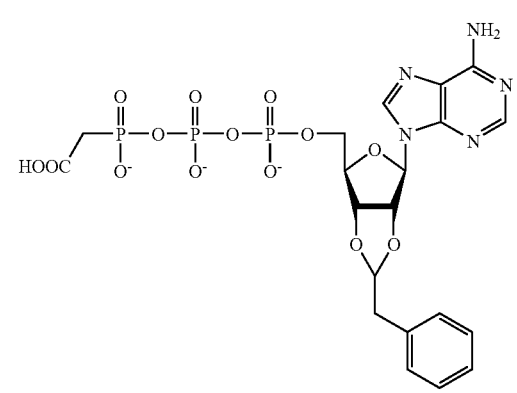
200
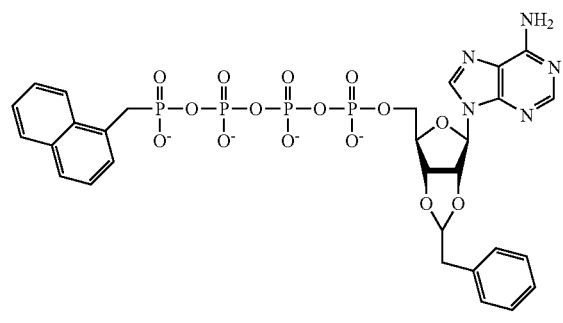
201
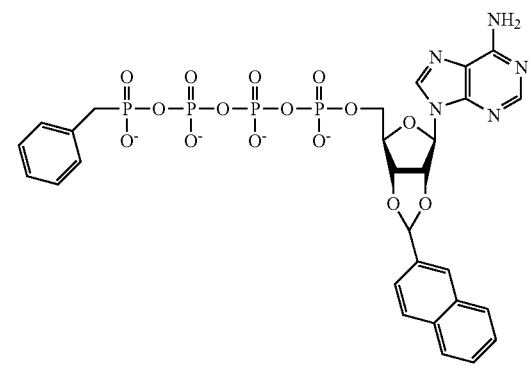
202

-continued
203
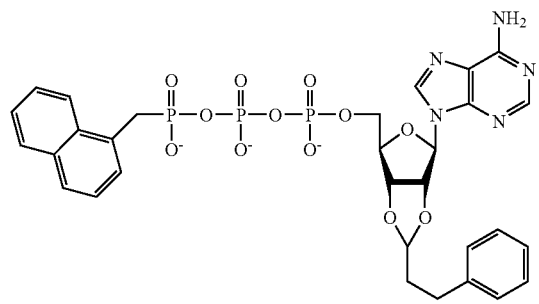
204
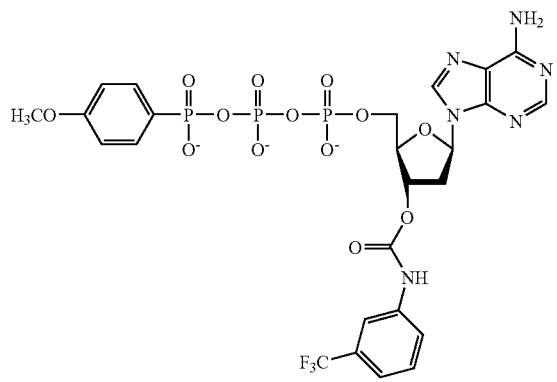
205
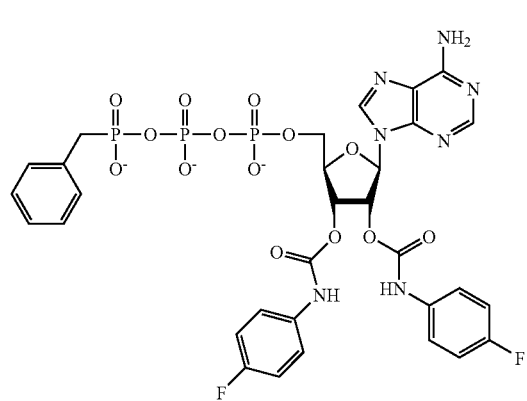
206
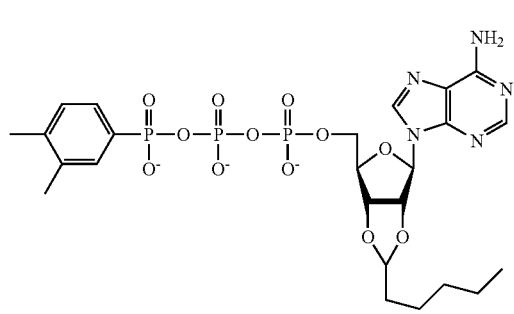
207
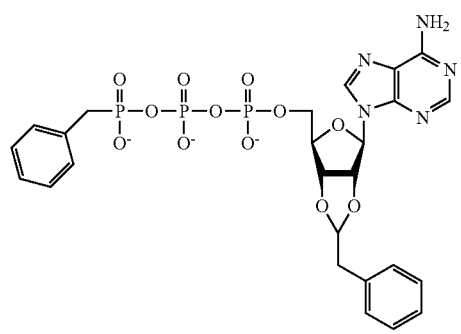
208
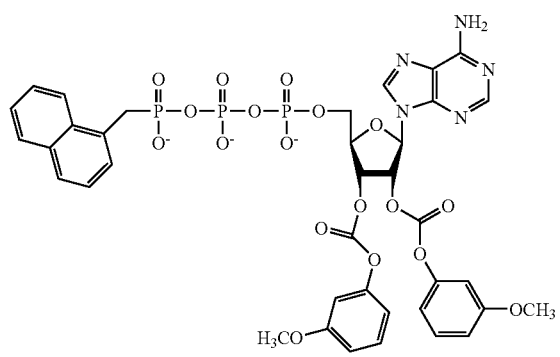
209
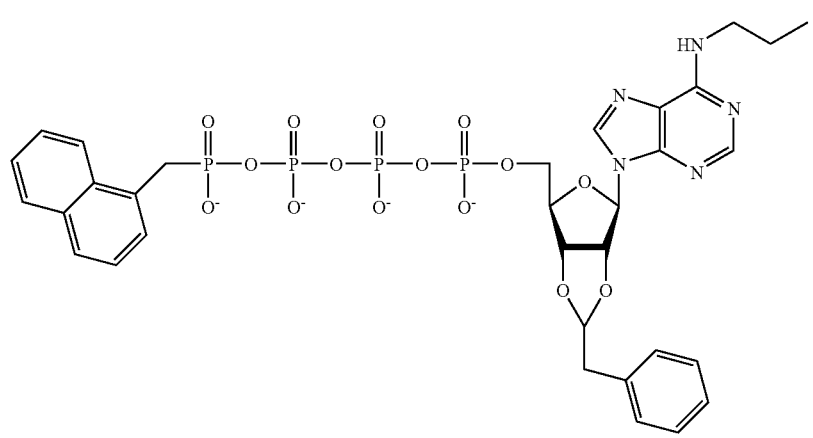

-continued
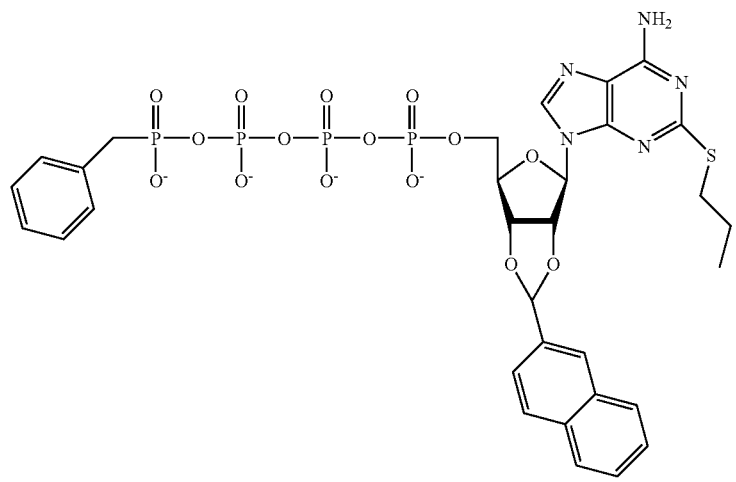
210
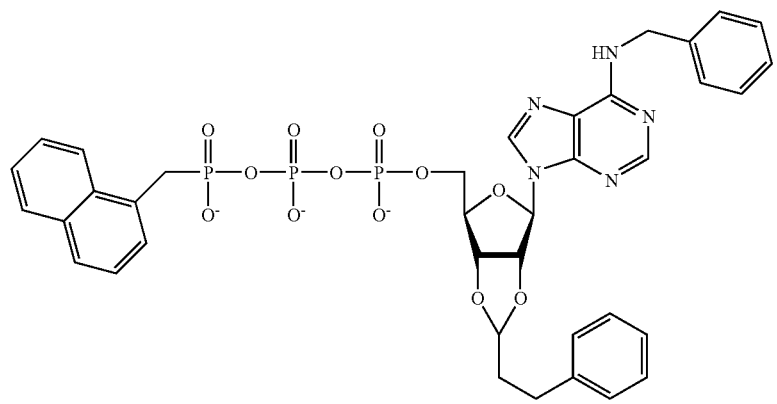
211
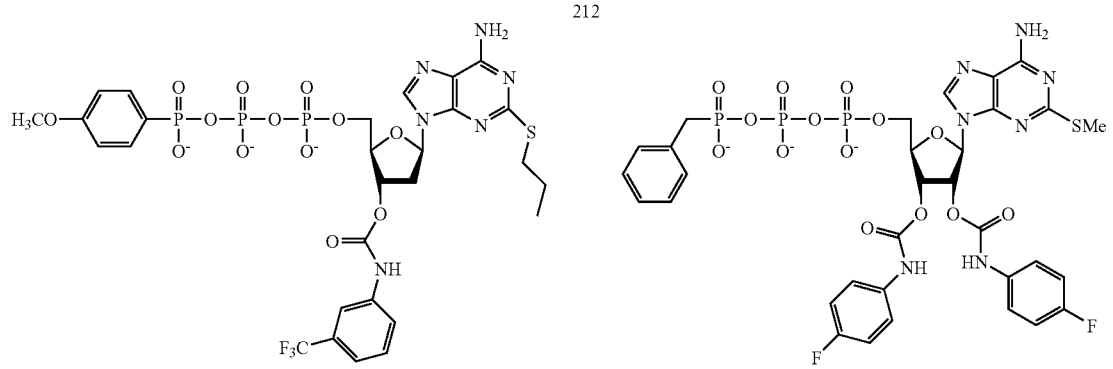
212 213
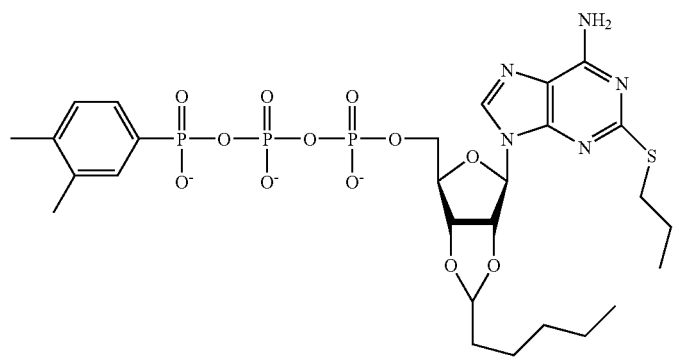
214

215
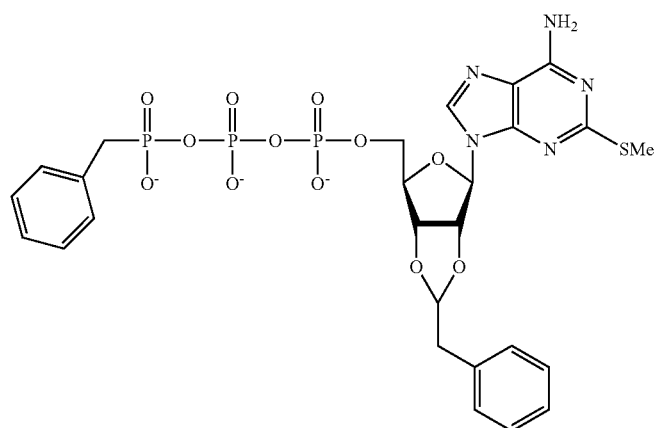
216
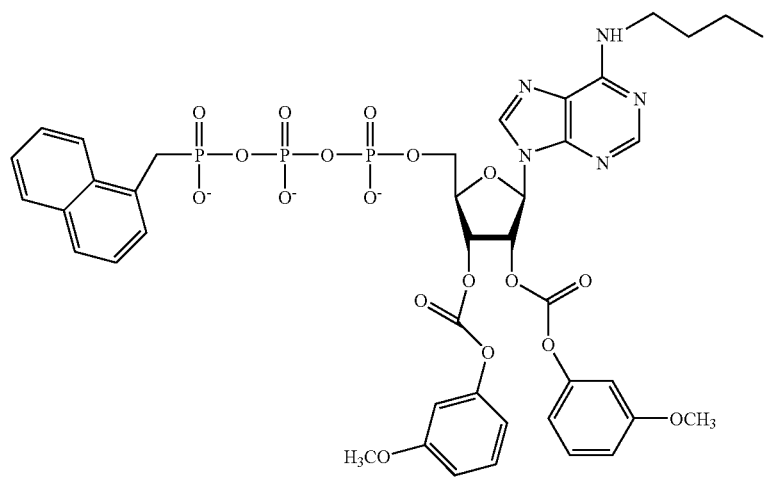
Structure 217 exemplifies adenosine monophosphates where A=OR$_1$ and structures 218-331 exemplify adenosine mono and diphosphates where A=CR$_1$R$_2$R$_3$:
217 218
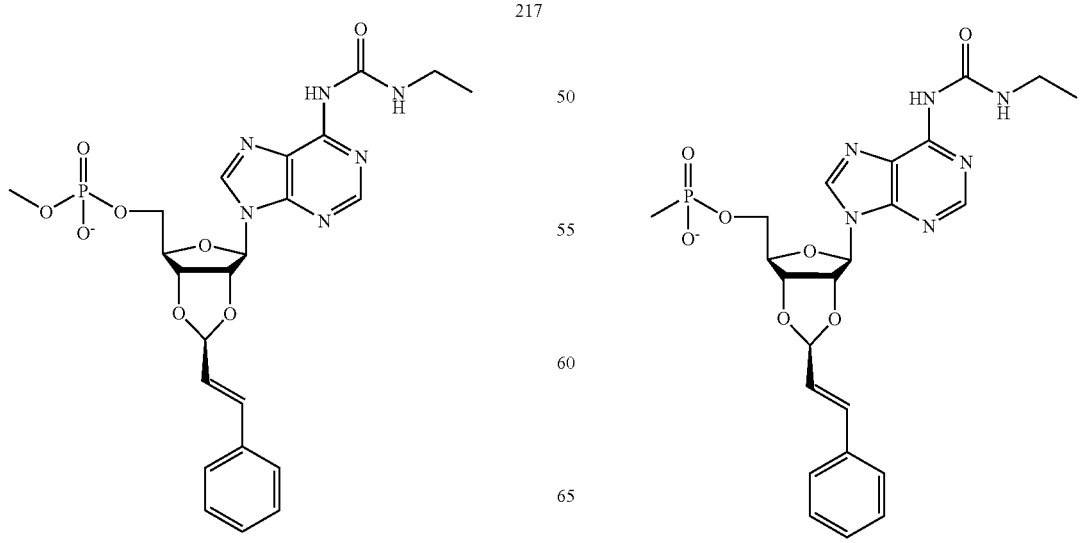

-continued
219
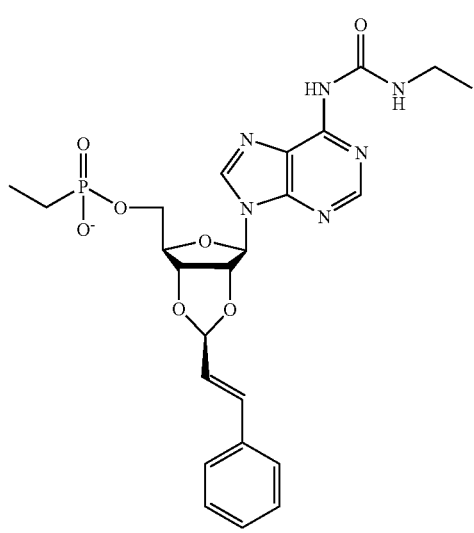
220
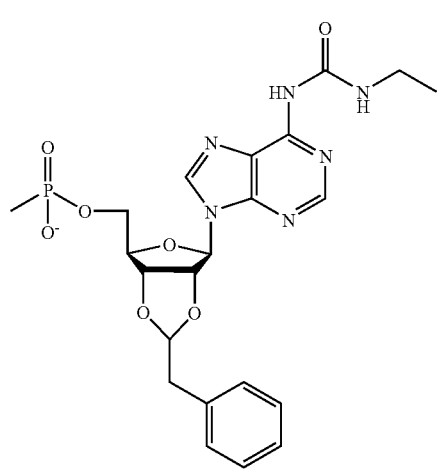
221
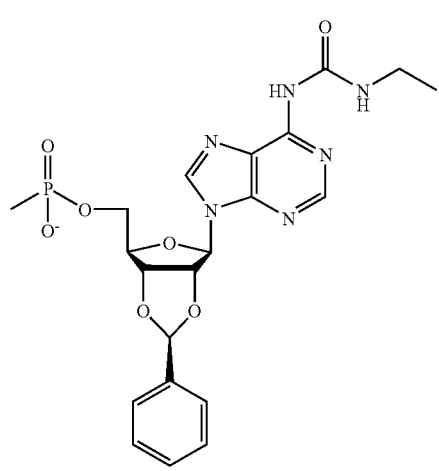
-continued
222
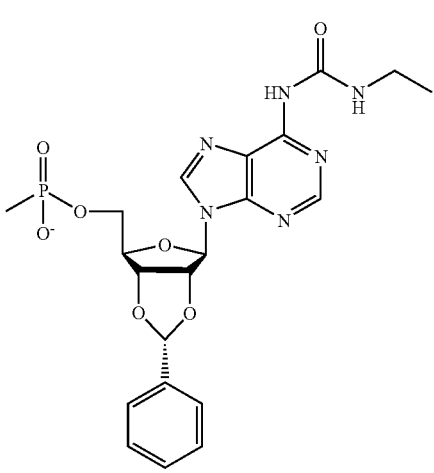
223
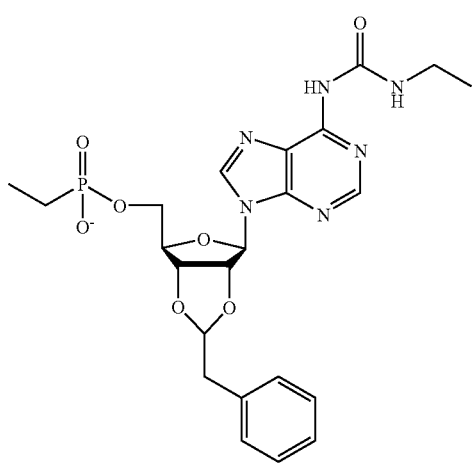
224
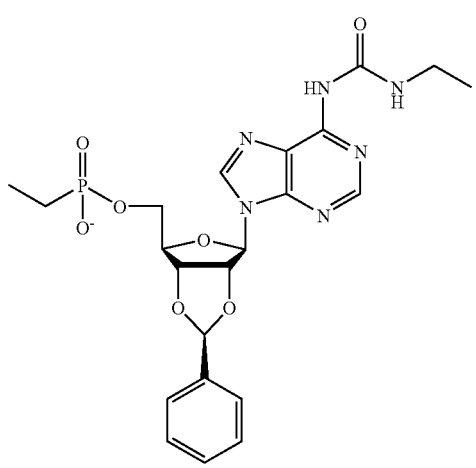

-continued
225
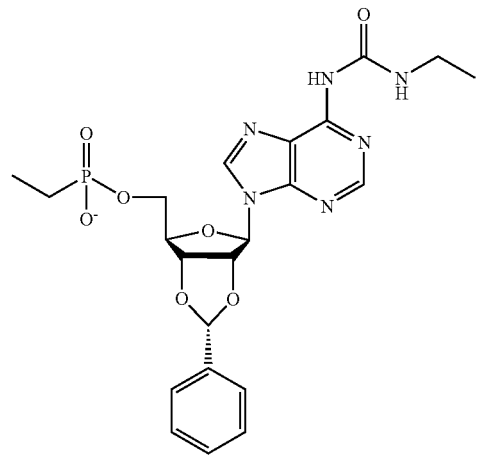
226
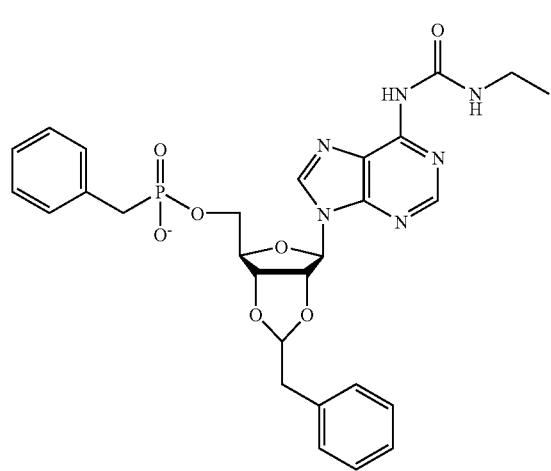
227
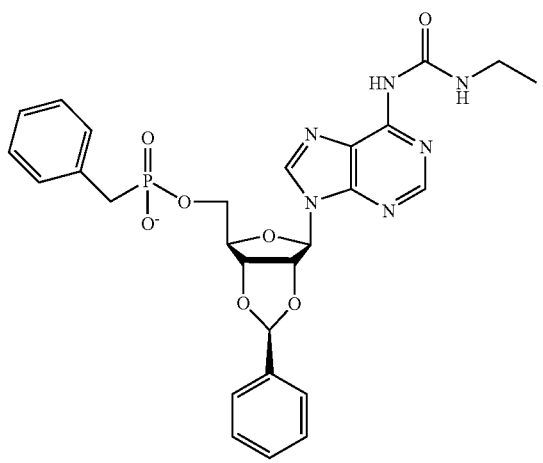
-continued
228
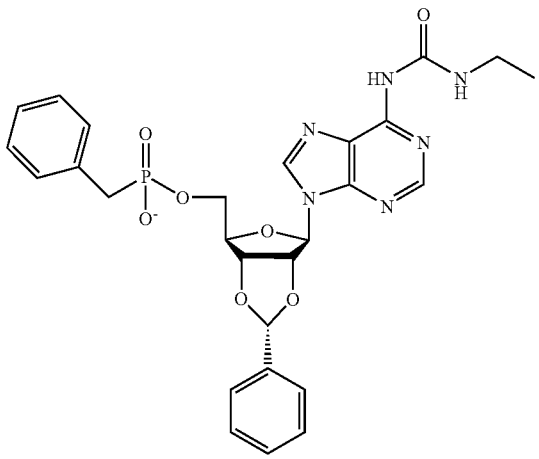
229
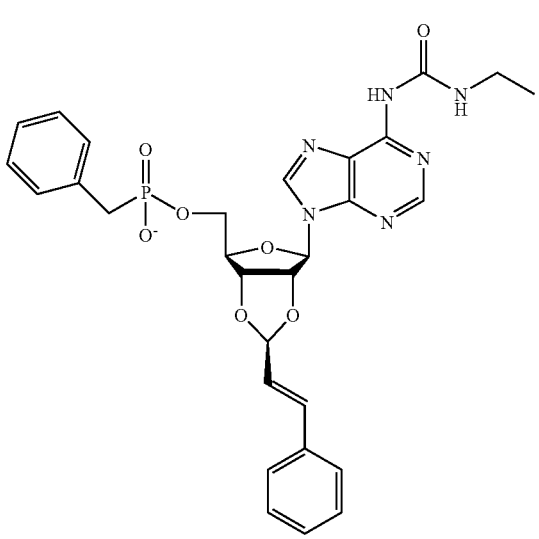
230
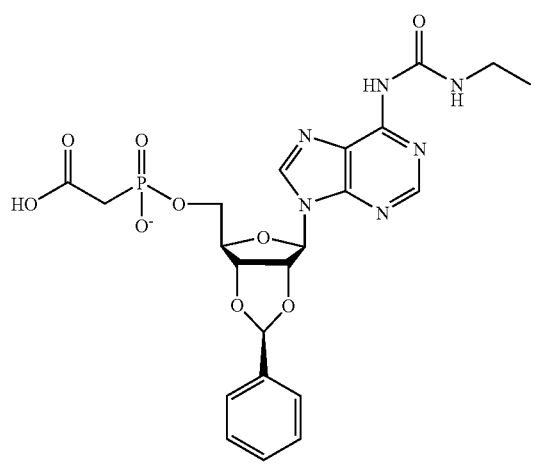

-continued
231
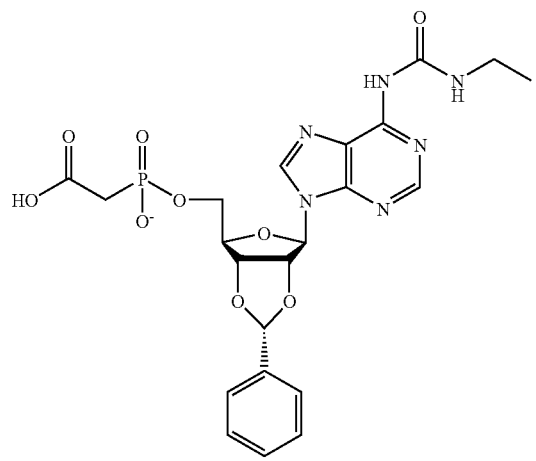
232
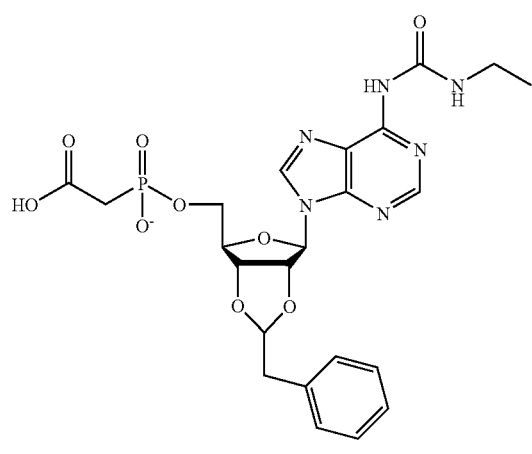
233
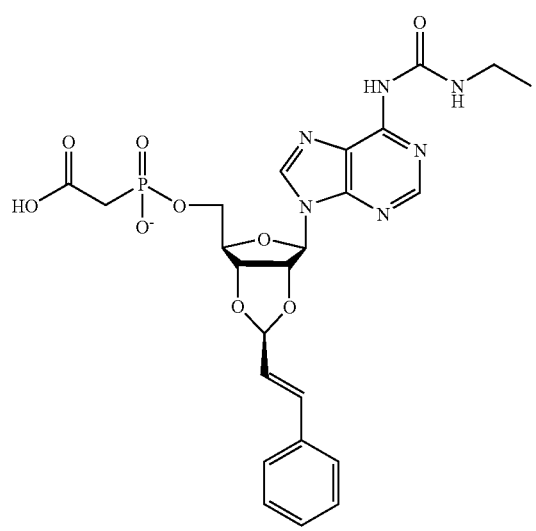
-continued
234
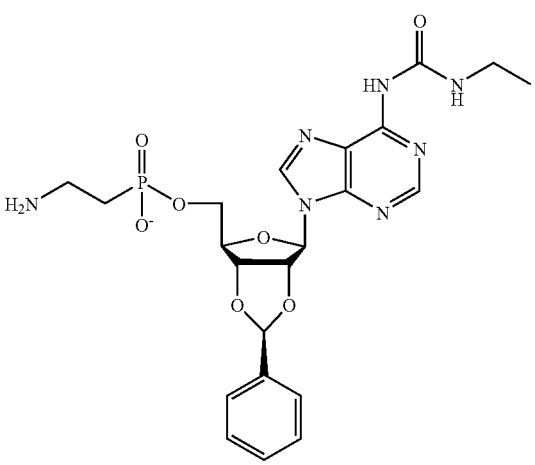
235
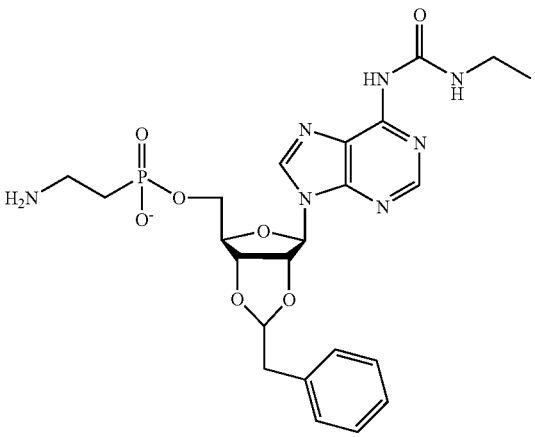
236

103
-continued
237
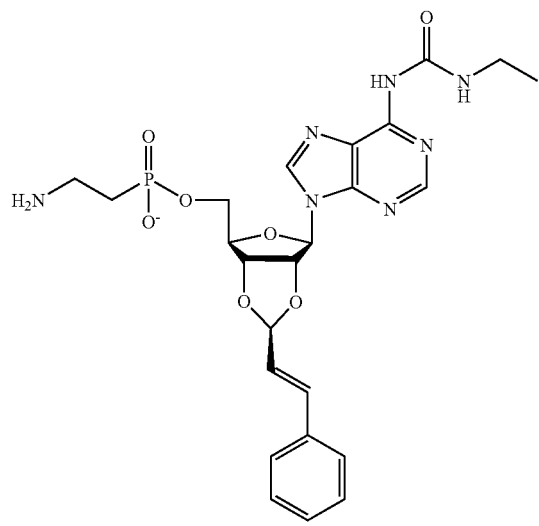
238
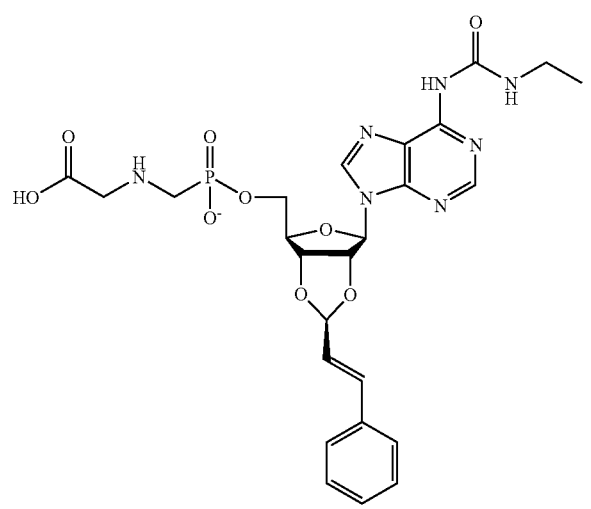
239
104
-continued
240
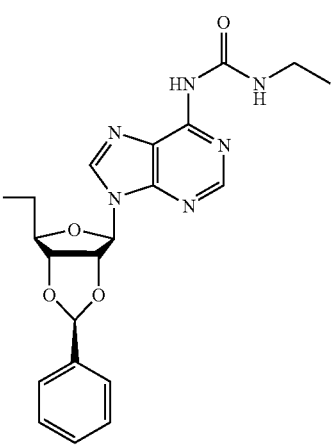
241
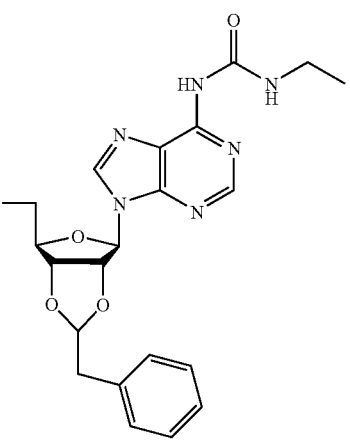
242

-continued
243
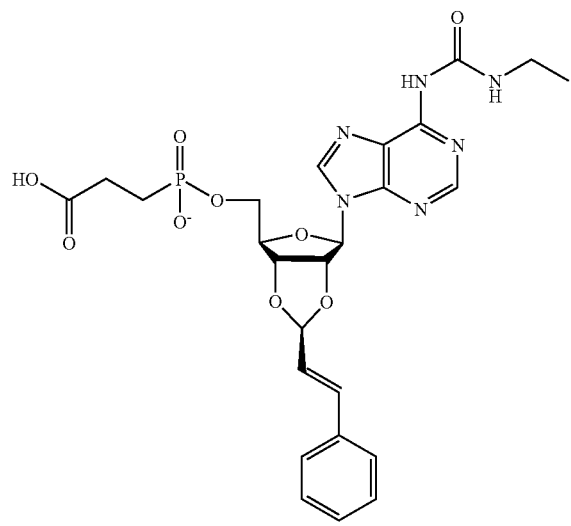
244
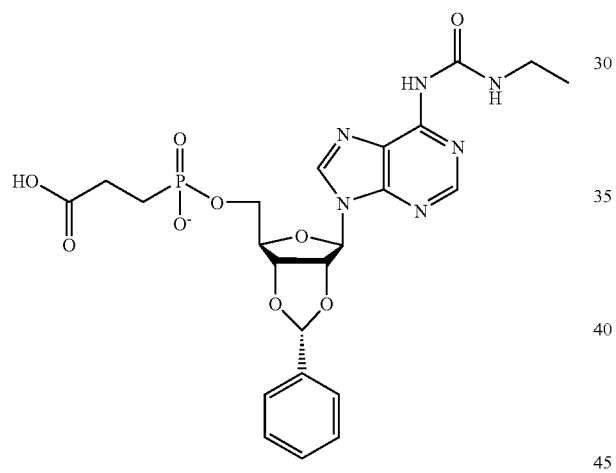
245
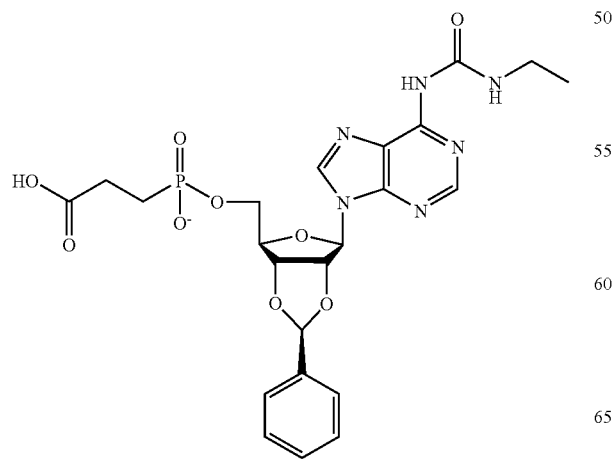
-continued
246
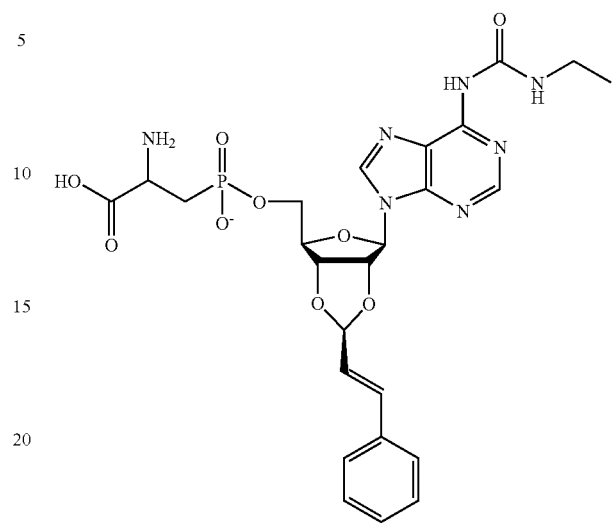
247
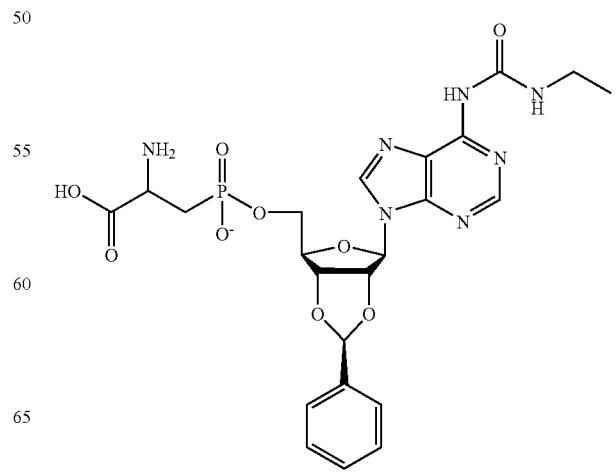
248

249
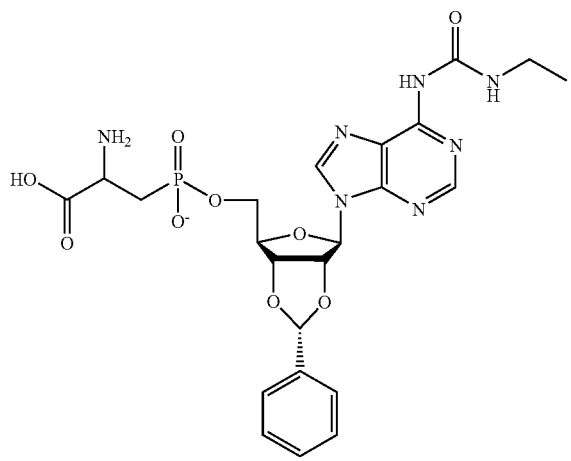
250
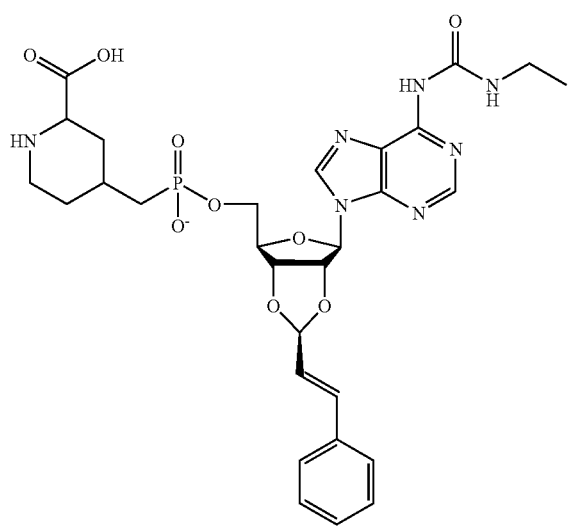
251
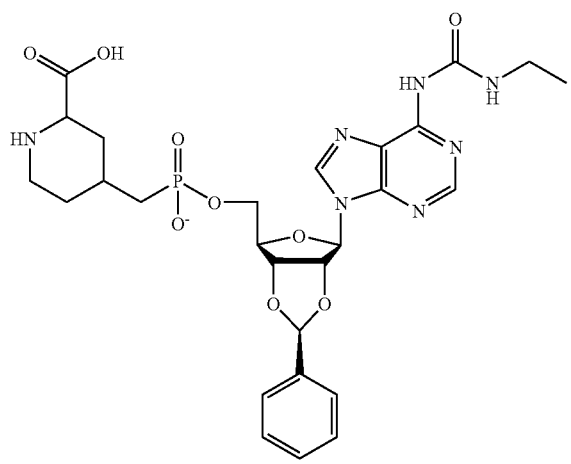
252
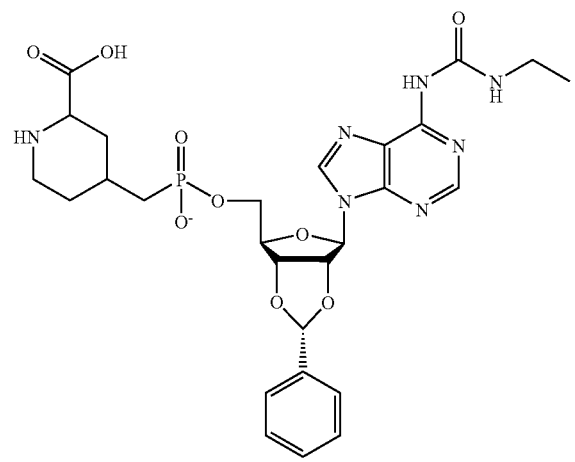
253
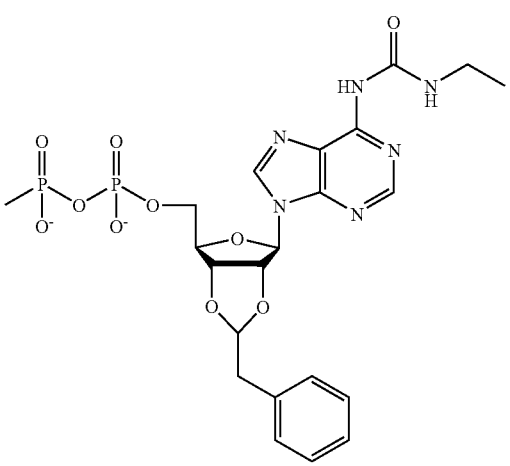
254
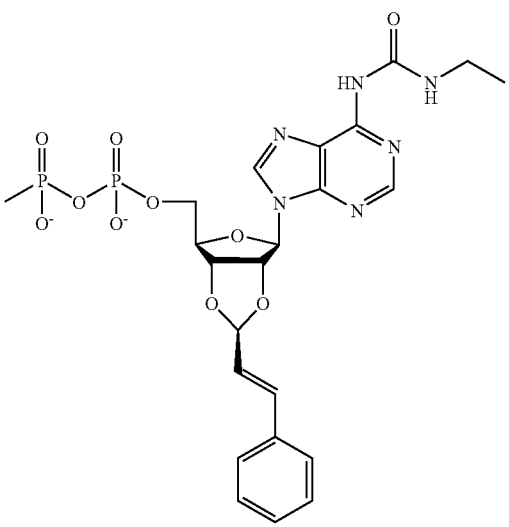

255
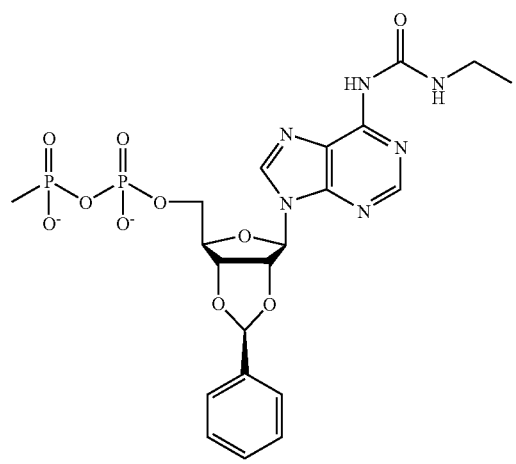
256
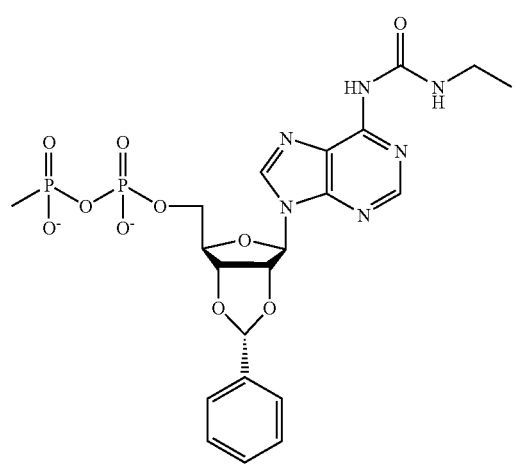
257
258
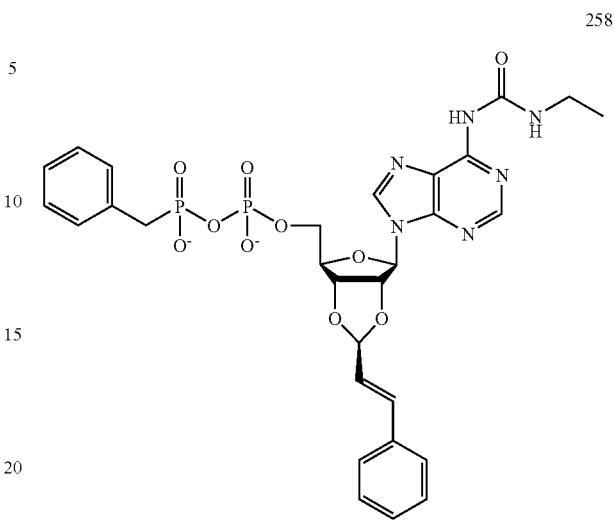
259
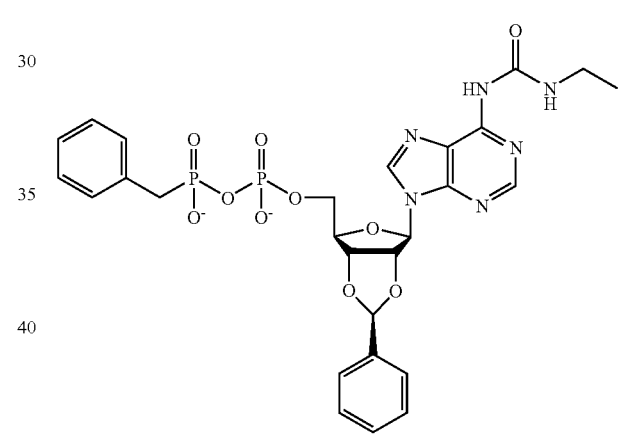
260
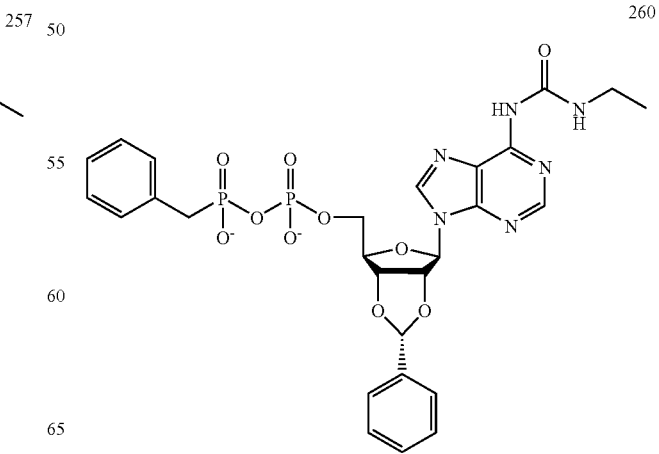

261
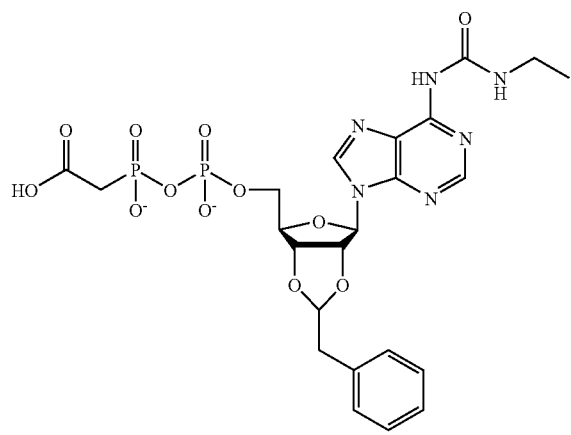
264
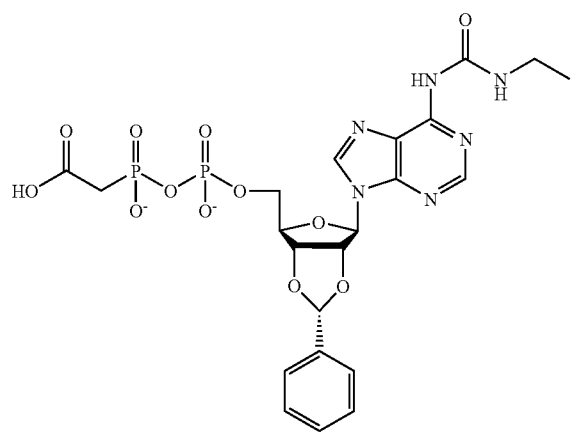
262
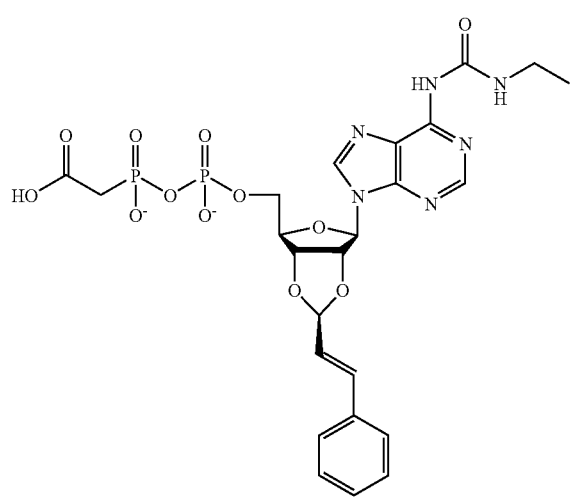
266
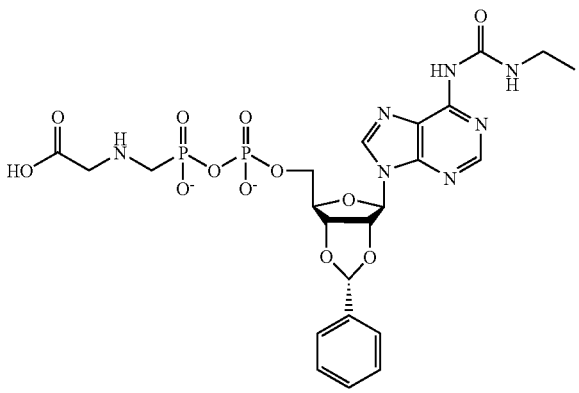
263
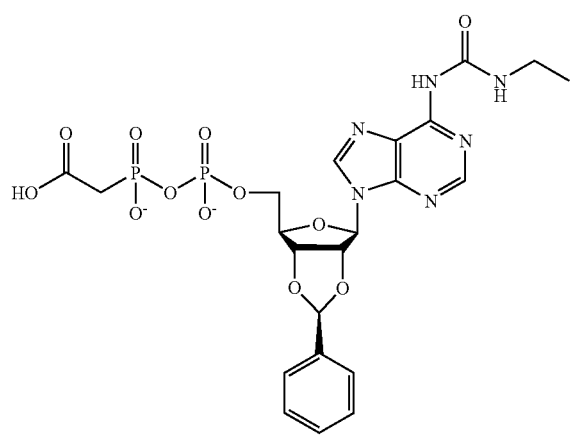
267

268
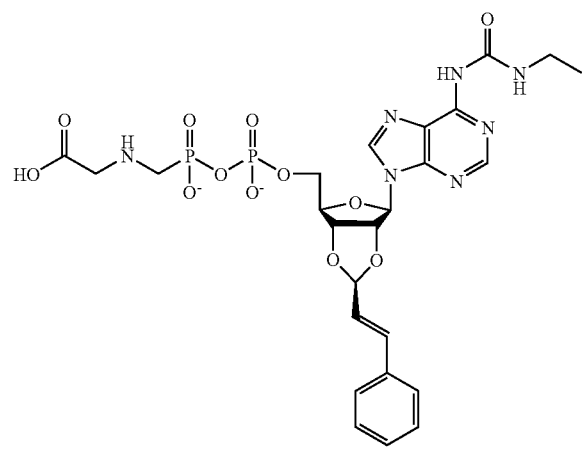
269
271
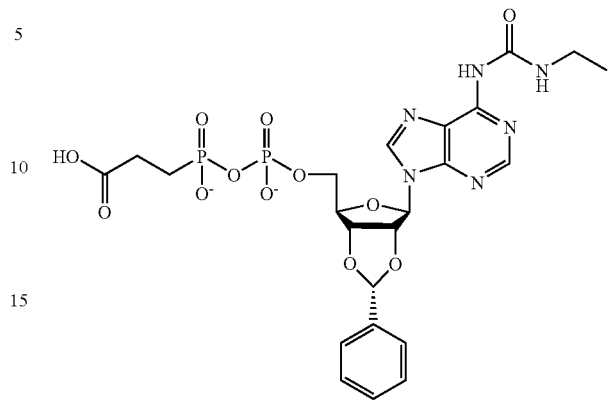
272
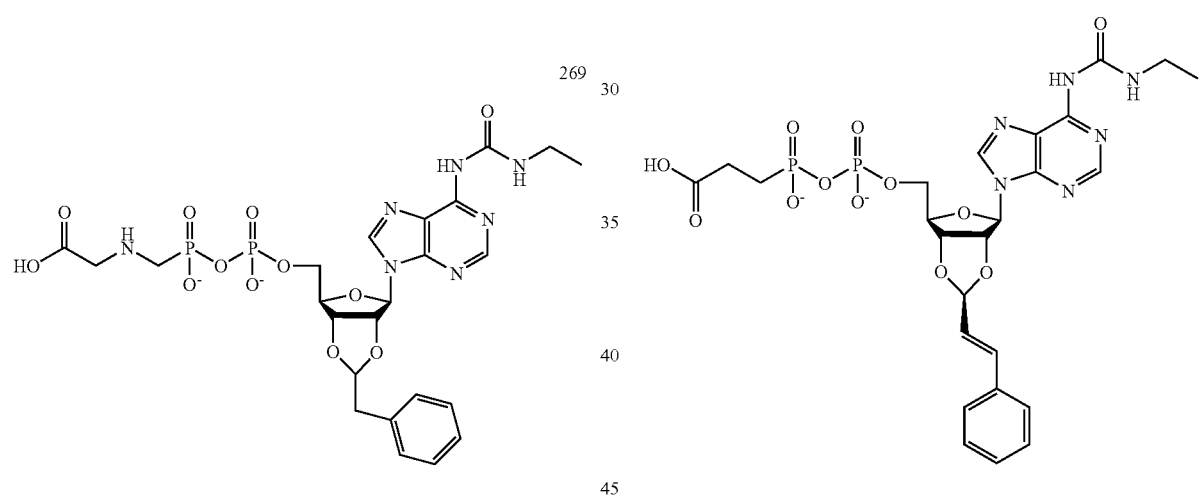
270
273
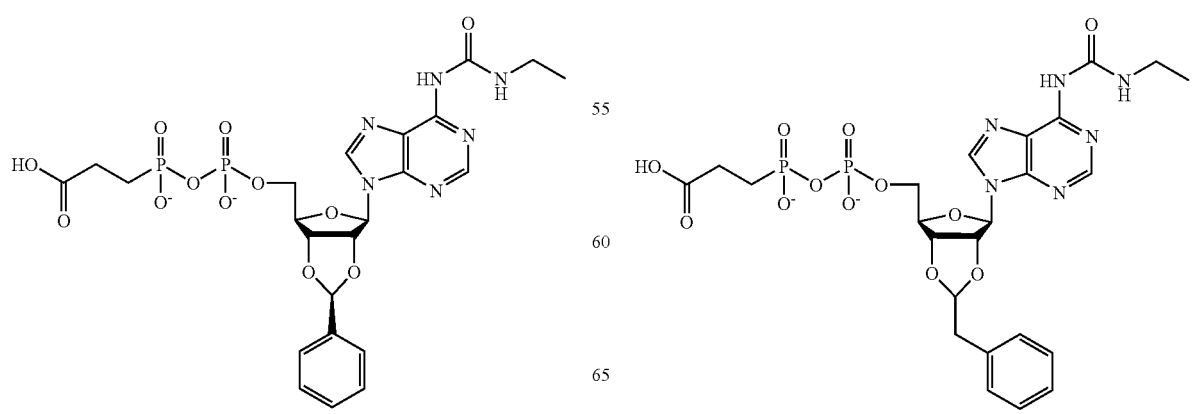

274
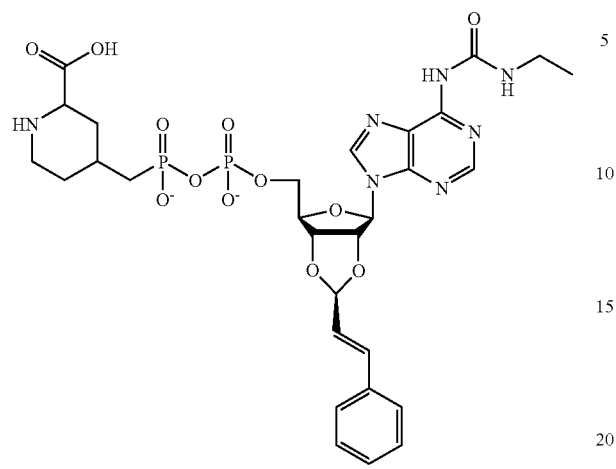
275
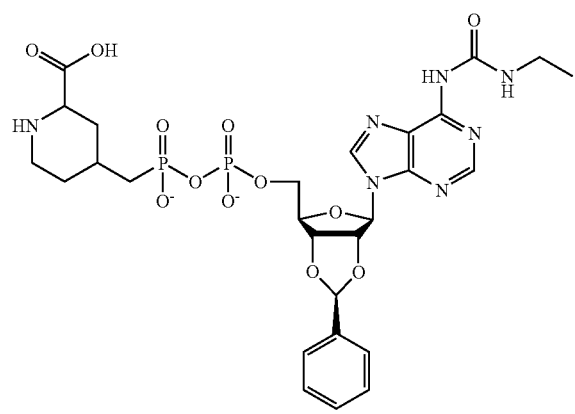
277
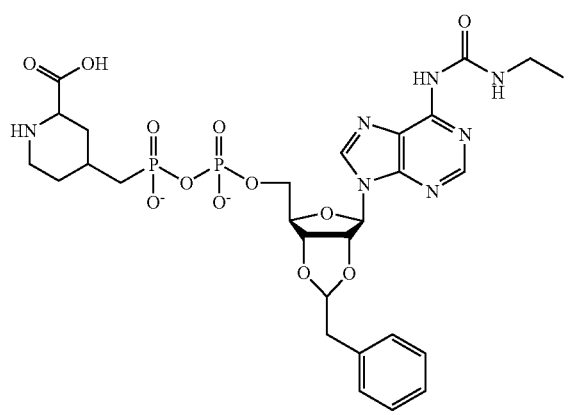
278
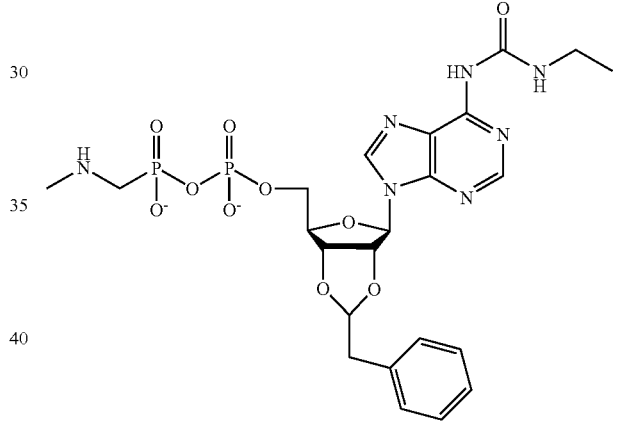
276
279
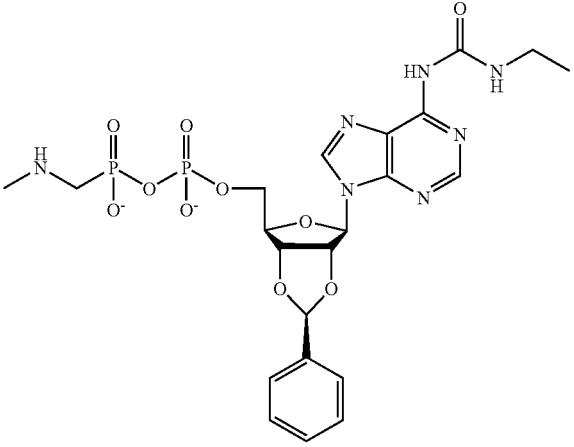

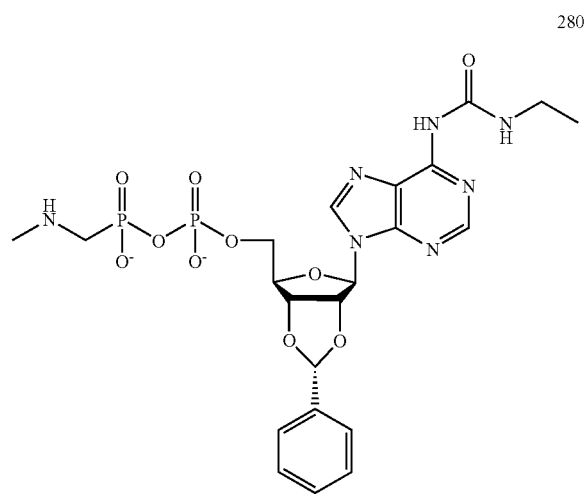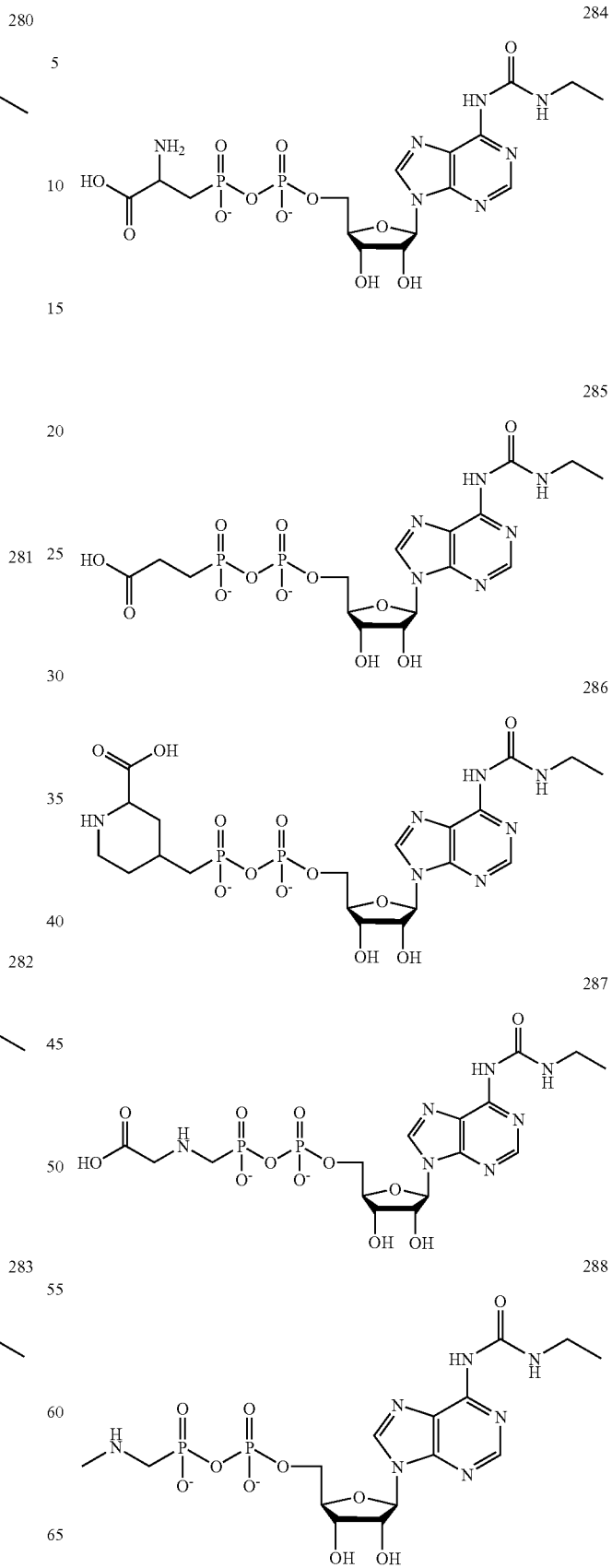

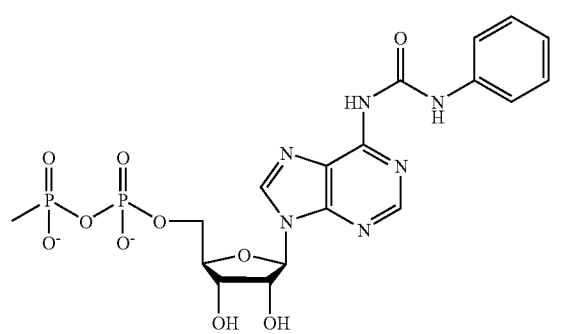
289
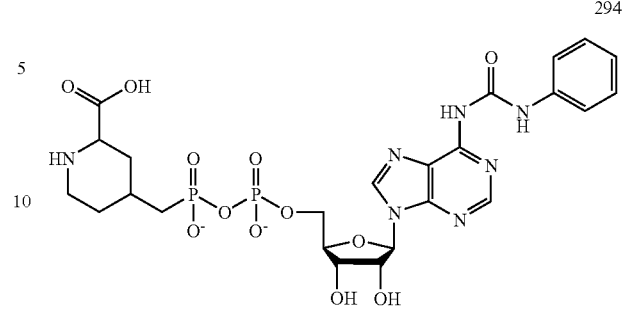
294
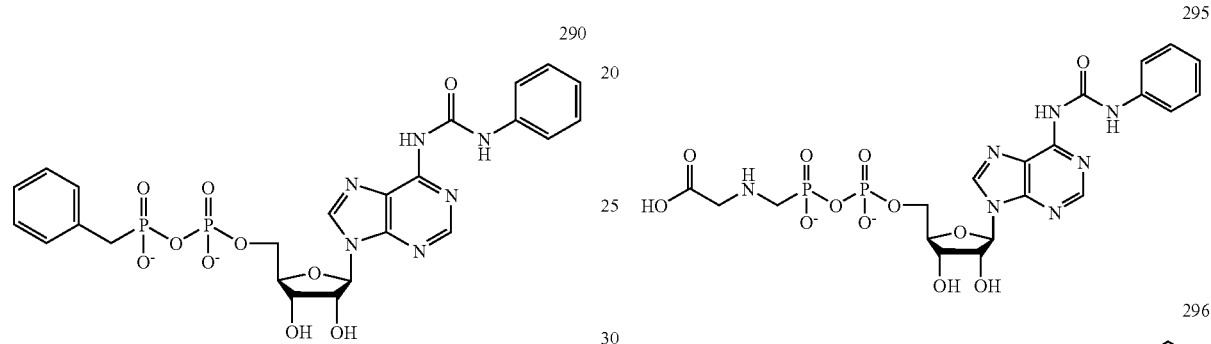
290
295
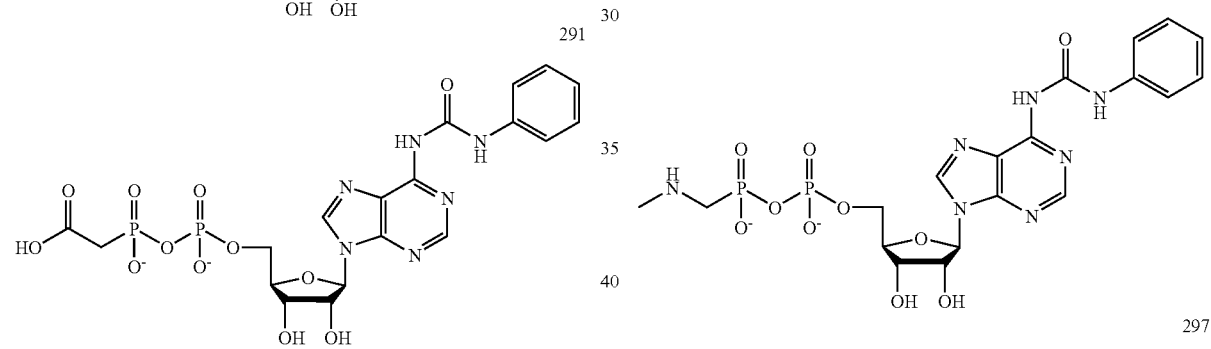
291
296
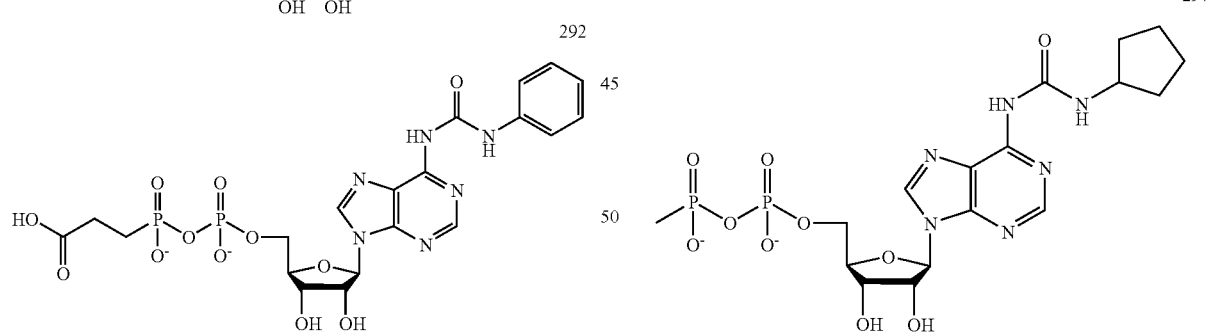
292
297
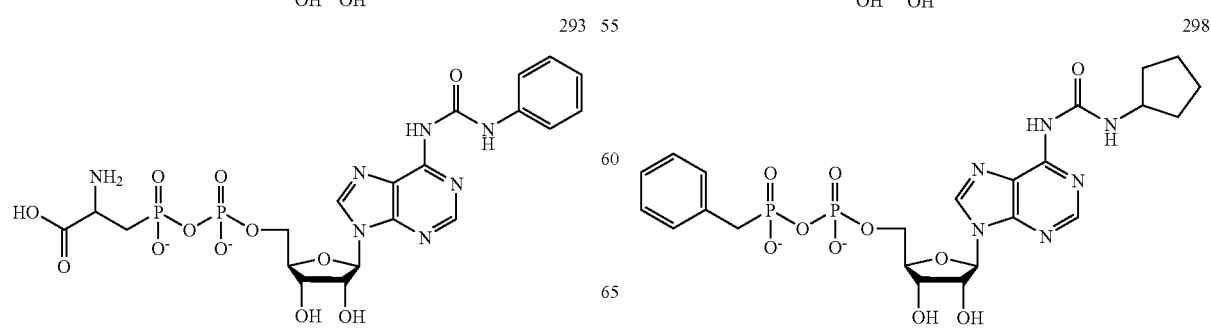
293
298

121 122
-continued
299
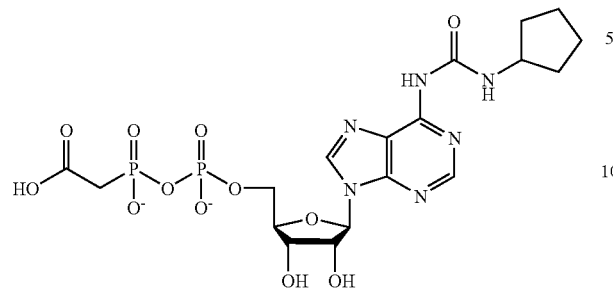
300
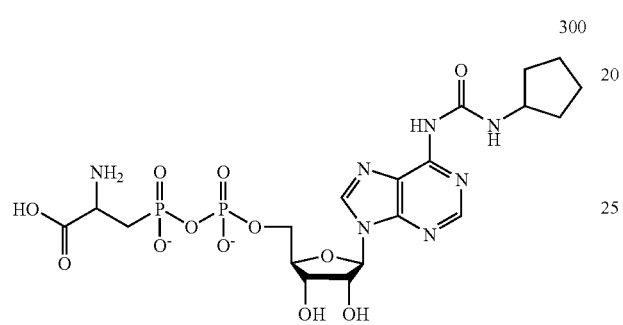
301
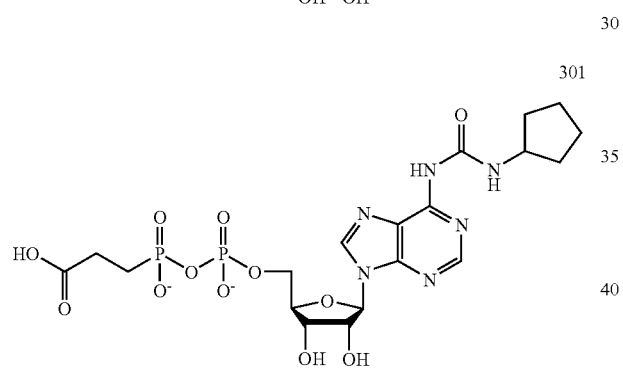
302
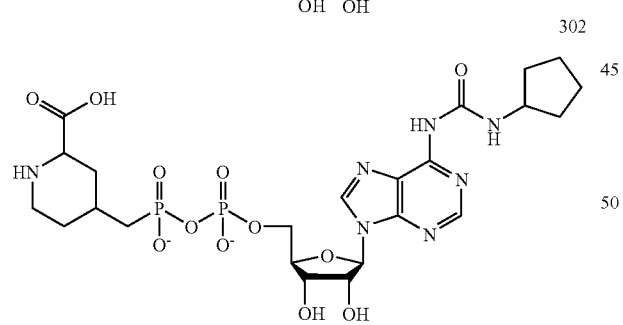
303
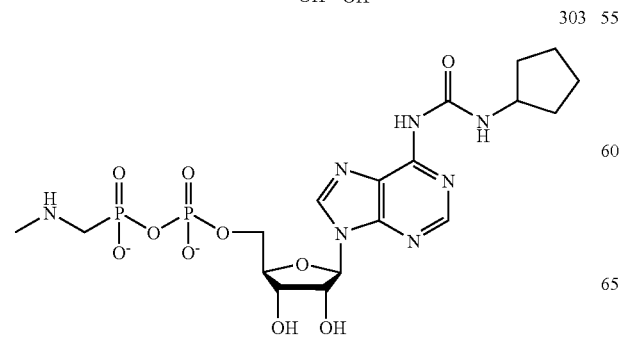
-continued
304
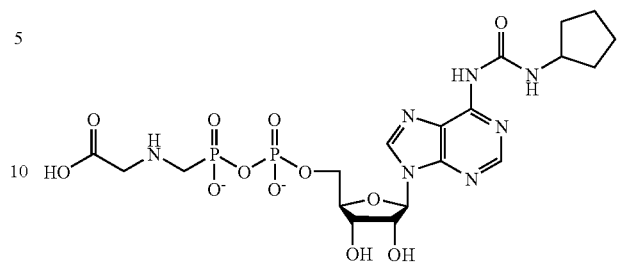
305
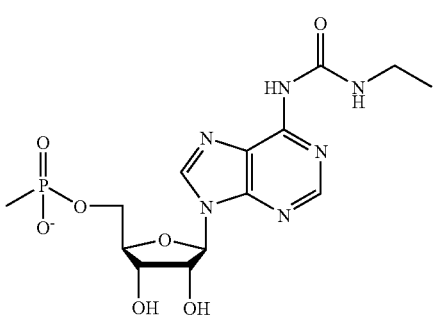
306
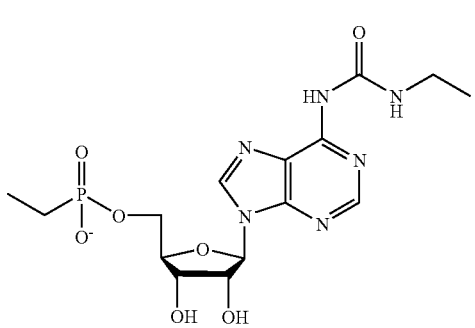
307
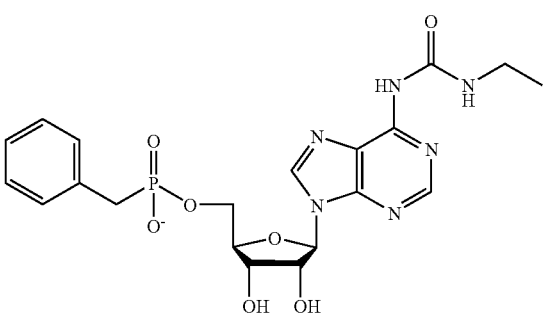
308
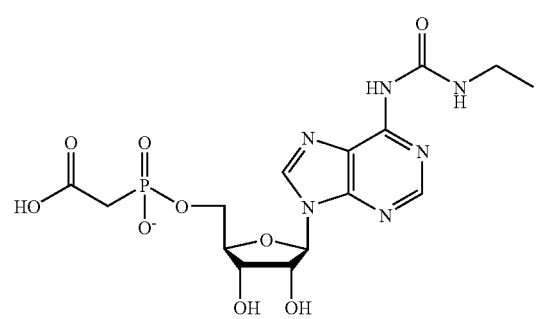

123
-continued
309
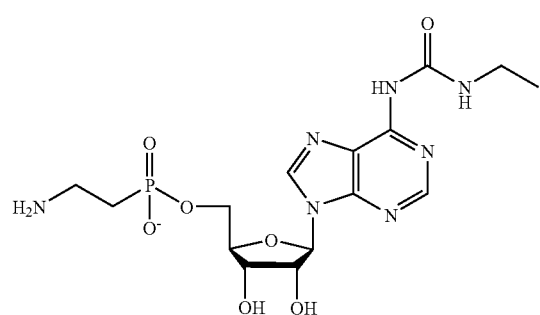
310
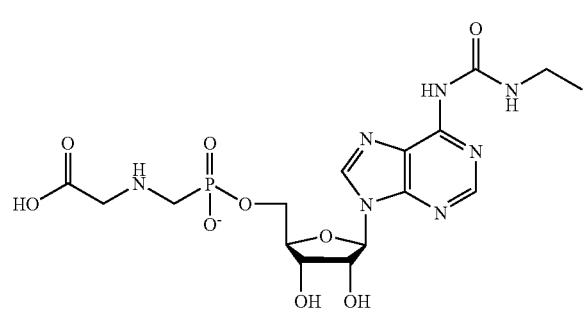
311
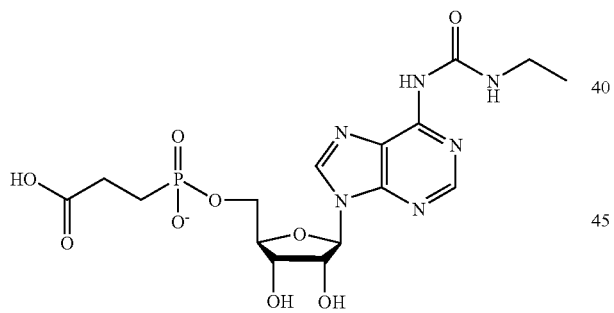
312
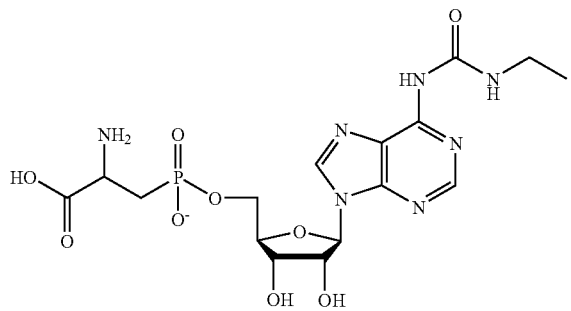
124
-continued
313
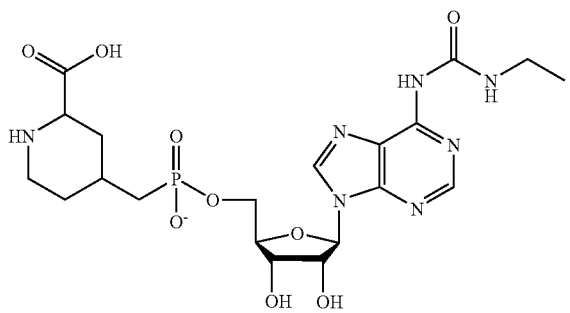
314
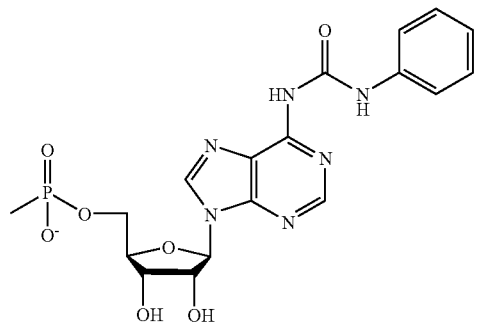
315
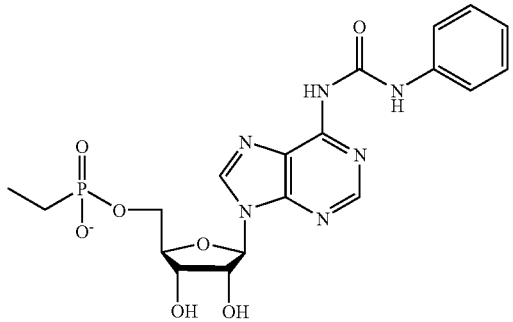
316
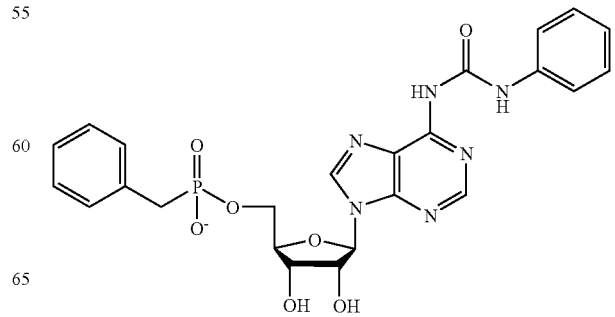

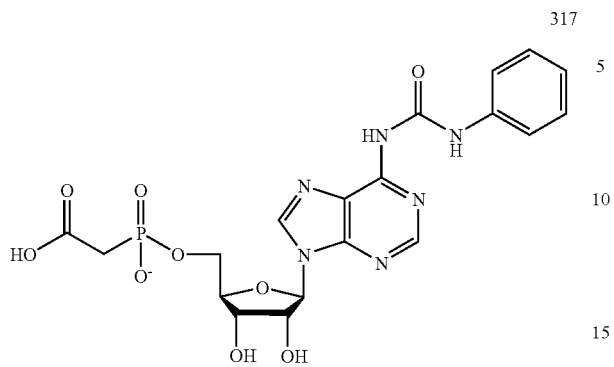
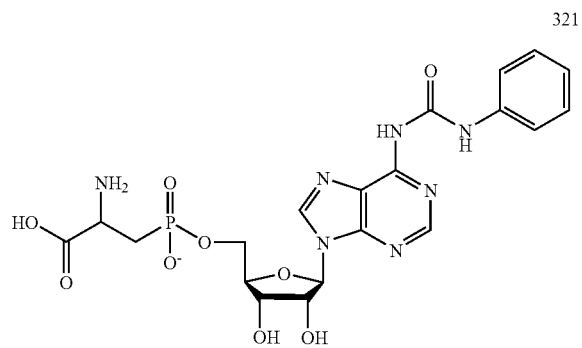

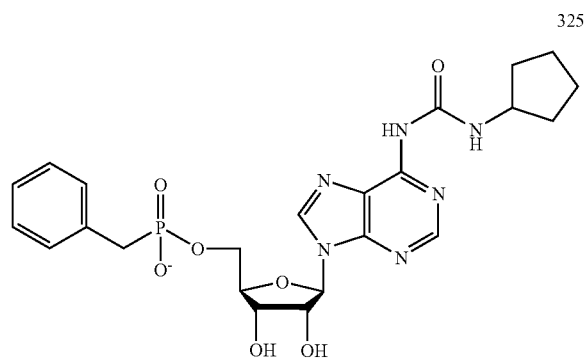

325

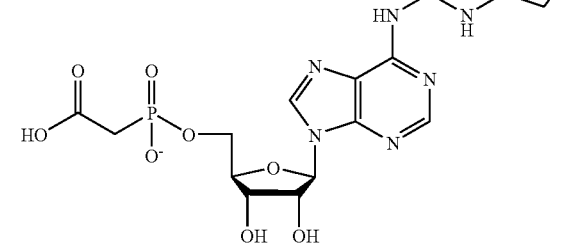

326

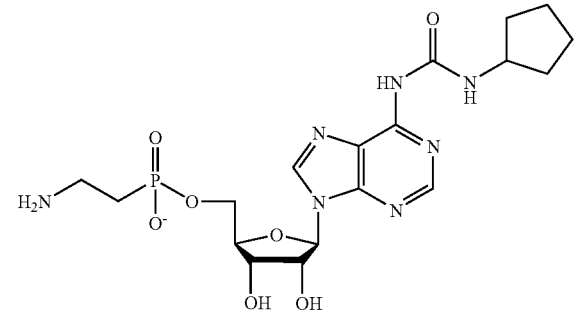

327

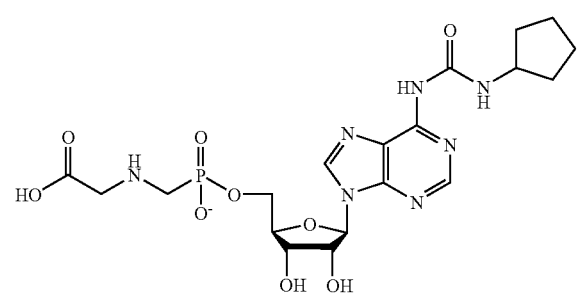

328

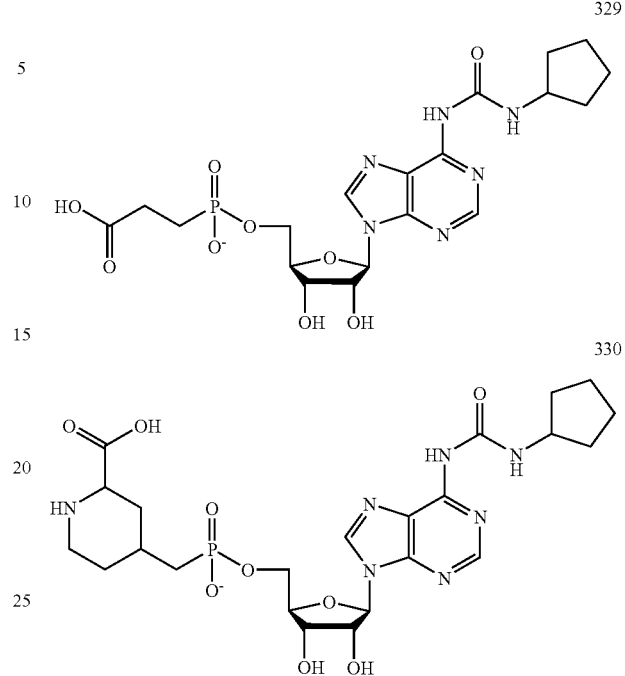

329

330

331

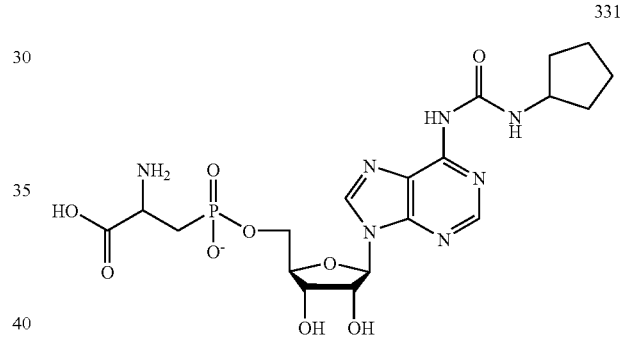

Preferred compounds from the structures 1-216 include: 2',3'-O-methylenebenzyl β-(cyclohexyl) UDP (5), 2'-phenylcarbamoyl β-benzyl UDP (14), 2'-(phenoxy)formyl β-propyl UDP (15), 6-phenyl-furanopyrimidine riboside β-(3-carboxyphenyl)methyl diphosphate (20), 4-thiobenzyl pyrimidine riboside β-benzyl diphosphate (21), 2',3'-dibenzoyl β-propyl UDP (29), 5-(3-methoxyphenyl)ethenocytosine 2'-deoxy-3'-phenylcarbamoyl riboside β-propyl diphosphate (33), $N^4$-propyl-2',3'-dibenzoyl β-benzyl CDP (36), 2',3'-O-methylenebenzyl β-(2-methylpropylphosphono) UDP (37), 2'-phenylcarbamoyl β-(2-carboxyethylphosphono) UDP (48), $N^4$-(4-fluorophenylcarbamoyl) β-(o-methylbenzylphosphono) CDP (54), 2',3'-di(phenoxy)formyl β-(pentylphosphono) UDP (61), $N^4$-propyl-2',3'-dibenzoyl β-(2-carboxyethylphosphono) CDP (72), 2'-deoxy γ-benzyl UTP (77), γ-(thiocyclohexyl) UTP (79), 6-(3-methylphenyl)-furanopyrimidine riboside δ-(2-naphthalenemethyl) tetraphosphate (86), 2',3'-O-methylenebenzyl γ-propyl UTP (93), 5-(3-methylphenyl)ethenocytosine 2',3'-O-methylenebenzyl riboside δ-propyl tetraphosphate (105), 5-(3-methoxyphenyl)ethenocytidine riboside γ-(2-naphthalenemethyl) triphosphate (111), $N^4$-(benzyloxyformyl)-2'-deoxy γ-benzyl CTP (115), $N^4$,3'-dibenzoyl-2'-deoxy γ-(2-naphthalmethyl) CTP (123), 5-(3-trifluoromethylphenyl)ethenocytidine γ-(1-naphthalenemethylphosphono) triphosphate (135), 4-thiopropyl pyrimidine riboside γ-(4-aminocarboxybutylphosphono) triphosphate (138), 2',3'-O-methylenephenethyl γ-(3,4-dimethylphenylphosphono) UTP (147), 5-iodo-2',3'-O-methylenebutyl γ-(1-naphthalenemethylphosphono) UTP (157), 2',3'-dibenzoyl δ-(4-ethoxyphenylphosphono) uridine tetraphosphate (161), 2',3'-O-methylenebenzyl γ-(2-naphthalene) ATP (175), 2-thiopropyl-2',3'-O-methylenebenzyl γ-benzyl ATP (180), 2-thiomethyl-N⁶-propyl-2',3'-O-methylenebenzyl γ-(2-naphthalene) ATP (183), 2',3'-O-methylenebenzyl γ-anilino ATP (192), 2',3'-O-methylenebenzyl γ-(carboxymethylphosphono) ATP (200), 2',3'-O-methylenebenzyl δ-(1-naphthalene) adenosine tetraphosphate (201), 2-thiopropyl-2'-deoxy-3'-(3-trifluoromethylphenyl)carbamoyl γ-(4-methoxyphenylphosphono) ATP (212).

The following compounds are more preferred: 2',3'-O-methylenebenzyl β-(cyclohexyl) UDP (5), 5-(3-methoxyphenyl)ethenocytosine 2'-deoxy-3'-phenylcarbamoyl riboside β-propyl diphosphate (33), 2',3'-O-methylenebenzyl β-(2-methylpropylphosphono) UDP (37), 2',3'-di(phenoxy) formyl β-(pentylphosphono) UDP (61), 2',3'-O-methylenebenzyl γ-(propyl) UTP (93), 5-(3-methylphenyl)ethenocytosine 2',3'-O-methylenebenzyl riboside δ-propyl tetraphosphate (105), 5-(3-trifluoromethylphenyl)ethenocytidiney-(1-naphthalenemethylphosphono) triphosphate (135), 2',3'-dibenzoyl δ-(4-ethoxyphenylphosphono) uridine tetraphosphate (161), 2-thiopropyl-2',3'-O-methylenebenzyl γ-benzyl ATP (180), and), 2',3'-O-methylenebenzyl δ-(1-naphthalene) adenosine tetraphosphate (201).

Preferred compounds from the structures 217-331 are: 2',3'-(trans)-O-methylenestyryl-5'-(methylphosphate)-N⁶-ethylaminocarbonyl-adenosine (217), 2',3'-(trans)-O-methylenestyryl-5'-(methylphosphono)-N⁶-ethylaminocarbonyl-adenosine (218), 2',3'-trans-O-methylenestyryl-5'-(ethylphosphono)-N⁶-ethylaminocarbonyl-adenosine (219), 2',3'-trans-O-methylenephenyl-5'-(ethylphosphono)-N⁶-ethylatinocarbonyl-adenosine (224), 2',3'-cis-O-methylenephenyl-5'-(ethylphosphono)-N⁶-ethylaminocarbonyl-adenosine (225), 2',3'-trans-O-methylenephenyl-5'-(benzylphosphono)-N⁶-ethylaminocarbonyl-adenosine (227), 2',3'-trans-O-methylenephenyl-5'-(carboxymethylenephosphono)-N⁶-ethylaminocarbonyl-adenosine (230), 2',3'-trans-O-methylenephenyl-5'-((carboxymethylene)amino)methylenephosphono)-N⁶-ethylaminocarbonyl-adenosine (240), 2',3'-trans-O-methylenephenyl-5'-(2-carboxyethylenephosphono)-N⁶-ethylaminocarbonyl-adenosine (245), 2',3'-trans-O-methylenephenyl-5'-[(4-(3-carboxy)piperidinyl)methylenephosphono]-N⁶-ethylaminocarbonyl-adenosine (251), 2',3'-trans-O-methylenestyryl-5'-α-(carboxymethylenephosphono)-N⁶-ethylaminocarbonyl-adenosine monophosphate (262), 2',3'-trans-O-methylenephenyl-5'-α-(carboxymethylenephosphono)-N⁶-ethylaminocarbonyl-adenosine monophosphate (263), 2',3'-trans-O-methylenephenyl-5'-α-((carboxymethylene)amino)methylenephosphono)-N⁶-ethylaminocarbonyl-adenosine monophosphate (266), 2',3'-trans-O-methylenestyryl-5'-α-((carboxymethylene)amino)methylenephosphono)-N⁶-ethylaminocarbonyl-adenosine monophosphate (268), 2',3'-trans-O-methylenephenyl-5'-α-[(4-(3-carboxy)piperidinyl)methylenephosphono]-N⁶-ethylaminocarbonyl-adenosine monophosphate (275), 5'-α-(benzylphosphono)-N⁶-ethylaminocarbonyl-adenosine monophosphate (282), 5'-α-(carboxymethylenephosphono)-N⁶-ethylaminocarbonyl-adenosine monophosphate (283), 5'-α-(carboxyethylenephosphono)-N⁶-ethylaminocarbonyl-adenosine monophosphate (285), 5'-α-((carboxymethylene)amino)methylenephosphono)-N⁶-ethylaminocarbonyl-adenosine monophosphate (287), 5'-α-(carboxymethylenephosphono)-N⁶-phenylaminocarbonyl-adenosine monophosphate (291), 5'-α-(carboxyethylenephosphono)-N⁶-phenylaminocarbonyl-adenosine monophosphate (292), 5'-α-((carboxymethylene)amino)methylenephosphono)-N⁶-phenylaminocarbonyl-adenosine monophosphate (295), 5'-α-(carboxymethylenephosphono)-N⁶-cyclopentylaminocarbonyl-adenosine monophosphate (299), 5'-α-[(4-(3-carboxy)piperidinyl)methylenephosphono]-N⁶-cyclopentylaminocarbonyl-adenosine monophosphate (302), 5'-((carboxymethylene)amino)methylenephosphono)-N⁶-ethylaminocarbonyl-adenosine (310), 5'-(carboxyethylenephosphono)-N⁶-ethylaminocarbonyl-adenosine (311), 5'-(carboxymethylenephosphono)-N⁶-phenylaminocarbonyl-adenosine (317), 5'-((carboxymethylene)amino)methylenephosphono)-N⁶-phenylaminocarbonyl-adenosine (319), 5'-(carboxymethylenephosphono)-N⁶-cyclopentylaminocarbonyl-adenosine (326), 5'-((carboxymethylene)amino)methylenephosphono)-N⁶-cyclopentylaminocarbonyl-adenosine (328), 5'-(carboxyethylenephosphono)-N⁶-cyclopentylaminocarbonyl-adenosine (329), 5'-[(4-(3-carboxy)piperidinyl)methylenephosphono]-N⁶-cyclopentylaminocarbonyl-adenosine (330).

The invention is illustrated further by the following examples that are not to be construed as limiting the invention in scope to the specific procedures described in them.

EXAMPLES

Example 1

γ-(n-propyl)-uridine 5'-triphosphate

Uridine 5'-triphosphate, ditributylammonium salt (106 mg, 0.124 mmol) dissolved in dry N,N dimethylformamide (400 uL) was treated with N,N'-dicyclohexlycarbodiimide (33.4 mg, 0.162 mmol) for one hour at room temperature. After verifying that there was complete conversion to the cyclical trimetaphosphate by $^{31}$P NMR, tributylamine (88 μL, 0.373 mmol) and excess n-propanol (1 mL) were added and the reaction mixture heated to 65° C. for 2.5 days. HPLC (AX300, gradient from 75% water/25% acetonitrile to 75% 0.5 M KH2PO4 over 20 min, 1 mL/min, monitor at 260 nm) showed >90% conversion to product, so the solvents were removed on a rotary evaporator. The product was purified by semi-preparative HPLC (AX300, gradient from 75% water/25% acetonitrile to 75% 1 M ammonium acetate/25% acetonitrile over 20 min, 2 mL/min, monitor at 260 μm) yielding 19.5 mg (28%) of the title product.

$^1$H NMR (D$_2$O, 300 MHz): δ 7.78 (d, 1H), 5.79 (m, 2H), 4.19 (M, 2H), 4.04 (m, 3H), 3.73 (q, 2H), 1.46 (m, 2H), 0.72 (t, 3H). $^{31}$P NMR (D$_2$O, 121.47 MHz): δ −9.60 (d, 1P), −10.34 (d, 1P), −21.98 (t, 1P).

Example 2

γ-(2-propyl)-uridine 5'-triphosphate

The title product was obtained from the reaction between uridine 5'-triphosphate and 2-propyl alcohol, according to the method of example 1. Yield=14%.

$^1$H NMR (D$_2$O, 300 MHz): δ 7.80 (d, 1H), 5.81 (m, 2H), 4.23 (M, 1H), 4.11 (m, 2H), 4.07 (m, 3H), 1.10 (d, 6H). $^{31}$P NMR (D$_2$O, 121.47 MHz): δ −9.60 (d, 1P), −10.34 (d, 1P), −21.98 (t, 1P).

Example 3

γ-(n-butyl)-uridine 5'-triphosphate

The title product was obtained from the reaction between uridine 5'-triphosphate and n-butyl alcohol, according to the method of example 1. Yield=39%.

$^1$H NMR (D$_2$O, 300 MHz): δ 7.82 (d, 1H), 5.83 (m, 2H), 4.22 (M, 1H), 4.11 (m, 3H), 3.80 (q, 2H), 1.46 (t, 2H), 1.21 (q, 2H), 0.72 (t, 3H). $^{31}$P NMR (D$_2$O, 121.47 MHz): δ −9.44 (d, 1P), −10.18 (d, 1P), −21.82 (t, 1P).

Example 4

γ-(n-hexyl)-uridine 5'-triphosphate

The title product was obtained from the reaction between uridine 5'-triphosphate and n-hexyl alcohol, according to the method of example 1. Yield=12%.

$^1$H NMR (D$_2$O, 300 MHz): δ 7.80 (d, 1H), 5.81 (d, 2H), 4.20 (M, 2H), 4.11 (m, 3H), 3.78 (q, 2H), 1.41 (t, 2H), 1.09 (q, 6H), 0.68 (t, 3H). $^{31}$P NMR (D$_2$O, 121.47 MHz): δ −9.58 (d, 1P), −10.22 (d, 1P), −21.68 (t, 1P).

Example 5

γ-(farnesyl)-uridine 5'-triphosphate

The title product was obtained from the reaction between uridine 5'-triphosphate and farnesol (as a mixture of isomers), according to the method of example 1. Yield=8%.

$^1$H NMR (D$_2$O, 300 MHz): δ 7.78 (d, 1H), 5.87 (d, 2H), 5.22 (m, 1H), 4.98 (m, 2H), 4.23 (m, 2H), 4.18 (m, 3H), 4.01 (m, 2H), 1.81 (t, 8H), 1.24 (d, 12H). $^{31}$P NMR (D$_2$O, 121.47 MHz): δ −9.69 (d, 1P), −10.18 (d, 1P), −21.88 (t, 1P).

Example 6

γ-(cholesteryl)-uridine 5'-triphosphate

The title product is obtained from the reaction between uridine 5'-triphosphate and cholesterol, according to the general method of example 1. If necessary, this process can be enhanced by the addition of catalysts such as pyridine, 4-dimethylaminopyridine, diazabicycloundecene (DBU) and the like.

As demonstrated in the preceding examples 1-6, different nucleophiles can be used to open the cyclical trimetaphosphate, giving derivatives with unique substituents on the γ phosphate. Thus, for example, the activated triphosphate can be reacted with 2-naphthylmethyl alcohol to give structure 91, or with cyclohexylmethyl alcohol to give 78. Alternately, nitrogen nucleophiles (giving products such as structures 81 and 82), or sulfur nucleophiles (giving products such as 79 and 89) can be used. Yet another choice would be the use of phosphate nucleophiles, giving δ-substituted tetraphosphate derivatives falling within the scope of the invention. Thus, for example, treatment of the cyclical trimetaphosphate with 2-naphthylmethyl phosphate would yield structure 76, while benzyl phosphate would yield 85. Yet another choice would be the use of phosphonic acid derivatives as nucleophiles, again giving δ-substituted tetraphosphate derivatives falling within the scope of the invention (for example, structures 131, 132, and 133).

Finally, the above Examples are illustrative and more elaborate molecules can be used to generate other compounds within the scope of the present invention, bearing novel substituents on the sugar and/or the base, by use of the appropriate reagents.

Example 7

2',3'-((benzyl)methylenedioxy)-7-(n-propyl)-uridine 5'-triphosphate

Uridine 5'-triphosphate, trisodium salt (1.0 g, 1.82 mmol) was dissolved in 98% formic acid (5 mL) and phenylacetaldehyde, dimethyl acetal (602 uL, 3.64 mmol) added. The reaction was stirred overnight at ambient temperature, at which point TLC (silica gel, 50% isopropanol/50% ammonium hydroxide) and HPLC (C18) showed good conversion to a less polar product. The formic acid was removed on a rotary evaporator, and the residue partitioned between 1 M sodium bicarbonate (15 mL) and ethyl acetate (25 mL). The layers were separated and the aqueous was washed with a further portion of ethyl acetate (25 mL). The aqueous layer was stripped and the residue lyophilized overnight. The crude product was dissolved in water (5 mL) and the components separated by preparative HPLC (Waters Novapak C18, 6 um, 25×100 mm, gradient from 0.1 M ammonium acetate to methanol over 30 minutes, 30 mL/min, monitor at 260 nm). The yield of the acetal was 352 mg (30%).

$^1$H NMR (D$_2$O, 300 MHz): δ 7.62 (d, 1H), 7.22 (m, 5H), 5.73 (d, 1H), 5.40 (d, 1H), 5.32 (t, 1H), 4.69 (m, 2H), 4.33 (m, 1H), 4.00 (m, 2H), 3.01 (d, 2H). $^{31}$P NMR (D$_2$O, 121.47 MHz): δ −7.47 (d, 1P), −10.54 (d, 1P), −21.46 (t, 1P).

The title compound is obtained by further manipulation according to the method of example 1.

Example 8

2',3'-((benzyl)methylenedioxy)-uridine 5'-monophosphate

Uridine 5'-monophosphate, disodium salt (1.0 g, 2.72 mmol) was dissolved in 98% formic acid (7.5 mL) and phenylacetaldehyde, dimethyl acetal (900 uL, 5.44 mmol) added. The reaction was stirred for 2 days at 30° C., after which the formic acid was removed and the residue partitioned between 1 M sodium bicarbonate (20 mL) and ethyl acetate (20 mL). The layers were separated and the aqueous was extracted once more with ethyl acetate (20 mL). The aqueous layer was concentrated to 8 mL and the product separated using preparative HPLC, as described in example 7. Yield=241 mg (19%).

The product so obtained is converted to the monotributylammonium salt by direct treatment with an excess of tributylamine in aqueous methanol, after which it is dried by repeated evaporation with dry N,N dimethylformamide. This is treated with 1,1'-carbonyldiimidazole to activate the monophosphate as the corresponding imidazolide, which is coupled with a variety of phosphate-containing nucleophiles, such as cyclohexylphosphate (giving structure 5), n-propylphosphate (giving 9), benzyl phosphate (giving 10), isobutylphosphonic acid (giving 37), 1-naphthylmethylphosphonic acid (giving 41), and n-hexylphosphonic acid (giving 45).

By this general method, a variety of diphosphates bearing substituents on the P phosphate falling within the scope of this invention can be produced. These diphosphates can be further modified with other groups on the sugar and/or the base, as previously described for tri- and tetraphosphates.

Example 10

Uridine 5'-monophosphate (2-fluoro-4-nitrobenzyl)ester

A solution of 2',3'-O-isopropylidene-uridine 5'-monophosphoric acid (0.2 mmol) and 2-fluoro-4-nitrobenzyl alcohol (0.4 mmol) in pyridine (5 mL) is treated with triphenylphosphine (6 mmol) and diethylazodicarboxylate (4 mmol) 7 hours at 28° C. The solvents are removed in vacuo and the residue chromatographed on silica gel with methanol-chloroform as eluent, to isolate 2',3'-O-isopropylidene-uridine 5'-monophosphate (2-fluoro-4-nitrobenzyl)ester. This compound is treated with methanolic HCl 20 minutes at 28° C., and the solvent removed in vacuo to afford the title compound.

Example 11

Parallel Synthesis of Nucleotide Aryl Phosphodiesters

2',3'-O-isopropylidene-uridine and 2',3'-O-isopropylidene-6-N-benzoyl-adenosine (0.1 mmol) are placed in the wells of a reaction block and dissolved in dichloromethane (3 mL/well). Each well is treated with 2-cyanoethyl-N,N'-diisopropyl chlorophosphoramidite (0.2 mmol) and triethylamine (0.4 mmol) and agitated for 20 minutes at 25° C. on a shaker. The solvent is evaporated under a stream of nitrogen and the block dried in a vacuum oven overnight. To each of the uridine-containing wells is added 0.2 mmol of a different alcohol selected from the group of Table A, as a solution in dichloromethane. The process is repeated for the adenosine-containing wells. Tetrazole (0.3 mmol) is added and the array is shaken 10 minutes at 25° C. The reaction block is next immersed in a $CO_2$-acetonitrile bath and mCPBA (0.5 mmol in 1 mL THF/well) added. The block is shaken and allowed to come to room temperature. An additional 2 mL of dichloromethane per well is added and each well extracted with 5% sodium thiosulfate (2×1 mL) followed by 10% sodium bicarbonate (1×1 mL) and brine (1×1 mL). The organic phase is made 50% in trifluoroacetic acid and shaken 60 minutes at 25° C. The organic phase is again dried under nitrogen and treated with aqueous ammonia in THF overnight. It is then evaporated under a stream of nitrogen, and the residue extracted with ether (3×1 mL). Each product is solubilized in alcohol and applied to the top of individual C18 extraction columns. Nitrogen is passed through the column to evaporate the alcohol and the column is eluted stepwise with water, 10% methanol-water, 25% methanol-water, and 50% methanol-water to afford the desired products.

TABLE A

Coupling Partners for 2', 3'-O-isopropylidene-uridine 5'-phosphoramidate and 2', 3'-O-isopropylidene-6-N-benzoyl-adenosine 5'-phosphoramidate.

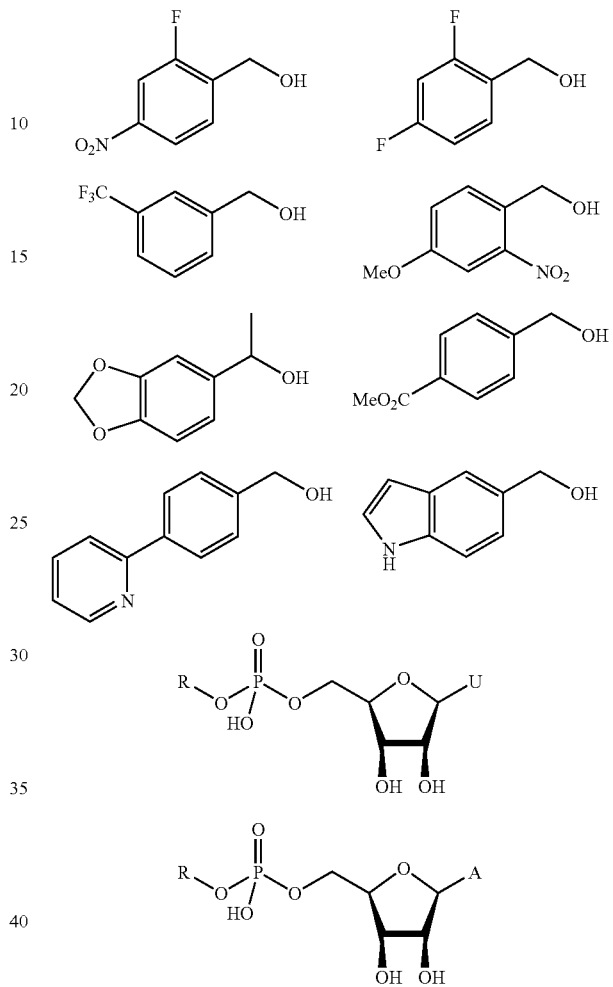

Example 12

2',3'-(trans)-O-methylenenstyryl-5'-(methylphosphono)-$N^6$-ethylaminocarbonyl-adenosine (Compound 218)

2',3'-(trans)-O-methylenenstyryl-$N^6$-ethylaminocarbonyl-adenosine (Compound 218), (50 mg, 0.11 mmol) and methylphosphonic acid (21 mg, 0.22 mmol) were dissolved in pyridine (2.00 mL). N,N'-cyclohexylcarbodiimide (91 mg, 0.44 mmol) was added and the reaction stirred overnight at 35° C. The pyridine was removed by evaporation and the residue reconstituted in water (10 mL). The product was purified by reverse phase preparative HPLC ($C_{18}$; gradient from 0.05 M ammonium acetate (pH 6) to methanol). The yield of the title compound following lyophilization was 52 mg (89%).

$^1$H NMR ($D_2O$, 300 MHz): δ 8.18 (d, 2H), 6.99 (m, 5H), 6.35 (d, 1H), 6.04 (d, 1H), 5.86 (d, 1H), 5.53 (m, 1H), 5.18 (m, 1H), 4.95 (m, 1H), 4.40 (m, 1H), 3.92 (m, 2H), 3.17 (t, 2H), 1.01 (m, 6H). $^{31}$P NMR (121.47 MHz, $D_2O$): δ +28.46 (s, 1P). MW calculated for $C_{23}H_{27}N_6O_7P$ (MH$^+$): 530.47, found 531.38 by LCMS.

Example 13

2',3'-trans-O-methylenestyryl-5'-(ethylphosphono)-
$N^6$-ethylaminocarbonyl-adenosine (Compound 219)

The ethyl phosphonate was made according to the method of Example 12. Yield was 78%.

$^1$H NMR (D$_2$O, 300 MHz): δ 8.35 (d, 2H), 7.19 (m, 5H), 6.62 (d, 1H), 6.21 (d, 1H), 6.01 (d, 1H), 5.70 (m, 1H), 5.34 (m, 1H), 5.05 (m, 1H), 4.50 (m, 1H), 3.94 (m, 2H), 3.21 (t, 2H), 1.27 (m, 2H), 1.07 (t, 3H), 0.72 (m, 3H). $^{31}$P NMR (121.47 MHz, D$_2$O): δ +32.14 (d, 1P). MW calculated for C$_{23}$H$_{27}$N$_6$O$_7$P (MH$^+$): 544.50, found 545.62 by LCMS.

Example 14

Platelet Aggregation Assays

Blood was collected from healthy volunteers into syringes containing ⅙ final blood volume of anti-coagulant ACD (65 mM citric acid, 85 mM sodium citrate, 110 mM dextrose) for washed platelet (WP) preparation or into a syringe containing a final concentration of 10 units/mL heparin or 300 μM PPACK for whole blood (WB) assays. The blood collected for whole blood assays was maintained at room temperature and immediately tested as described below. The blood collected for WP was centrifuged at 180 g for 15 minutes and the supernatant (platelet rich plasma) was removed. The platelet rich plasma was centrifuged and the platelets were pelleted and resuspended in a buffer consisting of (mM): NaCl (137), KCl (2.7), CaCl$_2$ (2) MgCl$_2$ (1), NaH$_2$PO$_4$ (3), Glucose (5), HEPES (10), pH 7.4, 0.2% BSA. These centrifugations and washes were repeated twice following by resuspension in the media described above containing 0.25 U apyrase/mL. Platelet aggregation was measured using the optical mode of a ChronoLog aggregometer (Havertown, Pa.). Five hundred μl of platelet suspension containing 1 mg/mL Fibrinogen were warmed to 37° C. and stirred at 1000 rpm. A maximally effective concentration of ADP (typically a concentration that produces between 90 and 100 percent of the maximal response) was added to the sample and aggregation was monitored for 8 minutes. The effects of Compounds 217-219 were studied following the same protocol with the exception that the inhibitor was incubated for 2-5 minutes prior to the addition of a maximally effective concentration of ADP. For whole blood aggregation, blood was diluted 1:1 with saline and then aggregation was performed in the same manner as described above using the impedance mode of the aggregometer.

The potency of agonists and inhibitors of platelet aggregation was calculated from both, the rate of aggregation and the maximal extent of aggregation obtained for each determination by fitting the data to a four-parameter logistic equation using the GraphPad software package (GraphPad Corp. San Diego, Calif.).

The ability of P2Y$_{12}$ antagonists to inhibit platelet aggregation is presented as IC$_{50}$ (see Table B), the IC$_{50}$ values represent the concentration of antagonist needed to inhibit by 50% the aggregation elicited by a given concentration of ADP.

TABLE B

| Compound # | PLATELET DATA IC50 (μM) Washed Platelets | PLATELET DATA IC50 (μM) Whole Blood |
|---|---|---|
| 217 | not tested | 2.5 |
| 218 | 0.2 | 0.43 |
| 219 | 0.2 | not tested |

What is claimed is:

1. A pyrimidine diphosphate selected from the group consisting of Compound 37-72, or a pharmaceutically acceptable salt, solvate, or hydrate thereof:

37

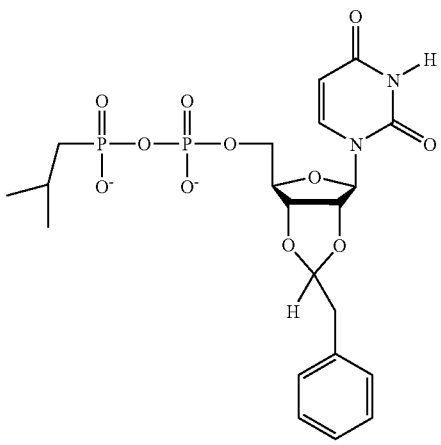

38

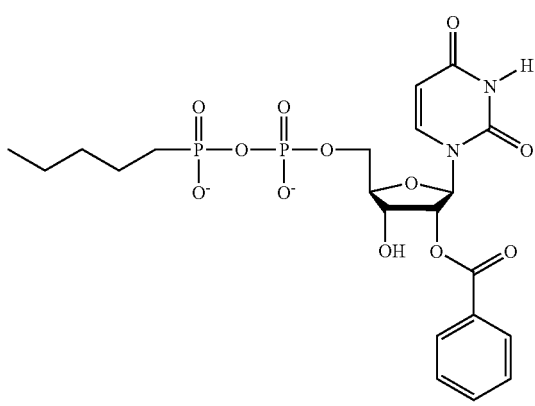

39

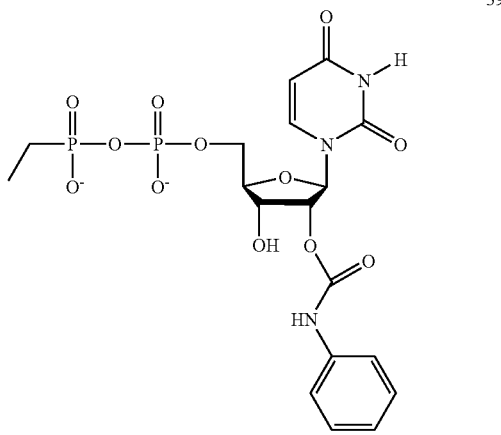

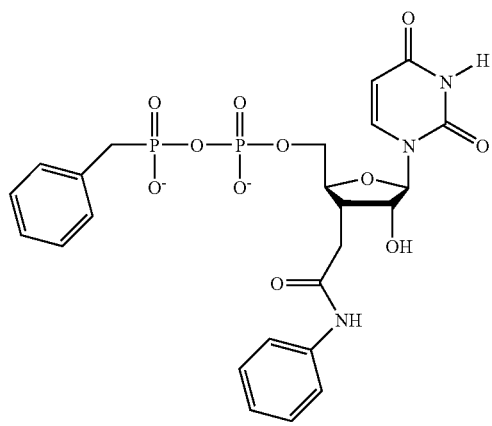
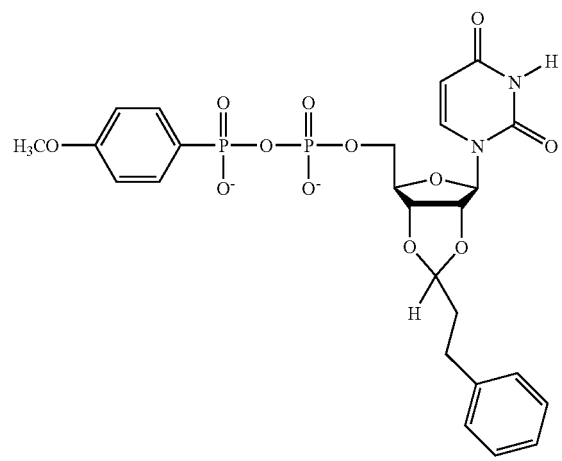
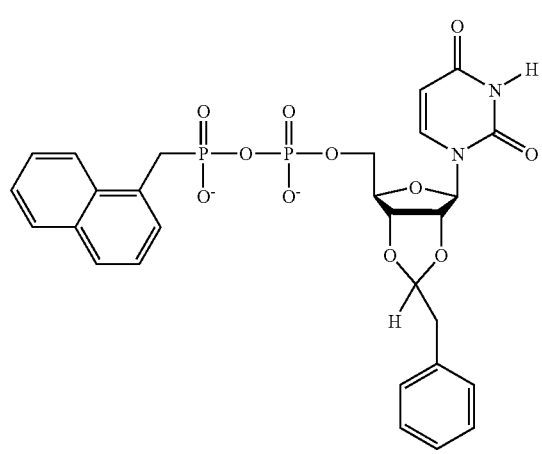
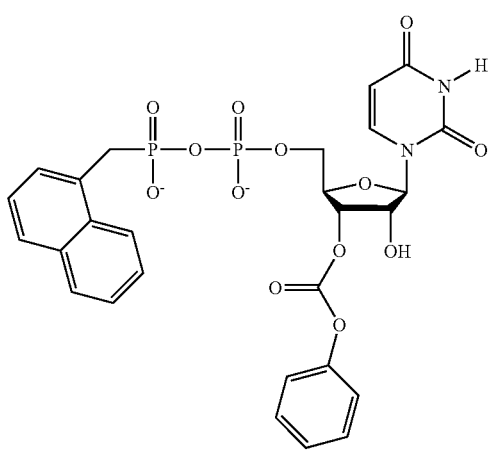
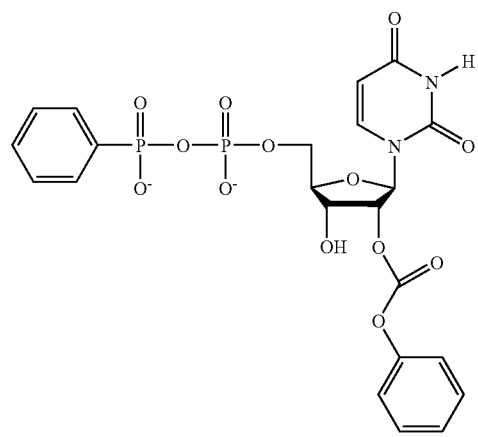
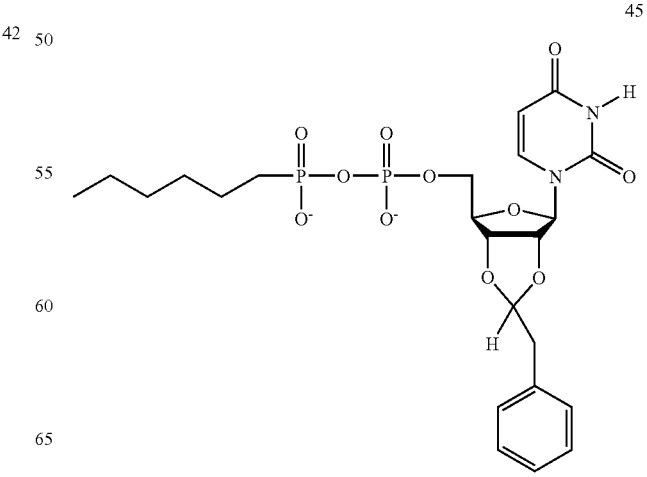

46
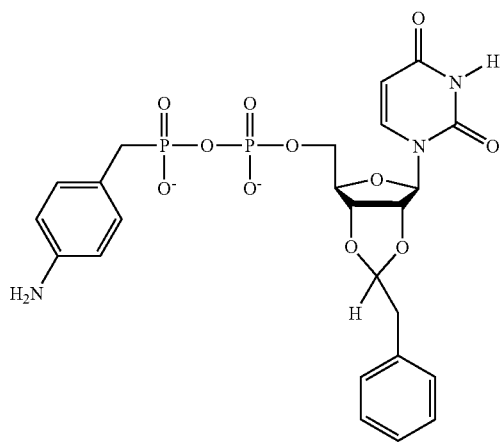
47
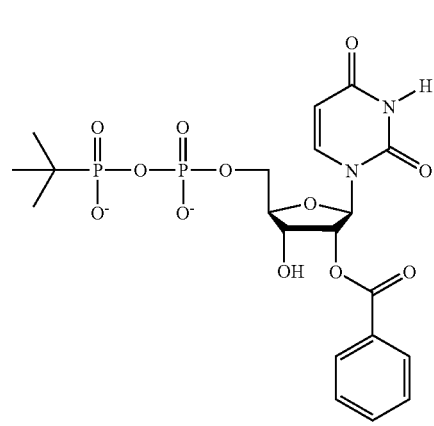
48
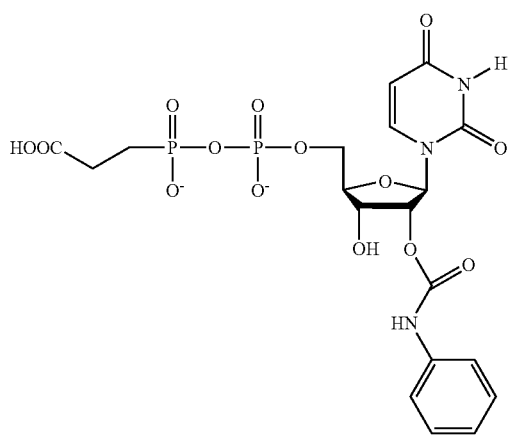
49
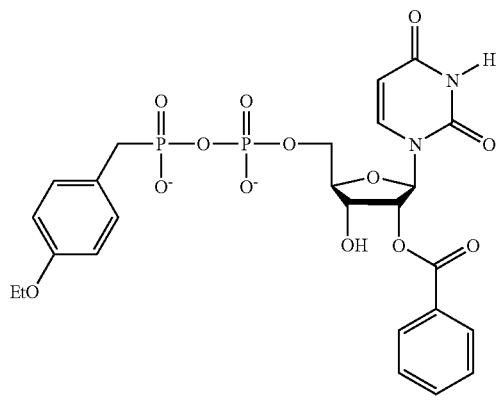
50
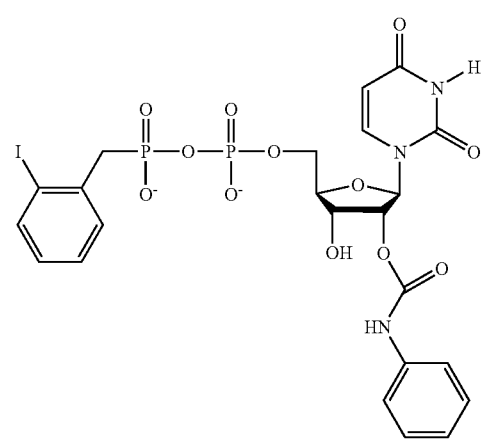
51
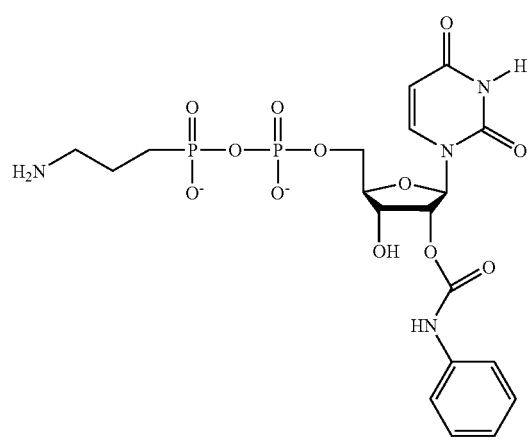

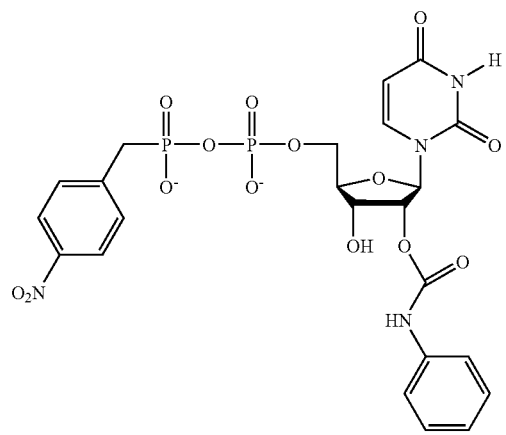
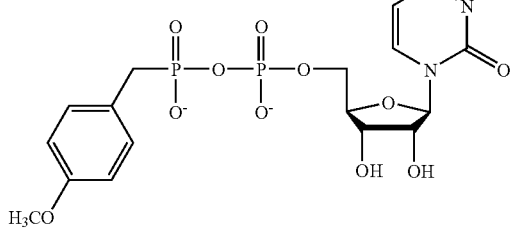
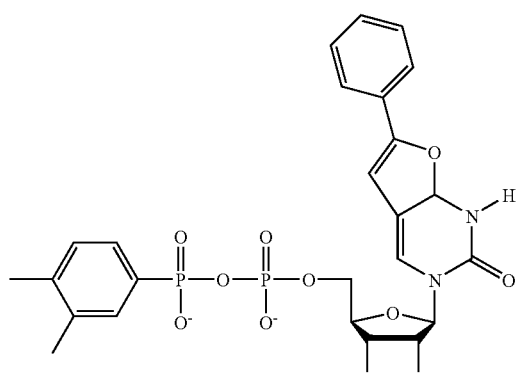
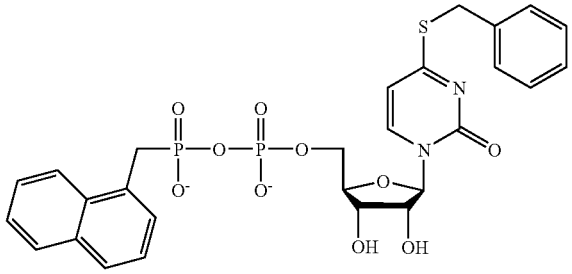
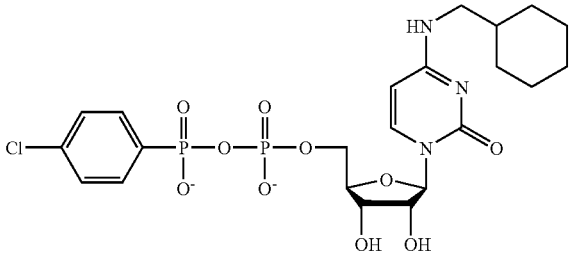
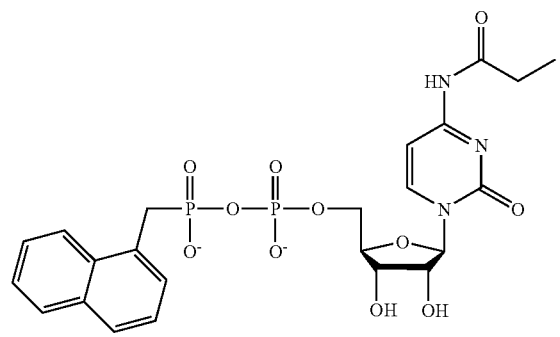
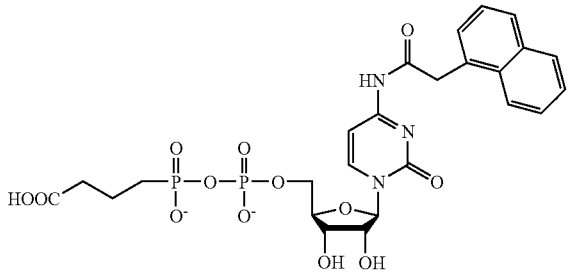

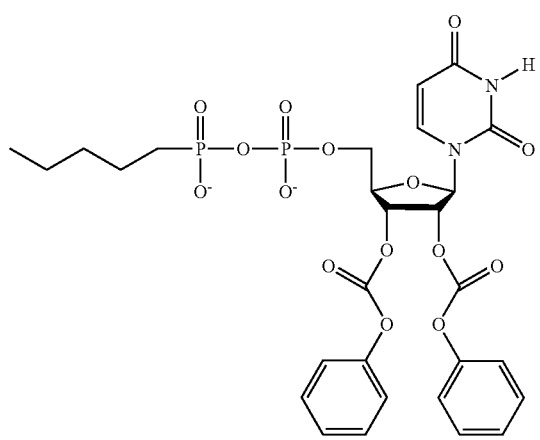
61
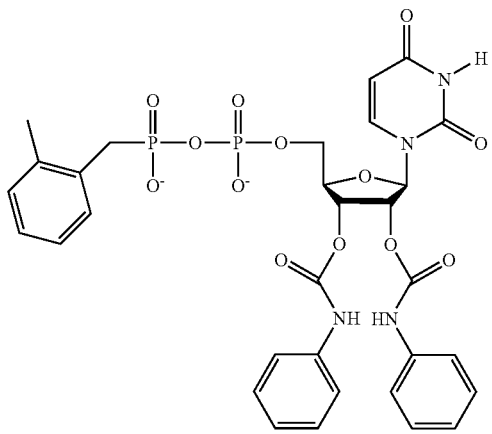
64
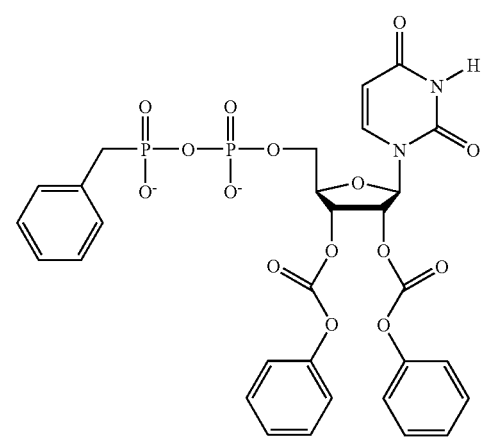
62
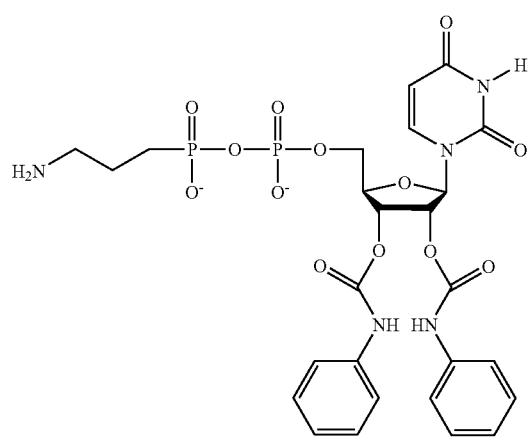
63
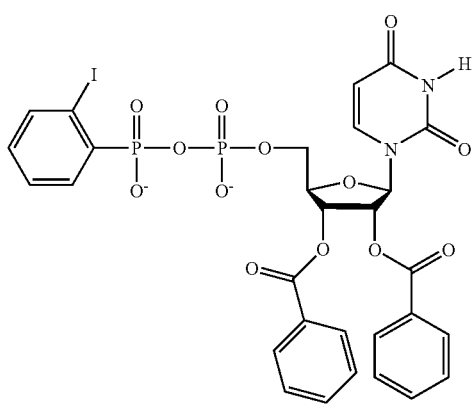
65
66

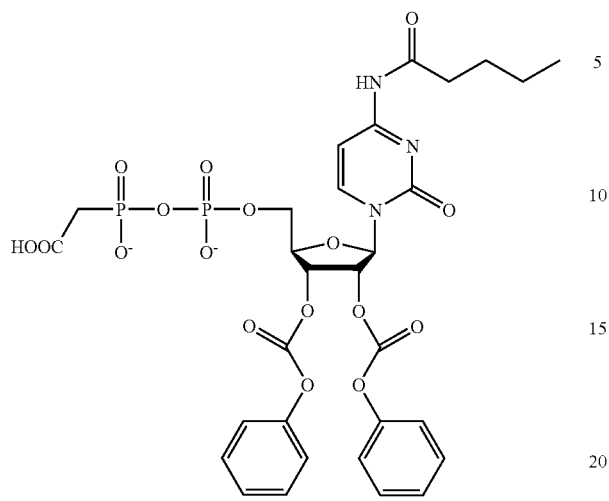
67
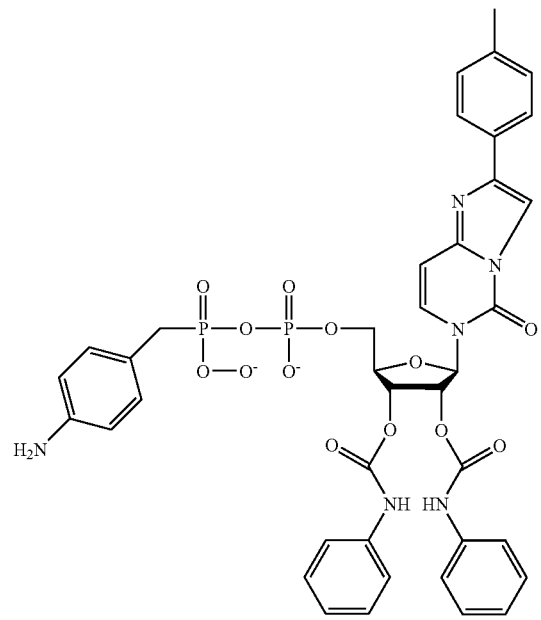
70
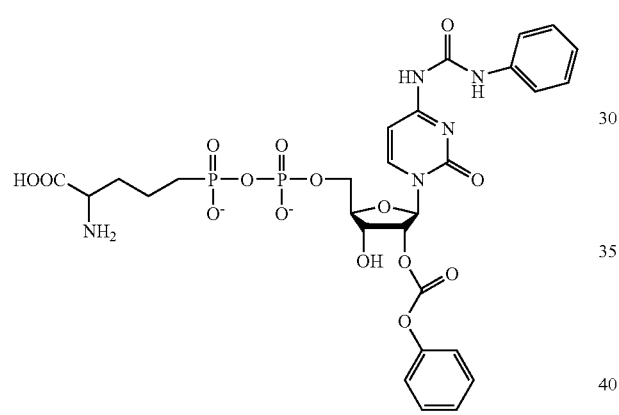
68
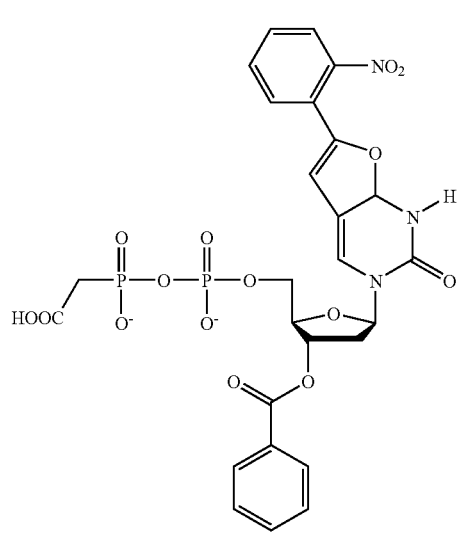
71
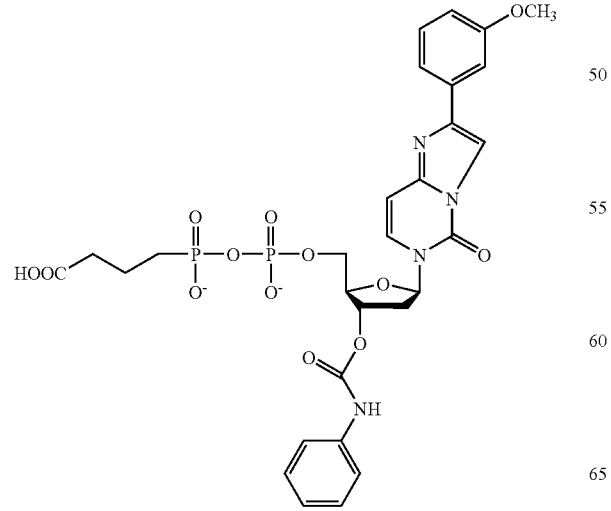
69
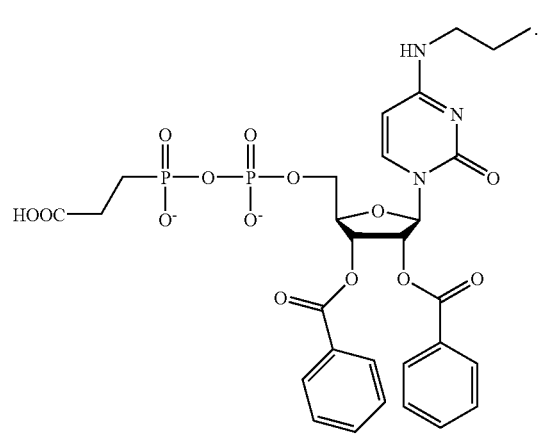
72

2. The pyrimidine diphosphate according to claim 1, which is Compound 37.
3. The pyrimidine diphosphate according to claim 1, which is Compound 45.
4. The pyrimidine diphosphate according to claim 1, which is Compound 63.
5. A pyrimidine triphosphate or a pyrimidine tetraphosphate selected from the group consisting of Compounds 131-168:
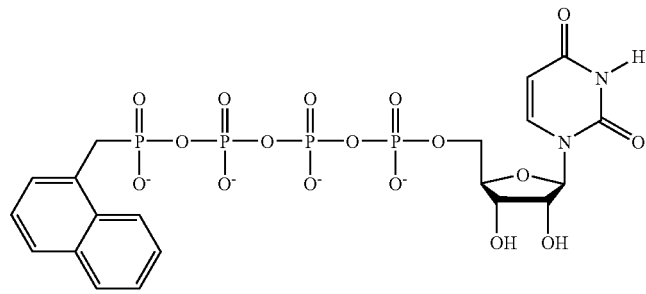
131
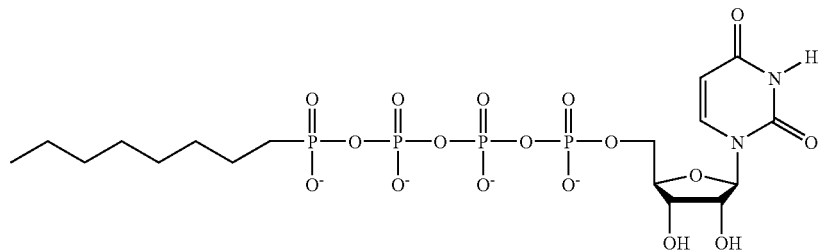
132
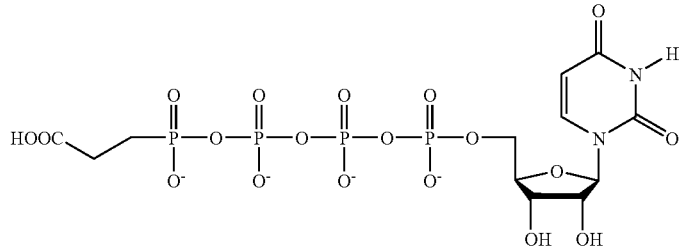
133
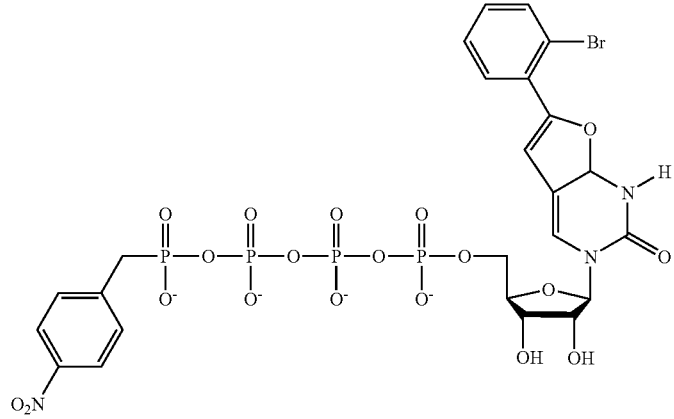
134

-continued
135
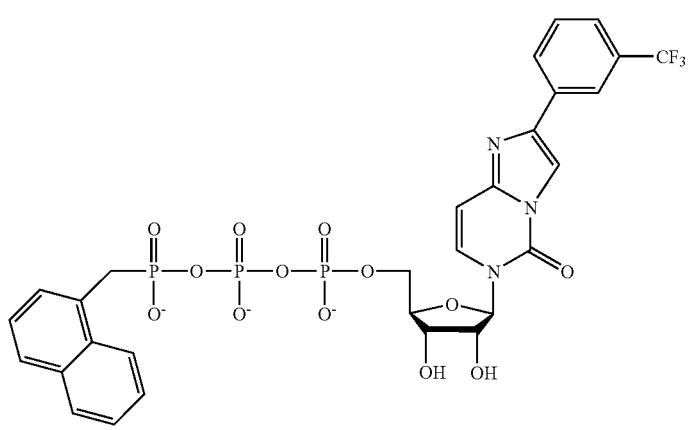
136
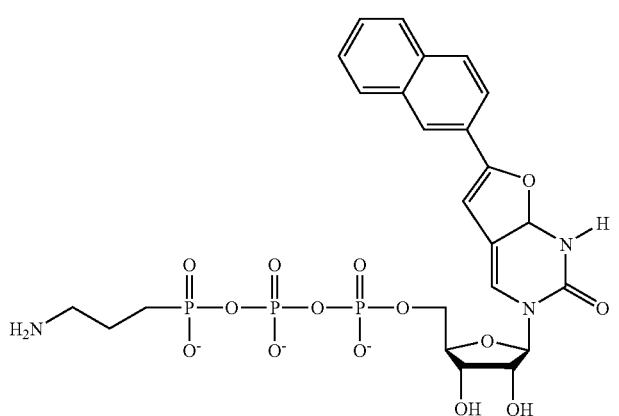
137
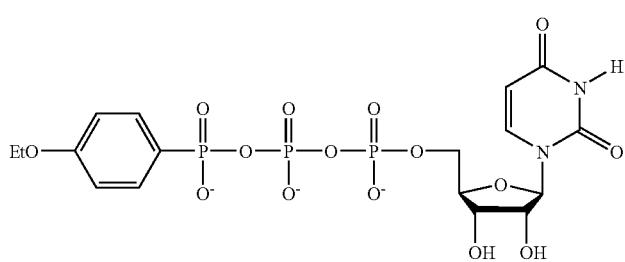
138
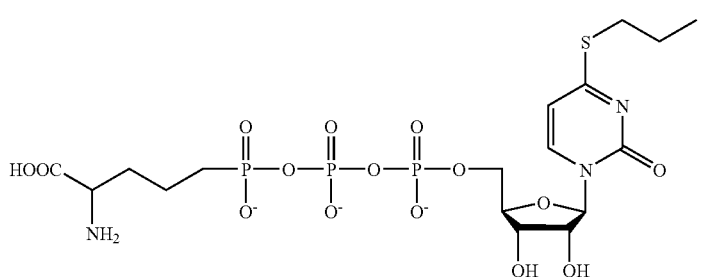
139
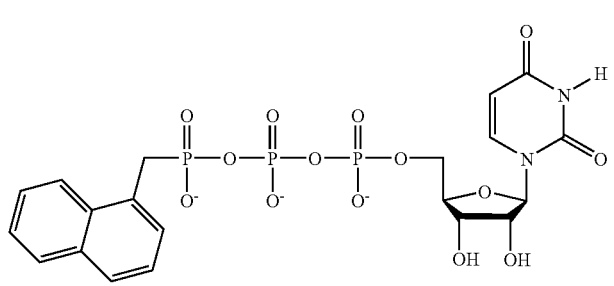

-continued
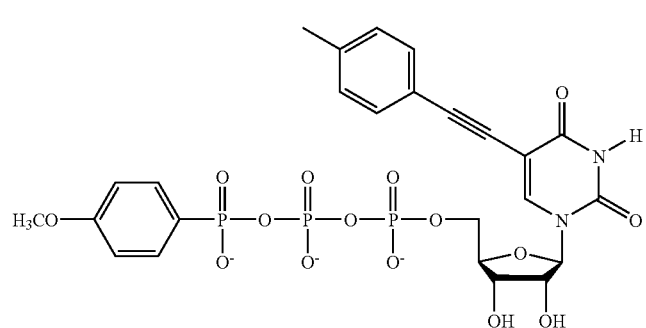
140
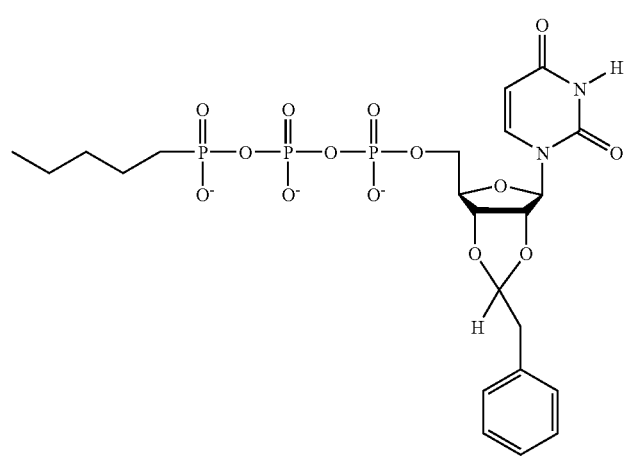
141
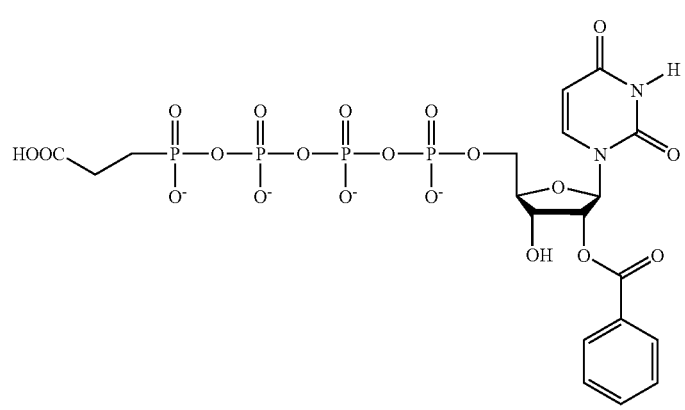
142
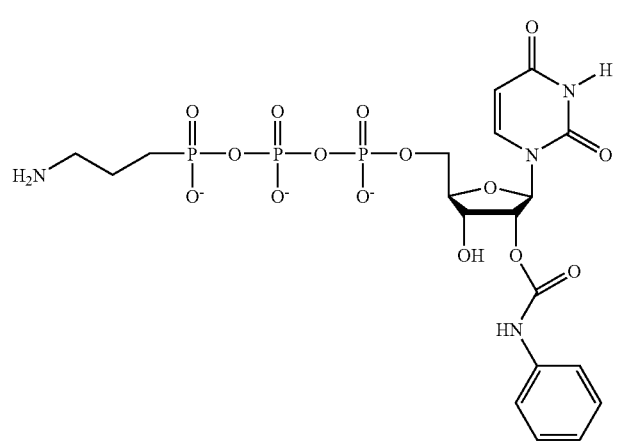
143

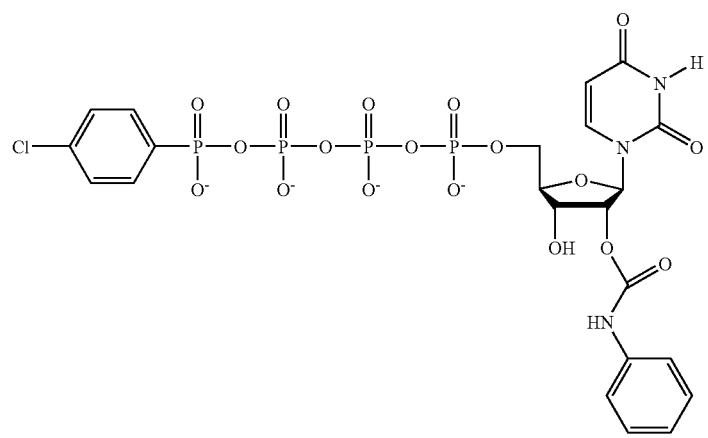
144
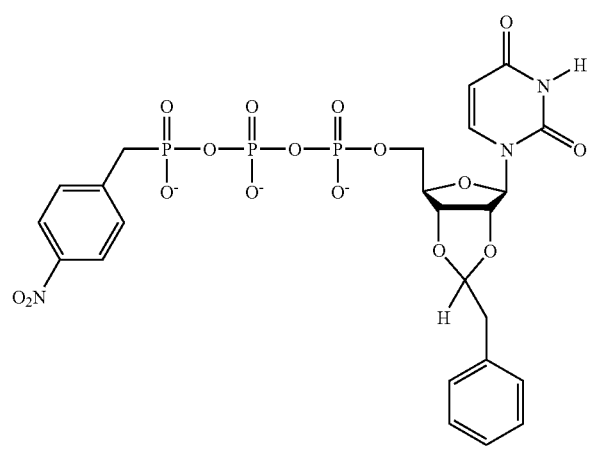
145
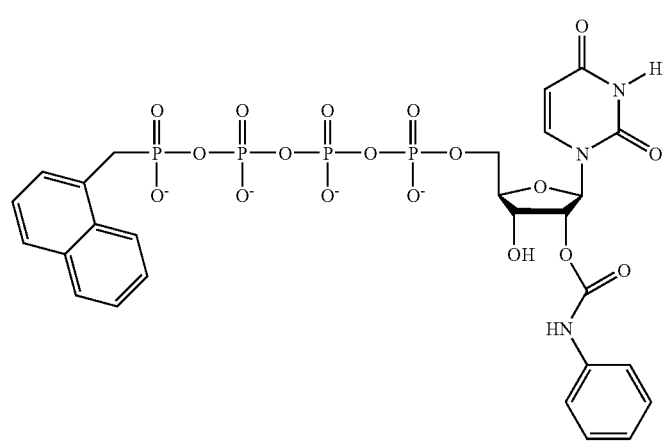
146

147
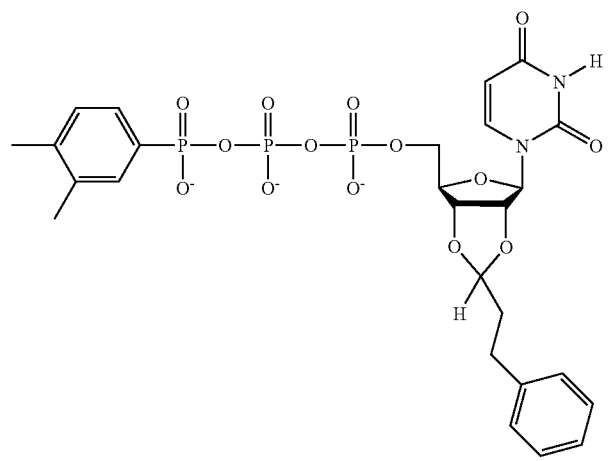
148
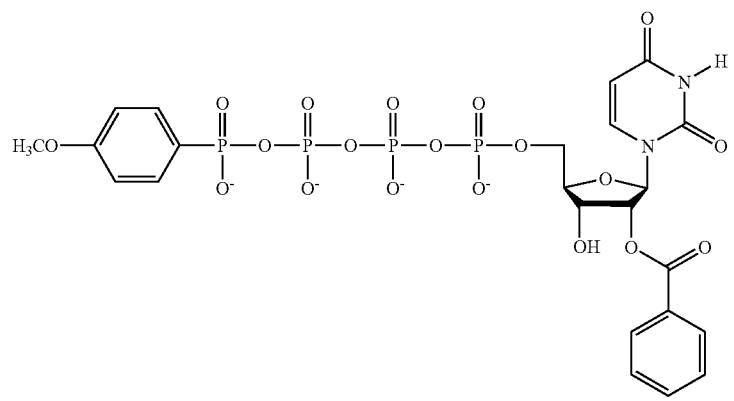
149
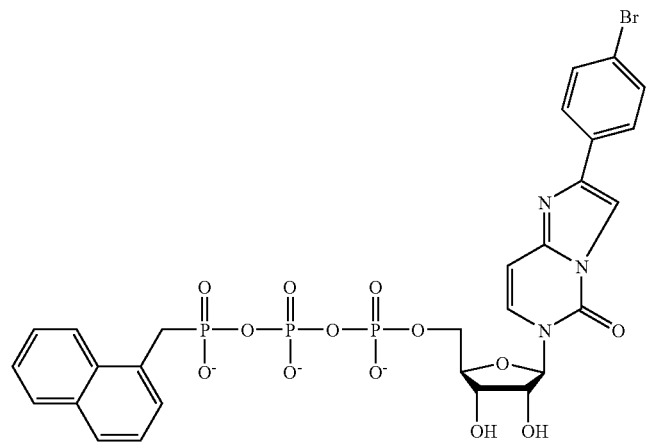

-continued
150
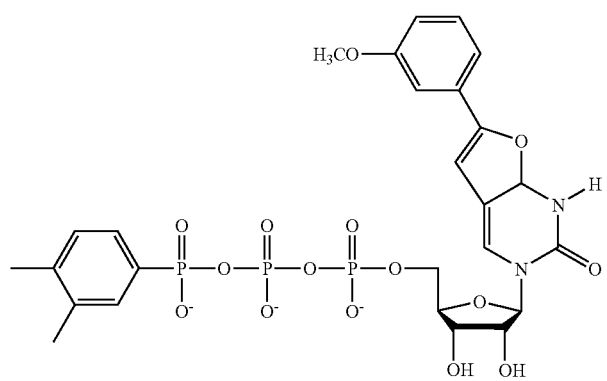
151
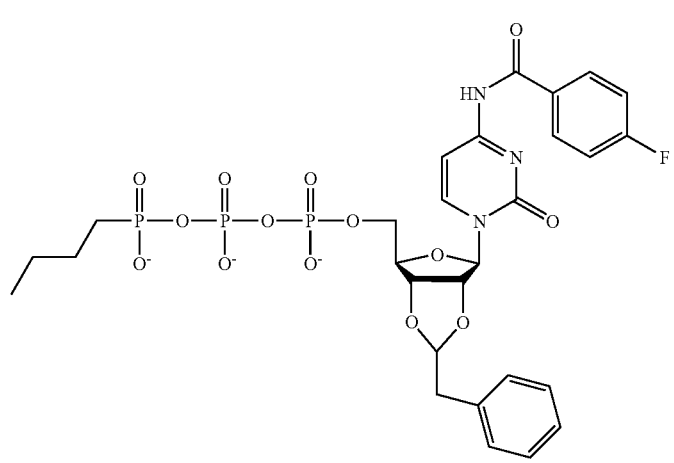
152
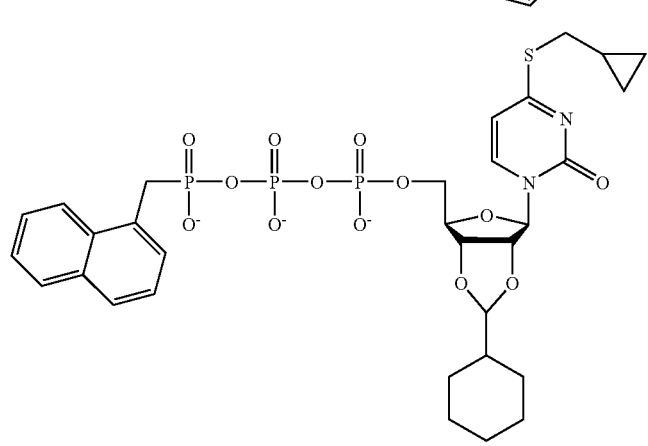
153
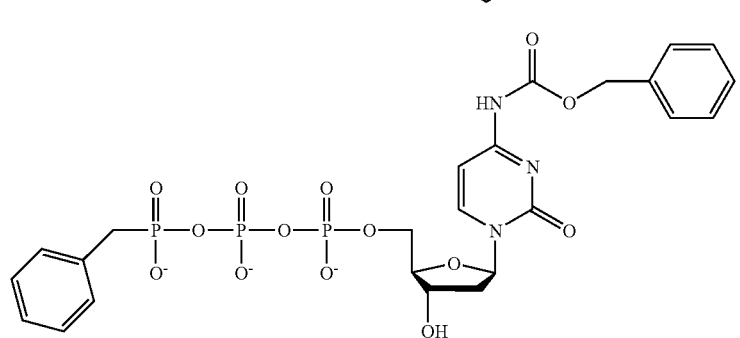

154
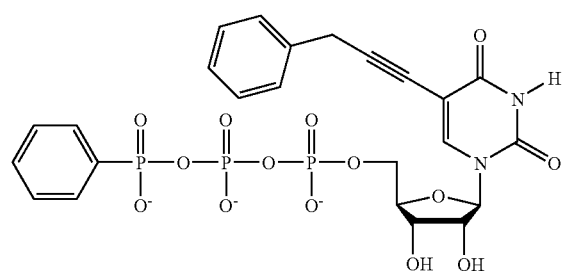
155
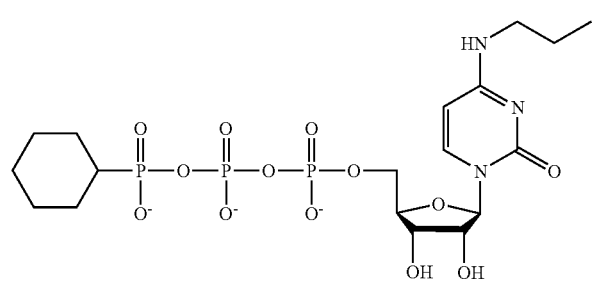
156
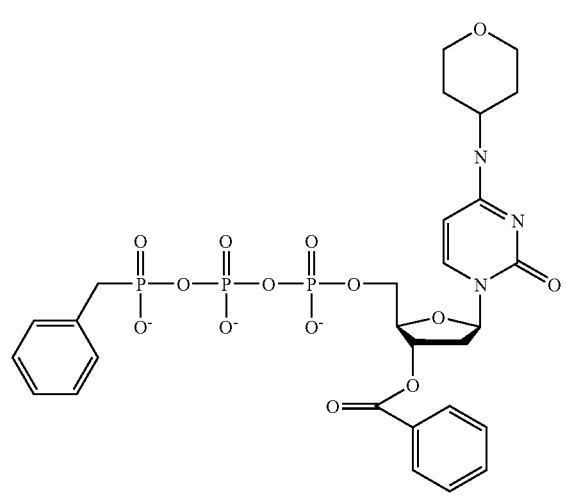
157
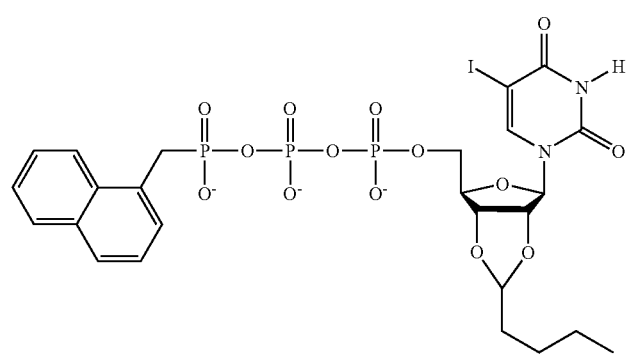

-continued
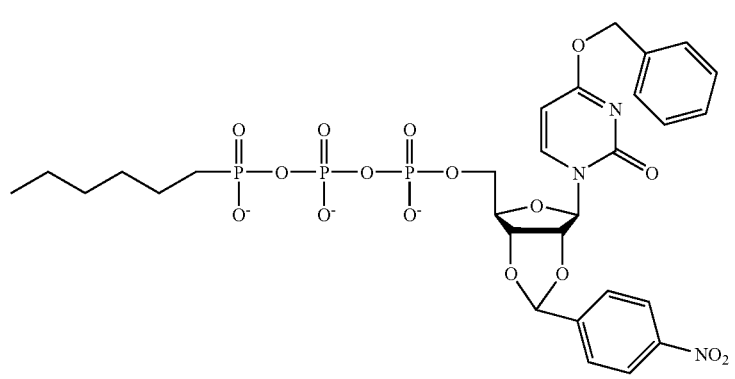
158
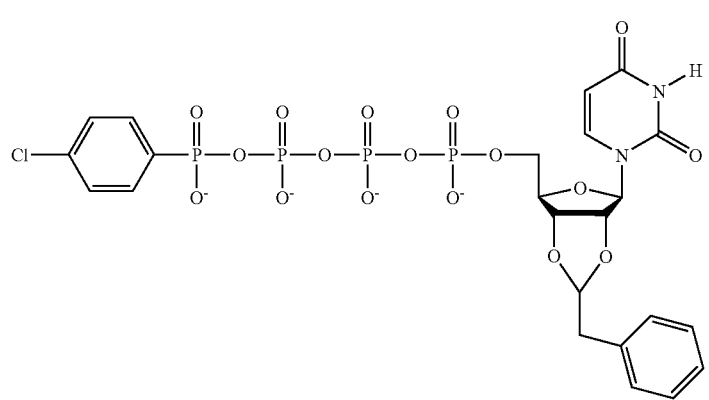
159
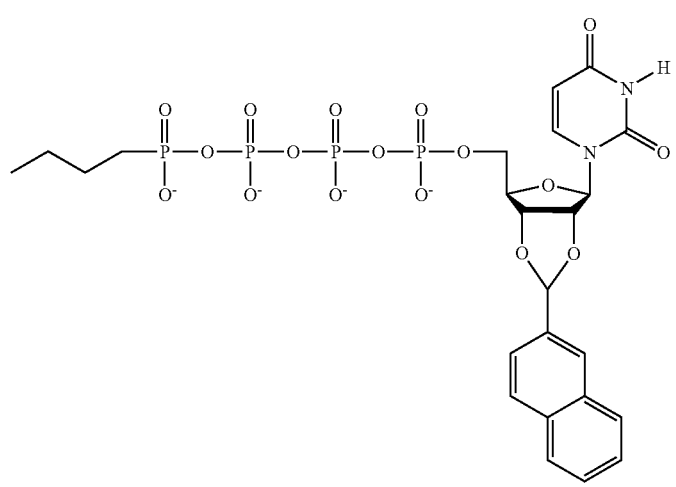
160
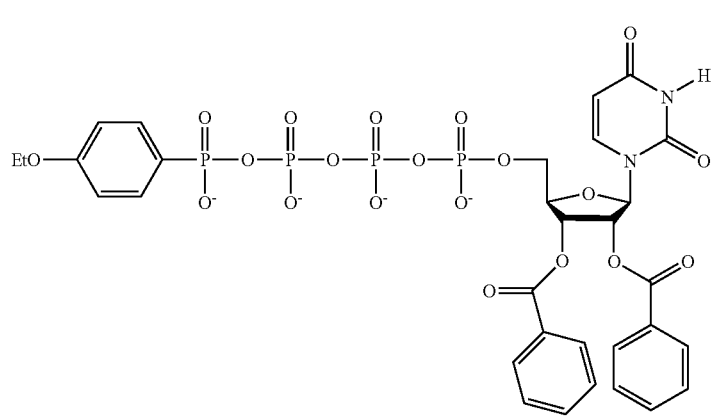
161

-continued
162
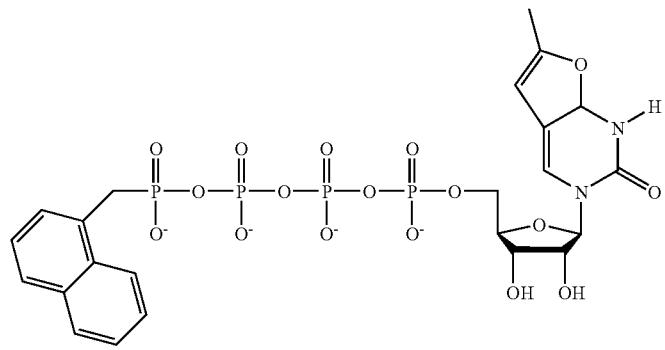
163
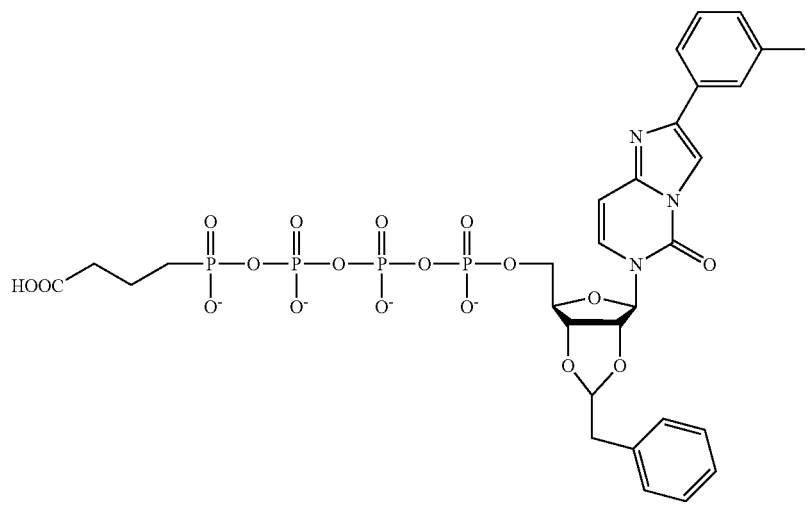
164
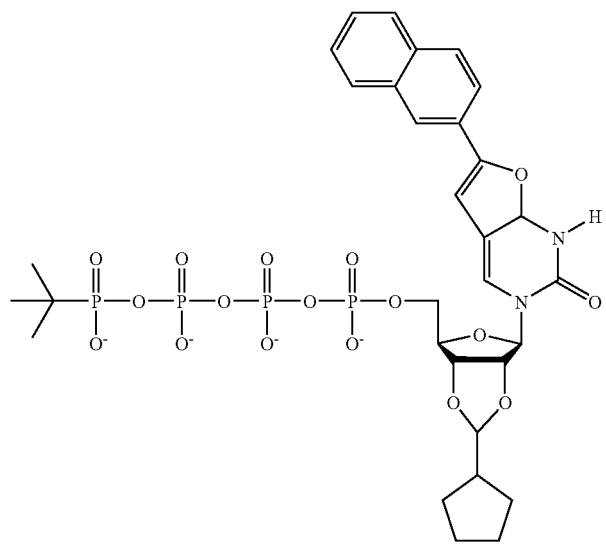

165
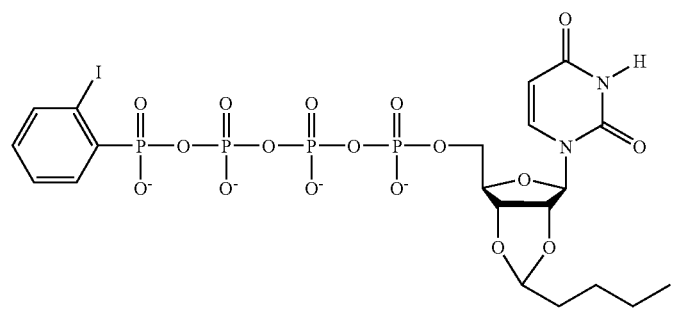
166
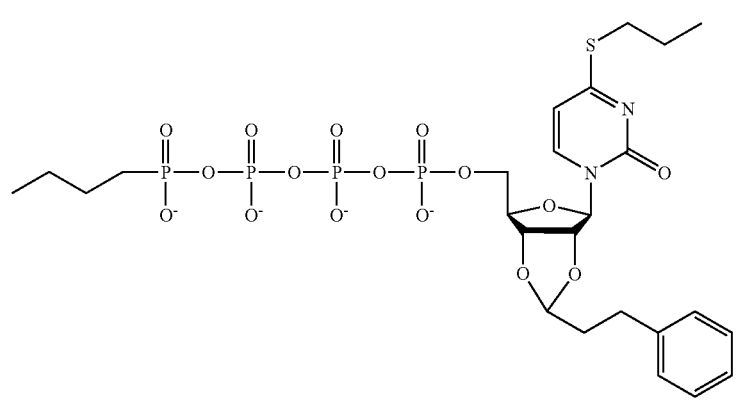
167
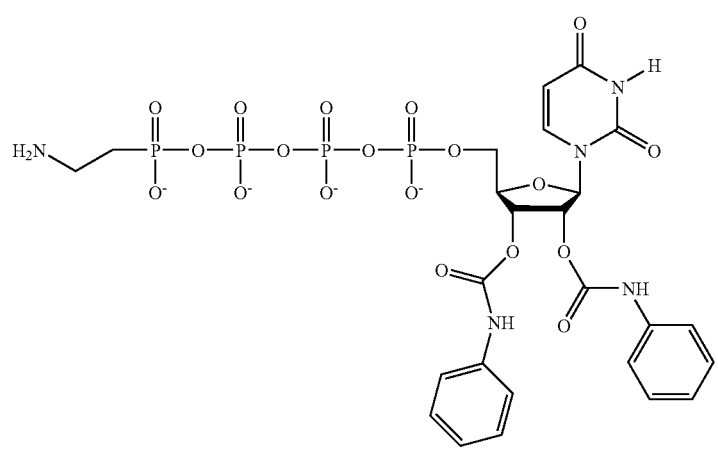
168
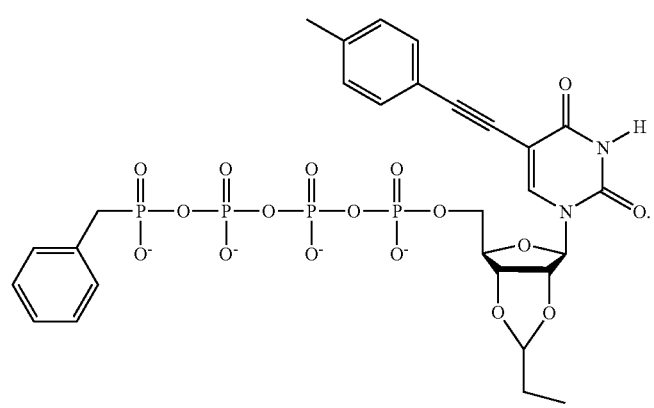

6. A adenonsine triphosphate or an adenonsine tetraphosphate selected from the group consisting of Compound 193-216, or a pharmaceutically acceptable salt, solvate, or hydrate thereof:
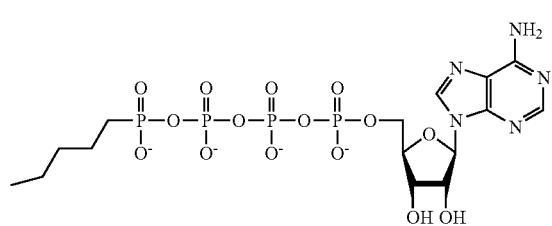
193
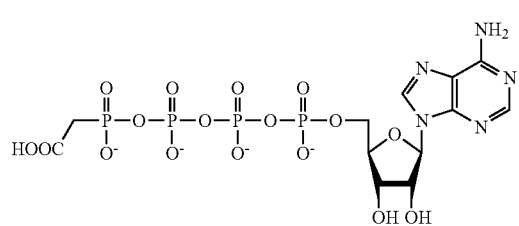
194
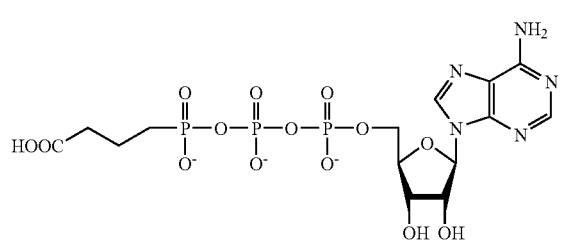
195
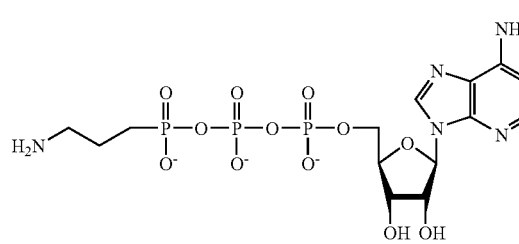
196
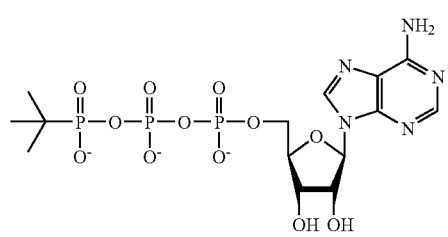
197
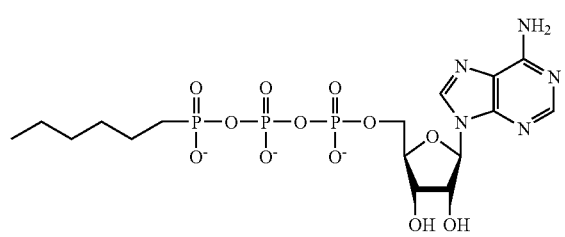
198
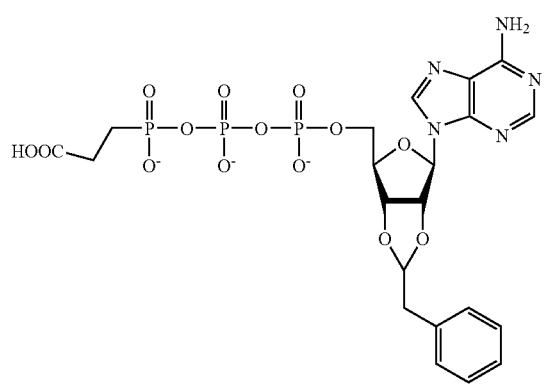
199
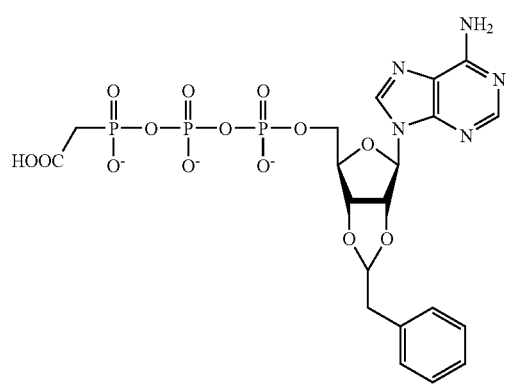
200
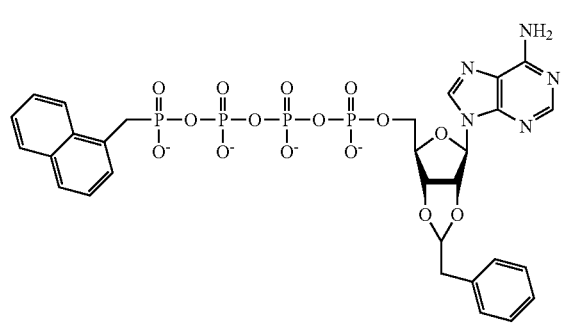
201
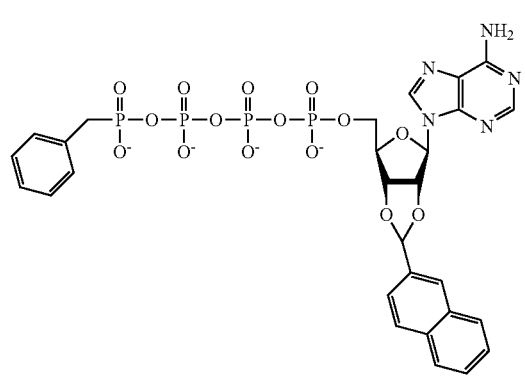
202

-continued
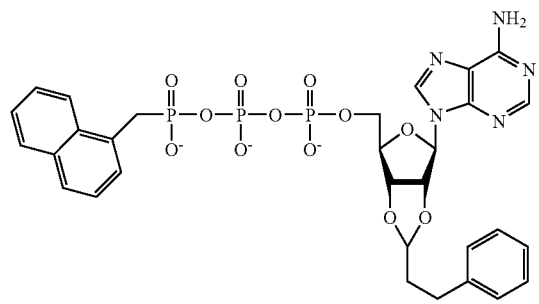
203
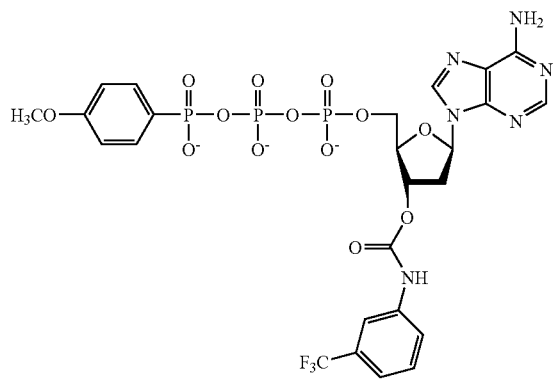
204
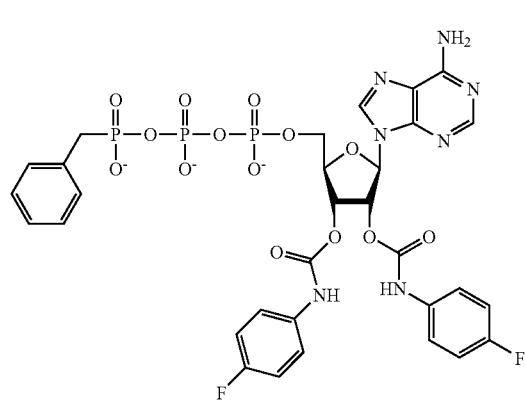
205
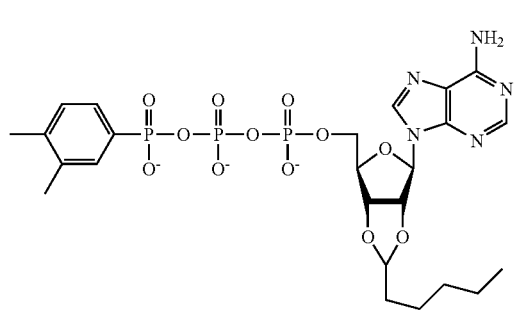
206
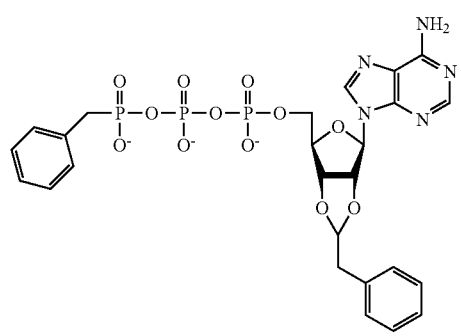
207
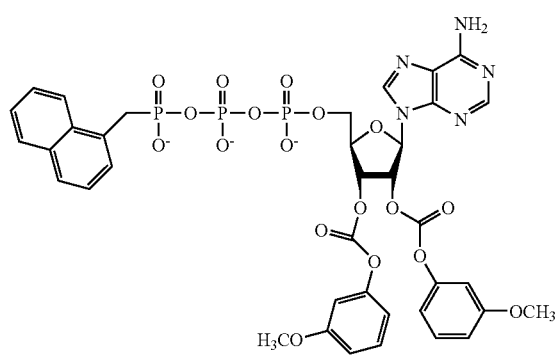
208
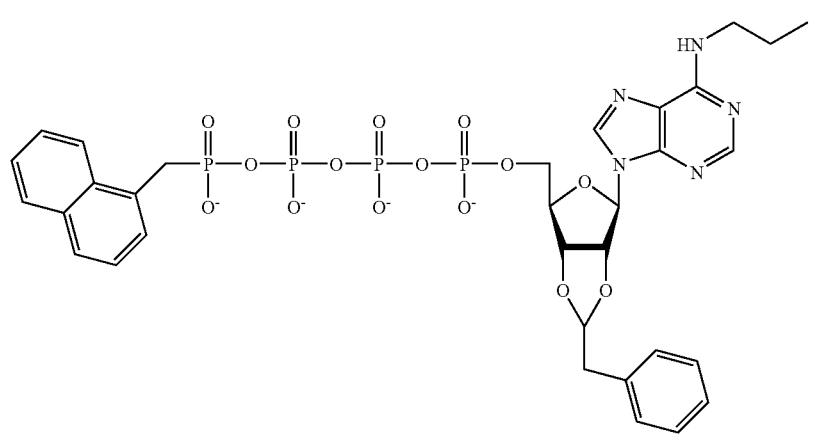
209

-continued
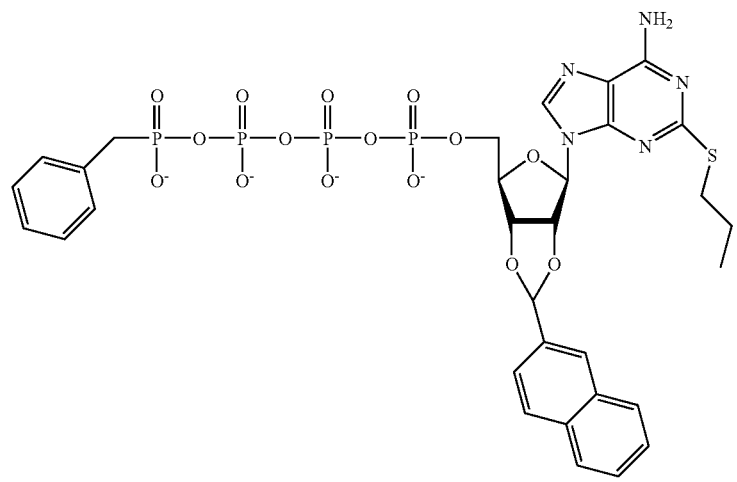
210
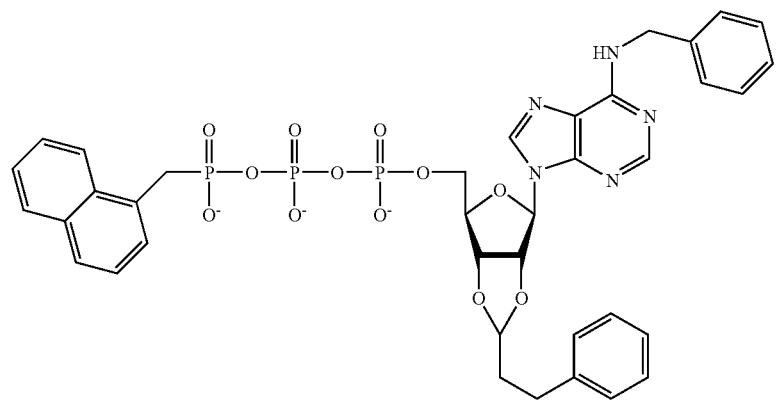
211
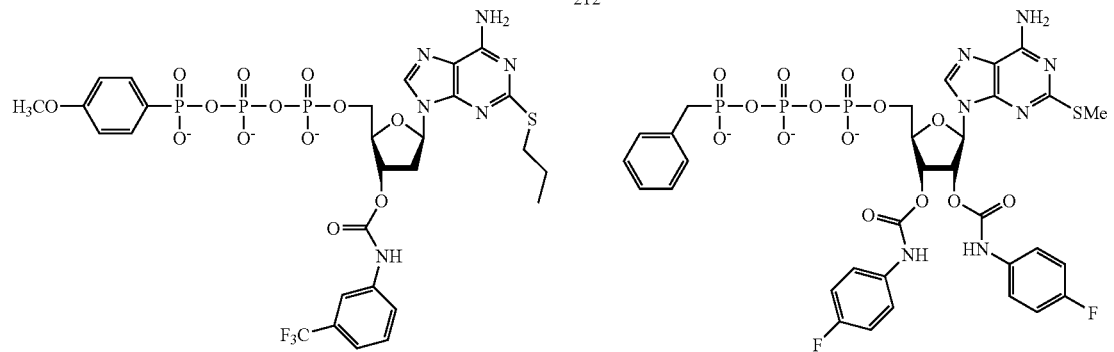
212 213
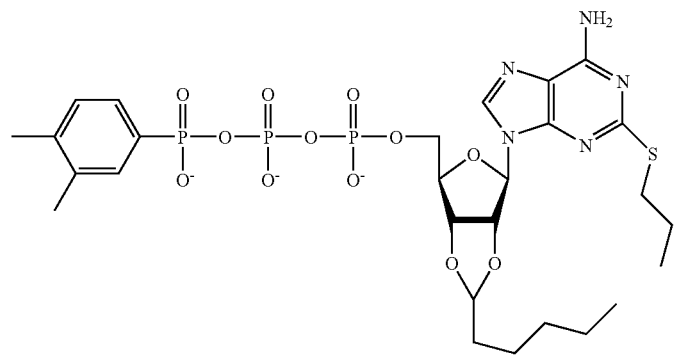
214

-continued
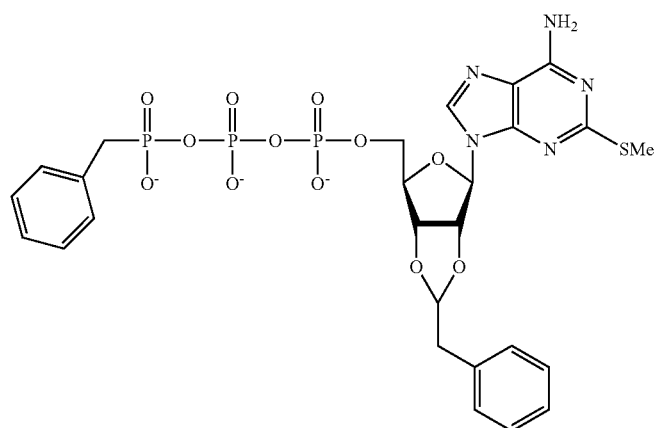
215
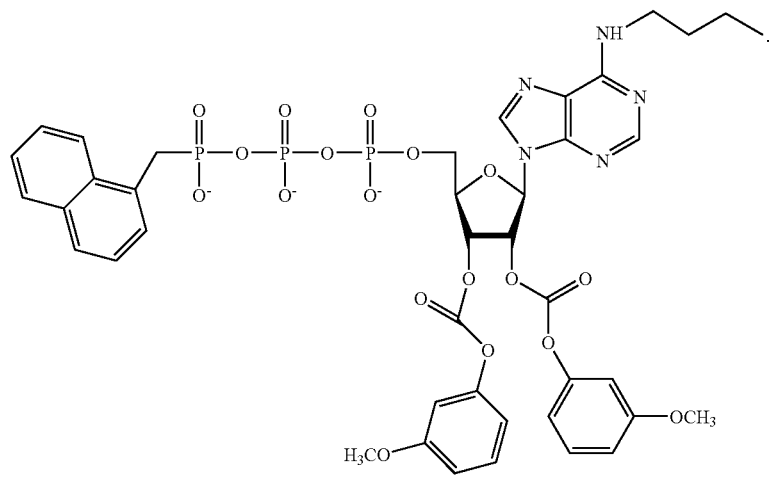
216
* * * * *